United States Patent [19]

Tavtigian et al.

[11] Patent Number: 6,033,857
[45] Date of Patent: Mar. 7, 2000

[54] CHROMOSOME 13-LINKED BREAST CANCER SUSCEPTIBILITY GENE

[75] Inventors: Sean V. Tavtigian; Alexander Kamb, both of Salt Lake City, Utah; Jacques Simard, St. Augustin de Desmuures, Canada; Fergus Couch, St. Davids, Pa.; Johanna M. Rommens, Toronto, Canada; Barbara L. Weber, Merion, Pa.

[73] Assignees: Myriad Genetics, Inc., Salt Lake City, Utah; Endo Recherche, Inc.; HSC Research & Development Limited Parntership, both of Canada; Trustees of the Univ. of Pennsylvania, Philadelphia, Pa.

[21] Appl. No.: 09/044,946

[22] Filed: Mar. 20, 1998

Related U.S. Application Data

[60] Division of application No. 08/639,501, Apr. 29, 1996, Pat. No. 5,837,492, which is a continuation-in-part of application No. 08/585,391, Jan. 11, 1996, abandoned, which is a continuation-in-part of application No. 08/576,559, Dec. 21, 1995, abandoned, which is a continuation-in-part of application No. 08/575,359, Dec. 20, 1995, abandoned, which is a continuation-in-part of application No. 08/573,779, Dec. 18, 1995, abandoned.

[51] Int. Cl.[7] .................. C07H 21/00; C12N 15/63; C12N 15/79; C12N 15/11; C12N 15/09

[52] U.S. Cl. .................. 435/6; 435/7.2; 435/69.1; 435/325; 435/320.1; 536/23.1; 536/23.5

[58] Field of Search .................. 435/6, 7.2, 69.1, 435/325, 320.1; 536/23.1, 23.5

[56] References Cited

FOREIGN PATENT DOCUMENTS

| | | |
|---|---|---|
| 2307477 | 5/1997 | United Kingdom . |
| 9515334 | 6/1995 | WIPO . |
| 9519369 | 7/1995 | WIPO . |
| 9719110 | 5/1997 | WIPO . |

OTHER PUBLICATIONS

"Isolation of expressed sequences that include a gene for familial breast cancer (BRCA2) and other novel transcripts from a five megabase region on chromosome 13q12," ANK Jacob et al., Oncogene (1996) 13, pp. 213–221.

"Generation of an Integrated Transcription Map of the BRCA2 Region on Chromosome 13q12–q13," Fergus J. Couch et al., Genomics 36, Article No. 0428 (1996), pp. 86–99.

"A Strong Candidate for the Breast and Ovarian Cancer Susceptibility Gene BRCA1," Yoshiio Miki et al., Science, vol. 266, Oct. 7, 1994, pp. 66–71.

"Different Tumor types from BRCA2 Carriers Show Wild–Type Chromosome Deletions on 13q12–q13[1]," Julius Gudmundsson et al., Cancer Research 55, Nov. 1, 1995, pp. 4830–4832.

"Somatic and Germline Mutations of the BRCA2 Gene in Sporadic Ovarian Cancer[1]," Karen A. Foster et al., Cancer Research 56, Aug. 15, 1996, pp. 3622–3625.

"A Common Mutation in BRCA2 That Predisposes to a Variety of Cancers Is Found in Both Jewish Ashkenazi and Non–Jewish Individuals[1]," David B. Berman et al., Cancer Research 56, Aug. 1, 1996, pp. 3409–3414.

"Patterns of Loss of Heterozygosity at Loci From Chromosome Arm 13q Suggest a Possible Involvement of BRCA2 in Sproadic Breast Tumors," Fabienne Kerangueven et al., Gene, Chromosomes on Cancer 13, (1995), p. 291–294.

"Loss of heterozygosity in sporadic breast tumours at the BRCA2 locus on chromosome 13q12–q13," A–M Cleton–Jansen, et al., British Journal of Cancer (1995) 72, pp. 1241–1244.

"Consistent loss of the wild type allele in breast cancers from a family linked to the BRCA2 gene on chromosome 13q12–13," Nadine Collins et al., Short Report, Revised Jan. 30, 1995, accepted Jan. 30, 1995, pp. 1673–1675.

"Loss of Heterozygosity on Chomosome 13 is Common Only in the Biologically More Aggressive Subtypes of Ovarian Epithelial Tumors and Is Associated with Normal Retinoblastoma Gene Expression[1]," Timothy M. Kim et al., Advances in Brief, Accepted Dec. 17, 1993, pp. 605–609.

"BRCA2 germline mutations in male breast cancer cases and breast cancer families," Fergus J. Couch et al., Nature Genetics, vol. 13, May 1996, pp. 123–125.

"Mutation analysis of the BRCA2 gene in 49 site–specific breast cancer families," Catherine M. Phelan et al., Nature Genetics, vol. 13, May 1996, pp. 120–122.

"Recurrent BRCA2 6174delT mutations in Ashkenazi Jewish woman affected by breast cancer," Susan Neuhausen et al., Nature Genetics, vol. 13, May 1996, pp. 126–128.

"Loss of heterozygosity in human ductal breast tumors indicated a recessive mutation on chromosome 13," Catharina Lundberg et al., Proc. Natl. Acad. Sci. USA, vol. 84, Apr. 1987, pp. 2372–2376.

(List continued on next page.)

*Primary Examiner*—Karen M. Hauda
*Attorney, Agent, or Firm*—Rothwell, Figg, Ernst & Kurz, P.C.

[57] ABSTRACT

The present invention relates generally to the field of human genetics. Specifically, the present invention relates to methods and materials used to isolate and detect a human breast cancer predisposing gene (BRCA2), some mutant alleles of which cause susceptibility to cancer, in particular breast cancer. More specifically, the invention relates to germline mutations in the BRCA2 gene and their use in the diagnosis of predisposition to breast cancer. The present invention further relates to somatic mutations in the BRCA2 gene in human breast cancer and their use in the diagnosis and prognosis of human breast cancer. Additionally, the invention relates to somatic mutations in the BRCA2 gene in other human cancers and their use in the diagnosis and prognosis of human cancers. The invention also relates to the therapy of human cancers which have a mutation in the BRCA2 gene, including gene therapy, protein replacement therapy and protein mimetics. The invention further relates to the screening of drugs for cancer therapy. Finally, the invention relates to the screening of the BRCA2 gene for mutations, which are useful for diagnosing the predisposition to breast cancer.

8 Claims, 9 Drawing Sheets

OTHER PUBLICATIONS

"Identification by representational difference analysis of a homozygous deletion in pancreatic carcinoma that lies within the BRCA2 region," Mieke Schuttle et al., Proc. Natl. Acad. Sci. USA, vol. 92, Jun. 1995, pp. 5950–5954.

"Linkage to BRCA2 region in hereditary male breast cancer," Steinunn Thorlacius et al., The Lancet, vol. 346, No. 8974, Aug. 26, 1995, pp. 544–545.

"Localization of a Breast Cancer Susceptibility Gene, BRCA2, to Chromosome 13q12–13," Richard Wooster et al., Science, vol. 265, Sep. 30, 1994, pp. 2088–2090.

"Identification of the breast cancer susceptibility gene BRCA2," Richard Wooster et al., Nature, vol. 378, Dec. 21/28, 1995, pp. 789–792.

"Regulating gene expression in transgenic animals," Catherine A. Kappel et al., Biotechnology 1992, 3, pp. 548–553.

"The complete BRCA2 gene and mutations in chromosome 13q–linked kindreds," S. V. Tavtigian et al., Nature Genetics, vol. 12, Mar. 1996, pp. 333–337.

"Confirmation of a susceptibility locus on chromosome 13 in Australian breast cancer families," Sean M. Grimmond et al., Hum Genet (1996) 98, pp. 80–85.

"Further enigmatic variations," Kevin Davies, Nature, vol. 378, Dec. 21/28, 1995, pp. 762–763.

```
   1 GGTGGCGCGA GCTTCTGAAA CTAGGCGGCA GAGGCGGAGC CGCTGTGGCA CTGCTGCGCC
  61 TCTGCTGCGC CTCGGGTGTC TTTTGCGGCG GTGGGTCGCC GCCGGGAGAA GCGTGAGGGG
 121 ACAGATTTGT GACCGGCGCG GTTTTTGTCA GCTTACTCCG GCCAAAAAAG AACTGCACCT
 181 CTGGAGCGGA CTTATTTACC AAGCATTGGA GGAATATCGT AGGTAAAAAT GCCTATTGGA
 241 TCCAAAGAGA GGCCAACATT TTTTGAAATT TTTAAGCACA CGCTGCAACAA AGCAGATTTA
 301 GGACCAATAA GTCTTAATTG GTTTGAAGAA CTTTCTTCAG AAGCTCCACC CTATAATTCT
 361 GAACCTGCAG AAGAATCTGA ACATAAAAAC AACAATTACG AACCAAACCT ATTTAAAACT
 421 CCACAAAGGA AACCATCTTA TAATCAGCTG GCTTCAACTC AATAATATT CAAAGAGCAA
 481 GGGCTGACTC TGCCGCTGTA CCAATCTCCT GTAAAAGAAT TAGATAAATT CAAATTAGAC
 541 TTAGGAAGGA ATGTTCCCAA TAGTAGACAT AAAAGTCTTC GCACAGTGAA AACTAAAATG
 601 GATCAAGCAG ATGATGTTTC CTGTCCACTT CTAAATTCTT GTCTTAGTGA AAGTCCTGTT
 661 GTTCTACAAT GTACACATGT AACACCACAA AGAGATAAGT CAGTGGTATG TGGGAGTTTG
 721 TTTCATACAC CAAAGTTTGT GAAGGGTCGT CAGACACCAA ACATATTTC TGAAAGTCTA
 781 GGAGCTGAGG TGGATCCTGA TATGTCTTGG TCAAGTTCTT TAGCTACACC ACCCACCCTT
 841 AGTTCTACTG TGCTCATAGT CAGAAATGAA GAAGCATCTG AAACTGTATT TCCTCATGAT
 901 ACTACTGCTA ATGTGAAAAG CTATTTTCC AATCATGATG AAAGTCTGAA GAAAAATGAT
 961 AGATTTATCG CTTCTGTGAC AGACAGTGAA AACACAAATC AAAGAGAAGC TGCAAGTCAT
1021 GGATTTGGAA AAACATCAGG GAATTCATTT AAAGTAAATA GCTGCAAAGA CCACATTGGA
1081 AAGTCAATGC CAAATGTCCT AGAAGATGAA GTATATGAAA CAGTTGTAGA TACCTCTGAA
1141 GAAGATAGTT TTTCATTATG TTTTTCTAAA TGTAGAACAA AAAATCTACA AAAAGTAAGA
1201 ACTAGCAAGA CTAGGAAAAA AATTTTCCAT GAAGCAAACG CTGATGAATG TGAAAAATCT
1261 AAAAACCAAG TGAAAGAAAA ATACTCATTT GTATCTGAAG TGGAACCAAA TGATACTGAT
1321 CCATTAGATT CAAATGTAGC ACATCAGAAG CCCTTTGAGA GTGGAAGTGA CAAAATCTCC
1381 AAGGAAGTTG TACCGTCTTT GGCCTGTGAA TGGTCTCAAC TAACCCTTTC AGGTCTAAAT
1441 GGAGCCCAGA TGGAGAAAAT ACCCCTATTG CATATTTCTT CATGTGACCA AAATATTTCA
1501 GAAAAAGACC TATTAGACAC AGAGAACAAA AGAAGAAAG ATTTTCTTAC TTCAGAGAAT
1561 TCTTTGCCAC GTATTTCTAG CCTACCAAAA TCAGAGAAGC CATTAAATGA GGAAACAGTG
1621 GTAAATAAGA GAGATGAAGA GCAGCATCTT GAATCTCATA CAGACTGCAT TCTTGCAGTA
1681 AAGCAGGCAA TATCTGGAAC TTCTCCAGTG GCTTCTTCAT TTCAGGGTAT CAAAAAGTCT
1741 ATATTCAGAA TAAGAGAATC ACCTAAAGAG ACTTTCAATG CAAGTTTTTC AGGTCATATG
1801 ACTGATCCAA ACTTTAAAAA AGAAACTGAA GCCTCTGAAA GTGGACTGGA ATACACATACT
1861 GTTTGCTCAC AGAAGGAGGA CTCCTTATGT CCAAATTTAA TTGATAATGG AAGCTGGCCA
1921 GCCACCACCA CACAGAATTC TGTAGCTTTG AAGAATGCAG GTTTAATATC CACTTTGAAA
1981 AAGAAAACAA ATAAGTTTAT TTATGCTATA CATGATGAAA CATCTTATAA AGGAAAAAAA
2041 ATACCGAAAG ACCAAAAATC AGAACTAATT AACTGTTCAG CCCAGTTTGA AGCAAATGCT
2101 TTTGAAGCAC CACTTACATT TGCAAATGCT GATTCAGGTT TATTGCATTC TTCTGTGAAA
2161 AGAAGCTGTT CACAGAATGA TTCTGAAGAA CCAACTTTGT CCTTAACTAG CTCTTTTGGG
2221 ACAATTCTGA GGAAATGTTC TAGAAATGAA ACATGTTCTA ATAATACAGT AATCTCTCAG
2281 GATCTTGATT ATAAAGAAGC AAAATGTAAT AAGGAAAAAC TACAGTTATT TATTACCCCA
2341 GAAGCTGATT CTCTGTCATG CCTGCAGGAA GGACAGTGTG AAAATGATCC AAAAAGCAAA
2401 AAAGTTTCAG ATATAAAAGA GAGGTCTTG GCTGCAGCAT GTCACCCAGT ACAACATTCA
2461 AAAGTGGAAT ACAGTGATAC TGACTTTCAA TCCCAGAAAA GTCTTTTATA TGATCATGAA
2521 AATGCCAGCA CTCTTATTTT AACTCCTACT TCCAAGGATG TTCTGTCAAA CCTAGTCATG
2581 ATTTCTAGAG GCAAAGAATC ATACAAAATG TCAGACAAGC TCAAGGTAA CAATTATGAA
2641 TCTGATGTTG AATTAACCAA AAATATTCCC ATGGAAAAGA ATCAAGATGT ATGTGCTTTA
2701 AATGAAAATT ATAAAACGT TGAGCTGTTG CCACCTGAAA ATACATGAG AGTAGCATCA
2761 CCTTCAAGAA AGGTACAATT CAACCAAAAC ACAAATCTAA GAGTAATCCA AAAAAATCAA
2821 GAAGAAACTA CTTCAATTTC AAAAATAACT GTCAATCCAG ACTCTGAAGA ACTTTTCTCA
2881 GACAATGAGA ATAATTTGT CTTCCAAGTA GCTAATGAAA GGAATAATCT TGCTTTAGGA
2941 AATACTAAGG AACTTCATGA ACAGACTTG ACTTGTGTAA ACGAACCCAT TTTCAAGAAC
3001 TCTACCATGG TTTTATATGG AGACACAGGT GATAAACAAG CAACCCAAGT GTCAATTAAA
3061 AAAGATTTGG TTTATGTTCT TGCAGAGGAG AACAAAAATA GTGTAAAGCA GCATATAAAA
3121 ATGACTCTAG GTCAAGATTT AAAATCGGAC ATCTCCTTGA ATATAGATAA AATACCAGAA
3181 AAAAATAATG ATTACATGAA CAAATGGGCA GGACTCTTAG GTCCAATTTC AAATCACAGT
3241 TTTGGAGGTA GCTTCAGAAC AGCTTCAAAT AAGGAAATCA AGCTCTCTGA ACATAACATT
```

FIG. 3A

```
3301 AAGAAGAGCA AAATGTTCTT CAAAGATATT GAAGAACAAT ATCCTACTAG TTTAGCTTGT
3361 GTTGAAATTG TAAATACCTT GGCATTAGAT AATCAAAAGA AACTGAGCAA GCCTCAGTCA
3421 ATTAATACTG TATCTGCACA TTTACAGAGT AGTGTAGTTG TTTCTGATTG TAAAAATAGT
3481 CATATAACCC CTCAGATGTT ATTTTCCAAG CAGGATTTTA ATTCAAACCA TAATTTAACA
3541 CCTAGCCAAA AGGCAGAAAT TACAGAACTT TCTACTATAT TAGAAGAATC AGGAAGTCAG
3601 TTTGAATTTA CTCAGTTTAG AAAACCAAGC TACATATTGC AGAAGAGTAC ATTTGAAGTG
3661 CCTGAAAACC AGATGACTAT CTTAAAGACC ACTTCTGAGG AATGCAGAGA TGCTGATCTT
3721 CATGTCATAA TGAATGCCCC ATCGATTGGT CAGGTAGACA GCAGCAAGCA ATTTGAAGGT
3781 ACAGTTGAAA TTAAACGGAA GTTTGCTGGC CTGTTGAAAA ATGACTGTAA CAAAAGTGCT
3841 TCTGGTTATT TAACAGATGA AAATGAAGTG GGGTTTAGGG GCTTTTATTC TGCTCATGGC
3901 ACAAAACTGA ATGTTCTAC TGAAGCTCTG CAAAAAGCTG TGAAACTGTT TAGTGATATT
3961 GAGAATATTA GTGAGGAAAC TTCTGCAGAG GTACATCCAA TAAGTTTATC TTCAAGTAAA
4021 TGTCATGATT CTGTTGTTTC AATGTTTAAG ATAGAAAATC ATAATGATAA AACTGTAAGT
4081 GAAAAAAATA ATAAATGCCA ACTGATATTA CAAAATAATA TTGAAATGAC TACTGGCACT
4141 TTTGTTGAAG AAATTACTGA AAATTACAAG AGAAATACTG AAAATGAAGA TAACAAATAT
4201 ACTGCTGCCA GTAGAAATTC TCATAACTTA GAATTTGATG GCAGTGATTC AAGTAAAAAT
4261 GATACTGTTT GTATTCATAA AGATGAAACG GACTTGCTAT TTACTGATCA GCACAACATA
4321 TGTCTTAAAT TATCTGGCCA GTTTATGAAG GAGGGAAACA CTCAGATTAA AGAAGATTTG
4381 TCAGATTTAA CTTTTTTGGA AGTTGCGAAA GCTCAAGAAG CATGTCATGG TAATACTTCA
4441 AATAAAGAAC AGTTAACTGC TACTAAAACG GAGCAAAATA TAAAAGATTT TGAGACTTCT
4501 GATACATTTT TTCAGACTGC AAGTGGGAAA AATATTAGTG TCGCCAAAGA GTCATTTAAT
4561 AAAATTGTAA ATTTCTTTGA TCAGAAACCA GAAGAATTGC ATAACTTTTC CTTAAATTCT
4621 GAATTACATT CTGACATAAG AAAGAACAAA ATGGACATTC TAAGTTATGA GGAAACAGAC
4681 ATAGTTAAAC ACAAAATACT GAAAGAAAGT GTCCCAGTTG GTACTGGAAA TCAACTAGTG
4741 ACCTTCCAGG GACAACCCGA ACGTGATGAA AAGATCAAAG AACCTACTCT GTTGGGTTTT
4801 CATACAGCTA GCGGGAAAAA AGTTAAAATT GCAAAGGAAT CTTTGGACAA AGTGAAAAAC
4861 CTTTTTGATG AAAAAGAGCA AGGTACTAGT GAAATCACCA GTTTTAGCCA TCAATGGGCA
4921 AAGACCCTAA AGTACAGAGA GGCCTGTAAA GACCTTGAAT TAGCATGTGA GACCATTGAG
4981 ATCACAGCTG CCCCAAAGTG TAAAGAAATG CAGAATTCTC TCAATAATGA TAAAAACCTT
5041 GTTTCTATTG AGACTGTGGT GCCACCTAAG CTCTTAAGTG ATAATTTATG TAGACAAACT
5101 GAAAATCTCA AAACATCAAA AGTATCTTT TTGAAAGTTA AGTACATGA AAATGTAGAA
5161 AAAGAAACAG CAAAAAGTCC TGCAACTTGT TACACAAATC AGTCCCCTTA TTCAGTCATT
5221 GAAAATTCAG CCTTAGCTTT TTACACAAGT TGTAGTAGAA AAACTTCTGT GAGTCAGACT
5281 TCATTACTTG AAGCAAAAAA ATGGCTTAGA GAAGGAATAT TTGATGGTCA ACCAGAAAGA
5341 ATAAATACTG CAGATTATGT AGGAAATTAT TTGTATGAAA ATAATTCAAA CAGTACTATA
5401 GCTGAAAATG ACAAAAATCA TCTCTCCGAA AAACAAGATA CTTATTTAAG TAACAGTAGC
5461 ATGTCTAACA GCTATTCCTA CCATTCTGAT GAGGTATATA ATGATTCAGG ATATCTCTCA
5521 AAAAATAAAC TTGATTCTGG TATTGAGCCA GTATTGAAGA ATGTTGAAGA TCAAAAAAAC
5581 ACTAGTTTTT CCAAAGTAAT ATCCAATGTA AAAGATGCAA ATGCATACCC ACAAACTGTA
5641 AATGAAGATA TTTGCGTTGA GGAACTTGTG ACTAGCTCTT CACCCTGCAA AAATAAAAAT
5701 GCAGCCATTA AATTGTCCAT ATCTAATAGT AATAATTTTG AGGTAGGGCC ACCTGCATTT
5761 AGGATAGCCA GTGGTAAAAT CGTTTGTGTT TCACATGAAA CAATTAAAAA AGTGAAAGAC
5821 ATATTTACAG ACAGTTTCAG TAAAGTAATT AAGGAAAACA ACGAGAATAA ATCAAAAATT
5881 TGCCAAACGA AAATTATGGC AGGTTGTTAC GAGGCATTGG ATGATTCAGA GGATATTCTT
5941 CATAACTCTC TAGATAATGA TGAATGTAGC ACGCATTCAC ATAAGGTTTT TGCTGACATT
6001 CAGAGTGAAG AAATTTTACA ACATAACCAA AATATGTCTG GATTGGAGAA AGTTTCTAAA
6061 ATATCACCTT GTGATGTTAG TTTGGAAACT TCAGATATAT GTAAATGTAG TATAGGGAAG
6121 CTTCATAAGT CAGTCTCATC TGCAAATACT TGTGGGATTT TTAGCACAGC AAGTGGAAAA
6181 TCTGTCCAGG TATCAGATGC TTCATTACAA AACGCAAGAC AAGTGTTTTC TGAAATAGAA
6241 GATAGTACCA AGCAAGTCTT TTCCAAAGTA TTGTTTAAAA GTAACGAACA TTCAGACCAG
6301 CTCACAAGAG AAGAAAATAC TGCTATAGCT ACTCCAGAAC ATTTAATATC CCAAAAAGGC
6361 TTTTCATATA ATGTGGTAAA TTCATCTGCT TTCTCTGGAT TTAGTACAGC AAGTGGAAAG
6421 CAAGTTTCCA TTTTAGAAAG TTCCTTACAC AAAGTTAAGG GAGTGTTAGA GGAATTTGAT
6481 TTAATCAGAA CTGAGCATAG TCTTCACTAT TCACCTACGT CTAGACAAAA TGTATCAAAA
```

FIG. 3B

```
6541 ATACTTCCTC GTGTTGATAA GAGAAACCCA GAGCACTGTG TAAACTCAGA AATGGAAAAA
6601 ACCTGCAGTA AAGAATTTAA ATTATCAAAT AACTTAAATG TTGAAGGTGG TTCTTCAGAA
6661 AATAATCACT CTATTAAAGT TTCTCCATAT CTCTCTCAAT TTCAACAAGA CAAACAACAG
6721 TTGGTATTAG GAACCAAAGT CTCACTTGTT GAGAACATTC ATGTTTTGGG AAAAGAACAG
6781 GCTTCACCTA AAAACGTAAA AATGGAAATT GGTAAAACTG AAACTTTTTC TGATGTTCCT
6841 GTGAAAACAA ATATAGAAGT TTGTTCTACT TACTCCAAAG ATTCAGAAAA CTACTTTGAA
6901 ACAGAAGCAG TAGAAATTGC TAAAGCTTTT ATGGAAGATG ATGAACTGAC AGATTCTAAA
6961 CTGCCAAGTC ATGCCACACA TTCTCTTTTT ACATGTCCCG AAAATGAGGA AATGGTTTTG
7021 TCAAATTCAA GAATTGGAAA AGAAGAGGA GAGCCCCTTA TCTTAGTGGG AGAACCCTCA
7081 ATCAAAAGAA ACTTATTAAA TGAATTTGAC AGGATAATAG AAAATCAAGA AAAATCCTTA
7141 AAGCTTCAA AAAGCACTCC AGATGGCACA ATAAAAGATC GAAGATTGTT TATGCATCAT
7201 GTTTCTTTAG AGCCGATTAC CTGTGTACCC TTTCGCACAA CTAAGGAACG TCAAGAGATA
7261 CAGAATCCAA ATTTTACCGC ACCTGGTCAA GAATTTCTGT CTAAATCTCA TTTGTATGAA
7321 CATCTGACTT TGGAAAAATC TTCAAGCAAT TTAGCAGTTT CAGGACATCC ATTTTATCAA
7381 GTTTCTGCTA CAAGAAATGA AAAAATGAGA CACTTGATTA CTACAGGCAG ACCAACCAAA
7441 GTCTTTGTTC CACCTTTTAA AACTAAATCA CATTTTCACA GAGTTGAACA GTGTGTTAGG
7501 AATATTAACT TGGAGGAAAA CAGACAAAAG CAAAACATTG ATGGACATGG CTCTGATGAT
7561 AGTAAAAATA AGATTAATGA CAATGAGATT CATCAGTTTA ACAAAAACAA CTCCAATCAA
7621 GCAGCAGCTG TAACTTTCAC AAAGTGTGAA GAAGAACCTT TAGATTTAAT TACAAGTCTT
7681 CAGAATGCCA GAGATATACA GGATATGCGA ATTAAGAAGA AACAAAGGCA ACGCGTCTTT
7741 CCACAGCCAG GCAGTCTGTA TCTTGCAAAA ACATCCACTC TGCCTCGAAT CTCTCTGAAA
7801 GCAGCAGTAG GAGGCCAAGT TCCCTCTGCG TGTTCTCATA ACAGCTGTA TACGTATGGC
7861 GTTTCTAAAC ATTGCATAAA AATTAACAGC AAAAATGCAG AGTCTTTTCA GTTTCACACT
7921 GAAGATTATT TTGGTAAGGA AAGTTTATGG ACTGGAAAAG AATACAGTT GGCTGATGGT
7981 GGATGGCTCA TACCCTCCAA TGATGGAAAG GCTGGAAAAG AAGAATTTTA TAGGGCTCTG
8041 TGTGACACTC CAGGTGTGGA TCCAAAGCTT ATTTCTAGAA TTTGGGTTTA TAATCACTAT
8101 AGATGGATCA TATGGAAACT GGCAGCTATG GAATGTGCCT TTCCTAAGGA ATTTGCTAAT
8161 AGATGCCTAA GCCCAGAAAG GGTGCTTCTT CAACTAAAAT ACAGATATGA TACGGAAATT
8221 GATAGAAGCA GAAGATCGGC TATAAAAAAG ATAATGGAAA GGGATGACAC AGCTGCAAAA
8281 ACACTTGTTC TCTGTGTTTC TGACATAATT TCATTGAGCG CAAATATATC TGAAACTTCT
8341 AGCAATAAAA CTAGTAGTGC AGATACCCAA AAAGTGGCCA TTATTGAACT TACAGATGGG
8401 TGGTATGCTG TTAAGGCCCA GTTAGATCCT CCCCTCTTAG CTGTCTTAAA GAATGGCAGA
8461 CTGACAGTTG GTCAGAAGAT TATTCTTCAT GGAGCAGAAC TGGTGGGCTC TCCTGATGCC
8521 TGTACACCTC TTGAAGCCCC AGAATCTCTT ATGTTAAAGA TTTCTGCTAA CAGTACTCGG
8581 CCTGCTCGCT GGTATACCAA ACTTGGATTC TTTCCTGACC CTAGACCTTT TCCTCTGCCC
8641 TTATCATCGC TTTTCAGTGA TGGAGGAAAT GTTGGTTGTG TTGATGTAAT TATTCAAAGA
8701 GCATACCCTA TACAGTGGAT GGAGAAGACA TCATCTGGAT TATACATATT TCGCAATGAA
8761 AGAGAGGAAG AAAAGGAAGC AGCAAAATAT GTGGAGGCCC AACAAAAGAG ACTAGAAGCC
8821 TTATTCACTA AAATTCAGGA GGAATTTGAA GAACATGAAG AAAACACAAC AAAACCATAT
8881 TTACCATCAC GTGCACTAAC AAGACAGCAA GTTCGTGCTT TGCAAGATGG TGCAGAGCTT
8941 TATGAAGCAG TGAAGAATGC AGCAGACCCA GCTTACCTTG AGGGTTATTT CAGTGAAGAG
9001 CAGTTAAGAG CCTTGAATAA TCACAGGCAA ATGTTAATG ATAAGAAACA AGCTCAGATC
9061 CAGTTGGAAA TTAGGAAGGC CATGGAATCT GCTGAACAAA GGAACAAGG TTTATCAAGG
9121 GATGTCACAA CCGTGTGGAA GTTGCGTATT GTAAGCTATT CAAAAAAAGA AAAAGATTCA
9181 GTTATACTGA GTATTTGGCG TCCATCATCA GATTTATATT CTCTGTTAAC AGAAGGAAAG
9241 AGATACAGAA TTTATCATCT TGCAACTTCA AAATCTAAAA GTAAATCTGA AAGAGCTAAC
9301 ATACAGTTAG CAGCGACAAA AAAAACTCAG TATCAACAAC TACCGGTTTC AGATGAAATT
9361 TTATTTCAGA TTTACCAGCC ACGGGAGCCC CTTCACTTCA GCAAATTTTT AGATCCAGAC
9421 TTTCAGCCAT CTTGTTCTGA GGTGGACCTA ATAGGATTTG TCGTTTCTGT TGTGAAAAAA
9481 ACAGGACTTG CCCCTTTCGT CTATTTGTCA GACGAATGTT ACAATTTACT GGCAATAAAG
9541 TTTTGGATAG ACCTTAATGA GGACATTATT AAGCCTCATA TGTTAATTGC TGCAAGCAAC
9601 CTCCAGTGGC GACCAGAATC CAAATCAGGC CTTCTTACTT TATTTGCTGG AGATTTTCT
9661 GTGTTTTCTG CTAGTCCAAA AGAGGGCCAC TTTCAAGAGA CATTCAACAA AATGAAAAAT
9721 ACTGTTGAGA ATATTGACAT ACTTTGCAAT GAAGCAGAAA ACAAGCTTAT GCATATACTG
```

FIG. 3C

```
 9781 CATGCAAATG ATCCCAAGTG GTCCACCCCA ACTAAAGACT GTACTTCAGG GCCGTACACT
 9841 GCTCAAATCA TTCCTGGTAC AGGAAACAAG CTTCTGATGT CTTCTCCTAA TTGTGAGATA
 9901 TATTATCAAA GTCCTTTATC ACTTTGTATG GCCAAAAGGA AGTCTGTTTC CACACCTGTC
 9961 TCAGCCCAGA TGACTTCAAA GTCTTGTAAA GGGGAGAAAG AGATTGATGA CCAAAAGAAC
10021 TGCAAAAAGA GAAGAGCCTT GGATTTCTTG AGTAGACTGC CTTTACCTCC ACCTGTTAGT
10081 CCCATTTGTA CATTTGTTTC TCCGGCTGCA CAGAAGGCAT TTCAGCCACC AAGGAGTTGT
10141 GGCACCAAAT ACGAAACACC CATAAAGAAA AAGAACTGA ATTCTCCTCA GATGACTCCA
10201 TTTAAAAAAT TCAATGAAAT TTCTCTTTTG GAAAGTAATT CAATAGCTGA CGAAGAACTT
10261 GCATTGATAA ATACCCAAGC TCTTTTGTCT GGTTCAACAG GAGAAAAACA ATTTATATCT
10321 GTCAGTGAAT CCACTAGGAC TGCTCCCACC AGTTCAGAAG ATTATCTCAG ACTGAAACGA
10381 CGTTGTACTA CATCTCTGAT CAAAGAACAG GAGAGTTCCC AGGCCAGTAC GGAAGAATGT
10441 GAGAAAAATA AGCAGGACAC AATTACAACT AAAAAATATA TCTAAGCATT TGCAAAGGCG
10501 ACAATAAATT ATTGACGCTT AACCTTTCCA GTTTATAAGA CTGGAATATA ATTTCAAACC
10561 ACACATTAGT ACTTATGTTG CACAATGAGA AAAGAAATTA GTTTCAAATT TACCTCAGCG
10621 TTTGTGTATC GGGCAAAAAT CGTTTTGCCC GATTCCGTAT TGGTATACTT TTGCTTCAGT
10681 TGCATATCTT AAAACTAAAT GTAATTTATT AACTAATCAA GAAAAACATC TTTGGCTGAG
10741 CTCGGTGGCT CATGCCTGTA ATCCCAACAC TTTGAGAAGC TGAGGTGGGA GGAGTGCTTG
10801 AGGCCAGGAG TTCAAGACCA GCCTGGGCAA CATAGGGAGA CCCCCATCTT TACGAAGAAA
10861 AAAAAAAAGG GGAAAAGAAA ATCTTTTAAA TCTTTGGATT TGATCACTAC AAGTATTATT
10921 TTACAAGTGA AATAAACATA CCATTTTCTT TTAGATTGTG TCATTAAATG GAATGAGGTC
10981 TCTTAGTACA GTTATTTGA TGCAGATAAT TCCTTTTAGT TTAGCTACTA TTTTAGGGGA
11041 TTTTTTTTAG AGGTAACTCA CTATGAAATA GTTCTCCTTA ATGCAAATAT GTTGGTTCTG
11101 CTATAGTTCC ATCCTGTTCA AAAGTCAGGA TGAATATGAA GAGTGGTGTT TCCTTTTGAG
11161 CAATTCTTCA TCCTTAAGTC AGCATGATTA TAAGAAAAAT AGAACCCTCA GTGTAACTCT
11221 AATTCCTTTT TACTATTCCA GTGTGATCTC TGAAATTAAA TTACTTCAAC TAAAAATTCA
11281 AATACTTTAA ATCAGAAGAT TCATAGTTA ATTTATTTTT TTTTTCAACA AAATGGTCAT
11341 CCAAACTCAA ACTTGAGAAA ATATCTTGCT TTCAAATTGA CACTA
```

FIG. 3D

SEQUENCE LISTING (1) GENERAL INFORMATION:

(iii) NUMBER OF SEQUENCES: 124

(2) INFORMATION FOR SEQ ID NO:1:

(i) SEQUENCE CHARACTERISTICS:
       (A) LENGTH: 11385 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: Homo sapiens (ix) FEATURE:
       (A) NAME/KEY: CDS
       (B) LOCATION: 229..10482

(xi) SEQUENCE DESCRIPTION: SEQ ID NO:1:

```
GGTGGCGCGA GCTTCTGAAA CTAGGCGGCA GAGGCGGAGC CGCTGTGGCA CTGCTGCGCC        60

TCTGCTGCGC CTCGGGTGTC TTTTGCGGCG GTGGGTCGCC GCCGGGAGAA GCGTGAGGGG       120

ACAGATTTGT GACCGGCGCG GTTTTTGTCA GCTTACTCCG GCCAAAAAAG AACTGCACCT       180

CTGGAGCGGA CTTATTTACC AAGCATTGGA GGAATATCGT AGGTAAAA ATG CCT ATT        237
                                                    Met Pro Ile
                                                     1

GGA TCC AAA GAG AGG CCA ACA TTT TTT GAA ATT TTT AAG ACA CGC TGC         285
Gly Ser Lys Glu Arg Pro Thr Phe Phe Glu Ile Phe Lys Thr Arg Cys
  5                  10                  15

AAC AAA GCA GAT TTA GGA CCA ATA AGT CTT AAT TGG TTT GAA GAA CTT         333
Asn Lys Ala Asp Leu Gly Pro Ile Ser Leu Asn Trp Phe Glu Glu Leu
 20                  25                  30                  35

TCT TCA GAA GCT CCA CCC TAT AAT TCT GAA CCT GCA GAA GAA TCT GAA         381
Ser Ser Glu Ala Pro Pro Tyr Asn Ser Glu Pro Ala Glu Glu Ser Glu
                 40                  45                  50

CAT AAA AAC AAC AAT TAC GAA CCA AAC CTA TTT AAA ACT CCA CAA AGG         429
His Lys Asn Asn Asn Tyr Glu Pro Asn Leu Phe Lys Thr Pro Gln Arg
             55                  60                  65

AAA CCA TCT TAT AAT CAG CTG GCT TCA ACT CCA ATA ATA TTC AAA GAG         477
Lys Pro Ser Tyr Asn Gln Leu Ala Ser Thr Pro Ile Ile Phe Lys Glu
         70                  75                  80

CAA GGG CTG ACT CTG CCG CTG TAC CAA TCT CCT GTA AAA GAA TTA GAT         525
Gln Gly Leu Thr Leu Pro Leu Tyr Gln Ser Pro Val Lys Glu Leu Asp
     85                  90                  95

AAA TTC AAA TTA GAC TTA GGA AGG AAT GTT CCC AAT AGT AGA CAT AAA         573
Lys Phe Lys Leu Asp Leu Gly Arg Asn Val Pro Asn Ser Arg His Lys
100                 105                 110                 115
```

```
AGT CTT CGC ACA GTG AAA ACT AAA ATG GAT CAA GCA GAT GAT GTT TCC      621
Ser Leu Arg Thr Val Lys Thr Lys Met Asp Gln Ala Asp Asp Val Ser
            120             125             130

TGT CCA CTT CTA AAT TCT TGT CTT AGT GAA AGT CCT GTT GTT CTA CAA      669
Cys Pro Leu Leu Asn Ser Cys Leu Ser Glu Ser Pro Val Val Leu Gln
            135             140             145

TGT ACA CAT GTA ACA CCA CAA AGA GAT AAG TCA GTG GTA TGT GGG AGT      717
Cys Thr His Val Thr Pro Gln Arg Asp Lys Ser Val Val Cys Gly Ser
            150             155             160

TTG TTT CAT ACA CCA AAG TTT GTG AAG GGT CGT CAG ACA CCA AAA CAT      765
Leu Phe His Thr Pro Lys Phe Val Lys Gly Arg Gln Thr Pro Lys His
            165             170             175

ATT TCT GAA AGT CTA GGA GCT GAG GTG GAT CCT GAT ATG TCT TGG TCA      813
Ile Ser Glu Ser Leu Gly Ala Glu Val Asp Pro Asp Met Ser Trp Ser
180             185             190             195

AGT TCT TTA GCT ACA CCA CCC ACC CTT AGT TCT ACT GTG CTC ATA GTC      861
Ser Ser Leu Ala Thr Pro Pro Thr Leu Ser Ser Thr Val Leu Ile Val
                200             205             210

AGA AAT GAA GAA GCA TCT GAA ACT GTA TTT CCT CAT GAT ACT ACT GCT      909
Arg Asn Glu Glu Ala Ser Glu Thr Val Phe Pro His Asp Thr Thr Ala
                215             220             225

AAT GTG AAA AGC TAT TTT TCC AAT CAT GAT GAA AGT CTG AAG AAA AAT      957
Asn Val Lys Ser Tyr Phe Ser Asn His Asp Glu Ser Leu Lys Lys Asn
                230             235             240

GAT AGA TTT ATC GCT TCT GTG ACA GAC AGT GAA AAC ACA AAT CAA AGA     1005
Asp Arg Phe Ile Ala Ser Val Thr Asp Ser Glu Asn Thr Asn Gln Arg
            245             250             255

GAA GCT GCA AGT CAT GGA TTT GGA AAA ACA TCA GGG AAT TCA TTT AAA     1053
Glu Ala Ala Ser His Gly Phe Gly Lys Thr Ser Gly Asn Ser Phe Lys
260             265             270             275

GTA AAT AGC TGC AAA GAC CAC ATT GGA AAG TCA ATG CCA AAT GTC CTA     1101
Val Asn Ser Cys Lys Asp His Ile Gly Lys Ser Met Pro Asn Val Leu
                280             285             290

GAA GAT GAA GTA TAT GAA ACA GTT GTA GAT ACC TCT GAA GAA GAT AGT     1149
Glu Asp Glu Val Tyr Glu Thr Val Val Asp Thr Ser Glu Glu Asp Ser
                295             300             305

TTT TCA TTA TGT TTT TCT AAA TGT AGA ACA AAA AAT CTA CAA AAA GTA     1197
Phe Ser Leu Cys Phe Ser Lys Cys Arg Thr Lys Asn Leu Gln Lys Val
            310             315             320

AGA ACT AGC AAG ACT AGG AAA AAA ATT TTC CAT GAA GCA AAC GCT GAT     1245
Arg Thr Ser Lys Thr Arg Lys Lys Ile Phe His Glu Ala Asn Ala Asp
325             330             335

GAA TGT GAA AAA TCT AAA AAC CAA GTG AAA GAA AAA TAC TCA TTT GTA     1293
Glu Cys Glu Lys Ser Lys Asn Gln Val Lys Glu Lys Tyr Ser Phe Val
340             345             350             355

TCT GAA GTG GAA CCA AAT GAT ACT GAT CCA TTA GAT TCA AAT GTA GCA     1341
Ser Glu Val Glu Pro Asn Asp Thr Asp Pro Leu Asp Ser Asn Val Ala
                360             365             370

CAT CAG AAG CCC TTT GAG AGT GGA AGT GAC AAA ATC TCC AAG GAA GTT     1389
His Gln Lys Pro Phe Glu Ser Gly Ser Asp Lys Ile Ser Lys Glu Val
            375             380             385

GTA CCG TCT TTG GCC TGT GAA TGG TCT CAA CTA ACC CTT TCA GGT CTA     1437
Val Pro Ser Leu Ala Cys Glu Trp Ser Gln Leu Thr Leu Ser Gly Leu
            390             395             400

AAT GGA GCC CAG ATG GAG AAA ATA CCC TTA TTG CAT ATT TCT TCA TGT     1485
Asn Gly Ala Gln Met Glu Lys Ile Pro Leu Leu His Ile Ser Ser Cys
            405             410             415

GAC CAA AAT ATT TCA GAA AAA GAC CTA TTA GAC ACA GAG AAC AAA AGA     1533
Asp Gln Asn Ile Ser Glu Lys Asp Leu Leu Asp Thr Glu Asn Lys Arg
420             425             430             435
```

```
AAG AAA GAT TTT CTT ACT TCA GAG AAT TCT TTG CCA CGT ATT TCT AGC    1581
Lys Lys Asp Phe Leu Thr Ser Glu Asn Ser Leu Pro Arg Ile Ser Ser
                440                 445                 450

CTA CCA AAA TCA GAG AAG CCA TTA AAT GAG GAA ACA GTG GTA AAT AAG    1629
Leu Pro Lys Ser Glu Lys Pro Leu Asn Glu Glu Thr Val Val Asn Lys
                455                 460                 465

AGA GAT GAA GAG CAG CAT CTT GAA TCT CAT ACA GAC TGC ATT CTT GCA    1677
Arg Asp Glu Glu Gln His Leu Glu Ser His Thr Asp Cys Ile Leu Ala
                470                 475                 480

GTA AAG CAG GCA ATA TCT GGA ACT TCT CCA GTG GCT TCT TCA TTT CAG    1725
Val Lys Gln Ala Ile Ser Gly Thr Ser Pro Val Ala Ser Ser Phe Gln
                485                 490                 495

GGT ATC AAA AAG TCT ATA TTC AGA ATA AGA GAA TCA CCT AAA GAG ACT    1773
Gly Ile Lys Lys Ser Ile Phe Arg Ile Arg Glu Ser Pro Lys Glu Thr
500                 505                 510                 515

TTC AAT GCA AGT TTT TCA GGT CAT ATG ACT GAT CCA AAC TTT AAA AAA    1821
Phe Asn Ala Ser Phe Ser Gly His Met Thr Asp Pro Asn Phe Lys Lys
                520                 525                 530

GAA ACT GAA GCC TCT GAA AGT GGA CTG GAA ATA CAT ACT GTT TGC TCA    1869
Glu Thr Glu Ala Ser Glu Ser Gly Leu Glu Ile His Thr Val Cys Ser
                535                 540                 545

CAG AAG GAG GAC TCC TTA TGT CCA AAT TTA ATT GAT AAT GGA AGC TGG    1917
Gln Lys Glu Asp Ser Leu Cys Pro Asn Leu Ile Asp Asn Gly Ser Trp
                550                 555                 560

CCA GCC ACC ACC ACA CAG AAT TCT GTA GCT TTG AAG AAT GCA GGT TTA    1965
Pro Ala Thr Thr Thr Gln Asn Ser Val Ala Leu Lys Asn Ala Gly Leu
                565                 570                 575

ATA TCC ACT TTG AAA AAG AAA ACA AAT AAG TTT ATT TAT GCT ATA CAT    2013
Ile Ser Thr Leu Lys Lys Lys Thr Asn Lys Phe Ile Tyr Ala Ile His
580                 585                 590                 595

GAT GAA ACA TCT TAT AAA GGA AAA AAA ATA CCG AAA GAC CAA AAA TCA    2061
Asp Glu Thr Ser Tyr Lys Gly Lys Lys Ile Pro Lys Asp Gln Lys Ser
                600                 605                 610

GAA CTA ATT AAC TGT TCA GCC CAG TTT GAA GCA AAT GCT TTT GAA GCA    2109
Glu Leu Ile Asn Cys Ser Ala Gln Phe Glu Ala Asn Ala Phe Glu Ala
                615                 620                 625

CCA CTT ACA TTT GCA AAT GCT GAT TCA GGT TTA TTG CAT TCT TCT GTG    2157
Pro Leu Thr Phe Ala Asn Ala Asp Ser Gly Leu Leu His Ser Ser Val
                630                 635                 640

AAA AGA AGC TGT TCA CAG AAT GAT TCT GAA GAA CCA ACT TTG TCC TTA    2205
Lys Arg Ser Cys Ser Gln Asn Asp Ser Glu Glu Pro Thr Leu Ser Leu
                645                 650                 655

ACT AGC TCT TTT GGG ACA ATT CTG AGG AAA TGT TCT AGA AAT GAA ACA    2253
Thr Ser Ser Phe Gly Thr Ile Leu Arg Lys Cys Ser Arg Asn Glu Thr
660                 665                 670                 675

TGT TCT AAT AAT ACA GTA ATC TCT CAG GAT CTT GAT TAT AAA GAA GCA    2301
Cys Ser Asn Asn Thr Val Ile Ser Gln Asp Leu Asp Tyr Lys Glu Ala
                680                 685                 690

AAA TGT AAT AAG GAA AAA CTA CAG TTA TTT ATT ACC CCA GAA GCT GAT    2349
Lys Cys Asn Lys Glu Lys Leu Gln Leu Phe Ile Thr Pro Glu Ala Asp
                695                 700                 705

TCT CTG TCA TGC CTG CAG GAA GGA CAG TGT GAA AAT GAT CCA AAA AGC    2397
Ser Leu Ser Cys Leu Gln Glu Gly Gln Cys Glu Asn Asp Pro Lys Ser
                710                 715                 720

AAA AAA GTT TCA GAT ATA AAA GAA GAG GTC TTG GCT GCA GCA TGT CAC    2445
Lys Lys Val Ser Asp Ile Lys Glu Glu Val Leu Ala Ala Ala Cys His
                725                 730                 735

CCA GTA CAA CAT TCA AAA GTG GAA TAC AGT GAT ACT GAC TTT CAA TCC    2493
Pro Val Gln His Ser Lys Val Glu Tyr Ser Asp Thr Asp Phe Gln Ser
```

-continued

| | | | | | | | | | | | | | |
|---|---|---|---|---|---|---|---|---|---|---|---|---|---|
| 740 | | | | | 745 | | | | 750 | | | | 755 |
| CAG | AAA | AGT | CTT | TTA | TAT | GAT | CAT | GAA | AAT | GCC | AGC | ACT | CTT | ATT | TTA | 2541 |
| Gln | Lys | Ser | Leu | Leu | Tyr | Asp | His | Glu | Asn | Ala | Ser | Thr | Leu | Ile | Leu |
| | | | 760 | | | | | 765 | | | | 770 | |

```
740                      745                      750                      755
CAG AAA AGT CTT TTA TAT GAT CAT GAA AAT GCC AGC ACT CTT ATT TTA              2541
Gln Lys Ser Leu Leu Tyr Asp His Glu Asn Ala Ser Thr Leu Ile Leu
            760                 765                 770

ACT CCT ACT TCC AAG GAT GTT CTG TCA AAC CTA GTC ATG ATT TCT AGA              2589
Thr Pro Thr Ser Lys Asp Val Leu Ser Asn Leu Val Met Ile Ser Arg
            775                 780                 785

GGC AAA GAA TCA TAC AAA ATG TCA GAC AAG CTC AAA GGT AAC AAT TAT              2637
Gly Lys Glu Ser Tyr Lys Met Ser Asp Lys Leu Lys Gly Asn Asn Tyr
            790                 795                 800

GAA TCT GAT GTT GAA TTA ACC AAA AAT ATT CCC ATG GAA AAG AAT CAA              2685
Glu Ser Asp Val Glu Leu Thr Lys Asn Ile Pro Met Glu Lys Asn Gln
            805                 810                 815

GAT GTA TGT GCT TTA AAT GAA AAT TAT AAA AAC GTT GAG CTG TTG CCA              2733
Asp Val Cys Ala Leu Asn Glu Asn Tyr Lys Asn Val Glu Leu Leu Pro
820                 825                 830                 835

CCT GAA AAA TAC ATG AGA GTA GCA TCA CCT TCA AGA AAG GTA CAA TTC              2781
Pro Glu Lys Tyr Met Arg Val Ala Ser Pro Ser Arg Lys Val Gln Phe
                840                 845                 850

AAC CAA AAC ACA AAT CTA AGA GTA ATC CAA AAA AAT CAA GAA GAA ACT              2829
Asn Gln Asn Thr Asn Leu Arg Val Ile Gln Lys Asn Gln Glu Glu Thr
                855                 860                 865

ACT TCA ATT TCA AAA ATA ACT GTC AAT CCA GAC TCT GAA GAA CTT TTC              2877
Thr Ser Ile Ser Lys Ile Thr Val Asn Pro Asp Ser Glu Glu Leu Phe
            870                 875                 880

TCA GAC AAT GAG AAT AAT TTT GTC TTC CAA GTA GCT AAT GAA AGG AAT              2925
Ser Asp Asn Glu Asn Asn Phe Val Phe Gln Val Ala Asn Glu Arg Asn
            885                 890                 895

AAT CTT GCT TTA GGA AAT ACT AAG GAA CTT CAT GAA ACA GAC TTG ACT              2973
Asn Leu Ala Leu Gly Asn Thr Lys Glu Leu His Glu Thr Asp Leu Thr
900                 905                 910                 915

TGT GTA AAC GAA CCC ATT TTC AAG AAC TCT ACC ATG GTT TTA TAT GGA              3021
Cys Val Asn Glu Pro Ile Phe Lys Asn Ser Thr Met Val Leu Tyr Gly
                920                 925                 930

GAC ACA GGT GAT AAA CAA GCA ACC CAA GTG TCA ATT AAA AAA GAT TTG              3069
Asp Thr Gly Asp Lys Gln Ala Thr Gln Val Ser Ile Lys Lys Asp Leu
                935                 940                 945

GTT TAT GTT CTT GCA GAG GAG AAC AAA AAT AGT GTA AAG CAG CAT ATA              3117
Val Tyr Val Leu Ala Glu Glu Asn Lys Asn Ser Val Lys Gln His Ile
                950                 955                 960

AAA ATG ACT CTA GGT CAA GAT TTA AAA TCG GAC ATC TCC TTG AAT ATA              3165
Lys Met Thr Leu Gly Gln Asp Leu Lys Ser Asp Ile Ser Leu Asn Ile
            965                 970                 975

GAT AAA ATA CCA GAA AAA AAT AAT GAT TAC ATG AAC AAA TGG GCA GGA              3213
Asp Lys Ile Pro Glu Lys Asn Asn Asp Tyr Met Asn Lys Trp Ala Gly
980                 985                 990                 995

CTC TTA GGT CCA ATT TCA AAT CAC AGT TTT GGA GGT AGC TTC AGA ACA              3261
Leu Leu Gly Pro Ile Ser Asn His Ser Phe Gly Gly Ser Phe Arg Thr
                1000                1005                1010

GCT TCA AAT AAG GAA ATC AAG CTC TCT GAA CAT AAC ATT AAG AAG AGC              3309
Ala Ser Asn Lys Glu Ile Lys Leu Ser Glu His Asn Ile Lys Lys Ser
                1015                1020                1025

AAA ATG TTC TTC AAA GAT ATT GAA GAA CAA TAT CCT ACT AGT TTA GCT              3357
Lys Met Phe Phe Lys Asp Ile Glu Glu Gln Tyr Pro Thr Ser Leu Ala
                1030                1035                1040

TGT GTT GAA ATT GTA AAT ACC TTG GCA TTA GAT AAT CAA AAG AAA CTG              3405
Cys Val Glu Ile Val Asn Thr Leu Ala Leu Asp Asn Gln Lys Lys Leu
                1045                1050                1055

AGC AAG CCT CAG TCA ATT AAT ACT GTA TCT GCA CAT TTA CAG AGT AGT              3453
```

```
Ser Lys Pro Gln Ser Ile Asn Thr Val Ser Ala His Leu Gln Ser Ser
1060                1065                1070                1075

GTA GTT GTT TCT GAT TGT AAA AAT AGT CAT ATA ACC CCT CAG ATG TTA      3501
Val Val Val Ser Asp Cys Lys Asn Ser His Ile Thr Pro Gln Met Leu
                1080                1085                1090

TTT TCC AAG CAG GAT TTT AAT TCA AAC CAT AAT TTA ACA CCT AGC CAA      3549
Phe Ser Lys Gln Asp Phe Asn Ser Asn His Asn Leu Thr Pro Ser Gln
            1095                1100                1105

AAG GCA GAA ATT ACA GAA CTT TCT ACT ATA TTA GAA GAA TCA GGA AGT      3597
Lys Ala Glu Ile Thr Glu Leu Ser Thr Ile Leu Glu Glu Ser Gly Ser
        1110                1115                1120

CAG TTT GAA TTT ACT CAG TTT AGA AAA CCA AGC TAC ATA TTG CAG AAG      3645
Gln Phe Glu Phe Thr Gln Phe Arg Lys Pro Ser Tyr Ile Leu Gln Lys
    1125                1130                1135

AGT ACA TTT GAA GTG CCT GAA AAC CAG ATG ACT ATC TTA AAG ACC ACT      3693
Ser Thr Phe Glu Val Pro Glu Asn Gln Met Thr Ile Leu Lys Thr Thr
1140                1145                1150                1155

TCT GAG GAA TGC AGA GAT GCT GAT CTT CAT GTC ATA ATG AAT GCC CCA      3741
Ser Glu Glu Cys Arg Asp Ala Asp Leu His Val Ile Met Asn Ala Pro
                1160                1165                1170

TCG ATT GGT CAG GTA GAC AGC AGC AAG CAA TTT GAA GGT ACA GTT GAA      3789
Ser Ile Gly Gln Val Asp Ser Ser Lys Gln Phe Glu Gly Thr Val Glu
            1175                1180                1185

ATT AAA CGG AAG TTT GCT GGC CTG TTG AAA AAT GAC TGT AAC AAA AGT      3837
Ile Lys Arg Lys Phe Ala Gly Leu Leu Lys Asn Asp Cys Asn Lys Ser
        1190                1195                1200

GCT TCT GGT TAT TTA ACA GAT GAA AAT GAA GTG GGG TTT AGG GGC TTT      3885
Ala Ser Gly Tyr Leu Thr Asp Glu Asn Glu Val Gly Phe Arg Gly Phe
    1205                1210                1215

TAT TCT GCT CAT GGC ACA AAA CTG AAT GTT TCT ACT GAA GCT CTG CAA      3933
Tyr Ser Ala His Gly Thr Lys Leu Asn Val Ser Thr Glu Ala Leu Gln
1220                1225                1230                1235

AAA GCT GTG AAA CTG TTT AGT GAT ATT GAG AAT ATT AGT GAG GAA ACT      3981
Lys Ala Val Lys Leu Phe Ser Asp Ile Glu Asn Ile Ser Glu Glu Thr
                1240                1245                1250

TCT GCA GAG GTA CAT CCA ATA AGT TTA TCT TCA AGT AAA TGT CAT GAT      4029
Ser Ala Glu Val His Pro Ile Ser Leu Ser Ser Ser Lys Cys His Asp
            1255                1260                1265

TCT GTT GTT TCA ATG TTT AAG ATA GAA AAT CAT AAT GAT AAA ACT GTA      4077
Ser Val Val Ser Met Phe Lys Ile Glu Asn His Asn Asp Lys Thr Val
        1270                1275                1280

AGT GAA AAA AAT AAT AAA TGC CAA CTG ATA TTA CAA AAT AAT ATT GAA      4125
Ser Glu Lys Asn Asn Lys Cys Gln Leu Ile Leu Gln Asn Asn Ile Glu
    1285                1290                1295

ATG ACT ACT GGC ACT TTT GTT GAA GAA ATT ACT GAA AAT TAC AAG AGA      4173
Met Thr Thr Gly Thr Phe Val Glu Glu Ile Thr Glu Asn Tyr Lys Arg
1300                1305                1310                1315

AAT ACT GAA AAT GAA GAT AAC AAA TAT ACT GCT GCC AGT AGA AAT TCT      4221
Asn Thr Glu Asn Glu Asp Asn Lys Tyr Thr Ala Ala Ser Arg Asn Ser
                1320                1325                1330

CAT AAC TTA GAA TTT GAT GGC AGT GAT TCA AGT AAA AAT GAT ACT GTT      4269
His Asn Leu Glu Phe Asp Gly Ser Asp Ser Ser Lys Asn Asp Thr Val
            1335                1340                1345

TGT ATT CAT AAA GAT GAA ACG GAC TTG CTA TTT ACT GAT CAG CAC AAC      4317
Cys Ile His Lys Asp Glu Thr Asp Leu Leu Phe Thr Asp Gln His Asn
        1350                1355                1360

ATA TGT CTT AAA TTA TCT GGC CAG TTT ATG AAG GAG GGA AAC ACT CAG      4365
Ile Cys Leu Lys Leu Ser Gly Gln Phe Met Lys Glu Gly Asn Thr Gln
    1365                1370                1375
```

```
ATT AAA GAA GAT TTG TCA GAT TTA ACT TTT TTG GAA GTT GCG AAA GCT      4413
Ile Lys Glu Asp Leu Ser Asp Leu Thr Phe Leu Glu Val Ala Lys Ala
1380                1385                1390                1395

CAA GAA GCA TGT CAT GGT AAT ACT TCA AAT AAA GAA CAG TTA ACT GCT      4461
Gln Glu Ala Cys His Gly Asn Thr Ser Asn Lys Glu Gln Leu Thr Ala
                1400                1405                1410

ACT AAA ACG GAG CAA AAT ATA AAA GAT TTT GAG ACT TCT GAT ACA TTT      4509
Thr Lys Thr Glu Gln Asn Ile Lys Asp Phe Glu Thr Ser Asp Thr Phe
            1415                1420                1425

TTT CAG ACT GCA AGT GGG AAA AAT ATT AGT GTC GCC AAA GAG TCA TTT      4557
Phe Gln Thr Ala Ser Gly Lys Asn Ile Ser Val Ala Lys Glu Ser Phe
        1430                1435                1440

AAT AAA ATT GTA AAT TTC TTT GAT CAG AAA CCA GAA GAA TTG CAT AAC      4605
Asn Lys Ile Val Asn Phe Phe Asp Gln Lys Pro Glu Glu Leu His Asn
    1445                1450                1455

TTT TCC TTA AAT TCT GAA TTA CAT TCT GAC ATA AGA AAG AAC AAA ATG      4653
Phe Ser Leu Asn Ser Glu Leu His Ser Asp Ile Arg Lys Asn Lys Met
1460                1465                1470                1475

GAC ATT CTA AGT TAT GAG GAA ACA GAC ATA GTT AAA CAC AAA ATA CTG      4701
Asp Ile Leu Ser Tyr Glu Glu Thr Asp Ile Val Lys His Lys Ile Leu
                1480                1485                1490

AAA GAA AGT GTC CCA GTT GGT ACT GGA AAT CAA CTA GTG ACC TTC CAG      4749
Lys Glu Ser Val Pro Val Gly Thr Gly Asn Gln Leu Val Thr Phe Gln
            1495                1500                1505

GGA CAA CCC GAA CGT GAT GAA AAG ATC AAA GAA CCT ACT CTG TTG GGT      4797
Gly Gln Pro Glu Arg Asp Glu Lys Ile Lys Glu Pro Thr Leu Leu Gly
        1510                1515                1520

TTT CAT ACA GCT AGC GGG AAA AAA GTT AAA ATT GCA AAG GAA TCT TTG      4845
Phe His Thr Ala Ser Gly Lys Lys Val Lys Ile Ala Lys Glu Ser Leu
    1525                1530                1535

GAC AAA GTG AAA AAC CTT TTT GAT GAA AAA GAG CAA GGT ACT AGT GAA      4893
Asp Lys Val Lys Asn Leu Phe Asp Glu Lys Glu Gln Gly Thr Ser Glu
1540                1545                1550                1555

ATC ACC AGT TTT AGC CAT CAA TGG GCA AAG ACC CTA AAG TAC AGA GAG      4941
Ile Thr Ser Phe Ser His Gln Trp Ala Lys Thr Leu Lys Tyr Arg Glu
                1560                1565                1570

GCC TGT AAA GAC CTT GAA TTA GCA TGT GAG ACC ATT GAG ATC ACA GCT      4989
Ala Cys Lys Asp Leu Glu Leu Ala Cys Glu Thr Ile Glu Ile Thr Ala
            1575                1580                1585

GCC CCA AAG TGT AAA GAA ATG CAG AAT TCT CTC AAT AAT GAT AAA AAC      5037
Ala Pro Lys Cys Lys Glu Met Gln Asn Ser Leu Asn Asn Asp Lys Asn
        1590                1595                1600

CTT GTT TCT ATT GAG ACT GTG GTG CCA CCT AAG CTC TTA AGT GAT AAT      5085
Leu Val Ser Ile Glu Thr Val Val Pro Pro Lys Leu Leu Ser Asp Asn
    1605                1610                1615

TTA TGT AGA CAA ACT GAA AAT CTC AAA ACA TCA AAA AGT ATC TTT TTG      5133
Leu Cys Arg Gln Thr Glu Asn Leu Lys Thr Ser Lys Ser Ile Phe Leu
1620                1625                1630                1635

AAA GTT AAA GTA CAT GAA AAT GTA GAA AAA GAA ACA GCA AAA AGT CCT      5181
Lys Val Lys Val His Glu Asn Val Glu Lys Glu Thr Ala Lys Ser Pro
                1640                1645                1650

GCA ACT TGT TAC ACA AAT CAG TCC CCT TAT TCA GTC ATT GAA AAT TCA      5229
Ala Thr Cys Tyr Thr Asn Gln Ser Pro Tyr Ser Val Ile Glu Asn Ser
            1655                1660                1665

GCC TTA GCT TTT TAC ACA AGT TGT AGT AGA AAA ACT TCT GTG AGT CAG      5277
Ala Leu Ala Phe Tyr Thr Ser Cys Ser Arg Lys Thr Ser Val Ser Gln
        1670                1675                1680

ACT TCA TTA CTT GAA GCA AAA AAA TGG CTT AGA GAA GGA ATA TTT GAT      5325
Thr Ser Leu Leu Glu Ala Lys Lys Trp Leu Arg Glu Gly Ile Phe Asp
    1685                1690                1695
```

-continued

```
GGT CAA CCA GAA AGA ATA AAT ACT GCA GAT TAT GTA GGA AAT TAT TTG      5373
Gly Gln Pro Glu Arg Ile Asn Thr Ala Asp Tyr Val Gly Asn Tyr Leu
1700            1705                1710                1715

TAT GAA AAT AAT TCA AAC AGT ACT ATA GCT GAA AAT GAC AAA AAT CAT      5421
Tyr Glu Asn Asn Ser Asn Ser Thr Ile Ala Glu Asn Asp Lys Asn His
                1720                1725                1730

CTC TCC GAA AAA CAA GAT ACT TAT TTA AGT AAC AGT AGC ATG TCT AAC      5469
Leu Ser Glu Lys Gln Asp Thr Tyr Leu Ser Asn Ser Ser Met Ser Asn
            1735                1740                1745

AGC TAT TCC TAC CAT TCT GAT GAG GTA TAT AAT GAT TCA GGA TAT CTC      5517
Ser Tyr Ser Tyr His Ser Asp Glu Val Tyr Asn Asp Ser Gly Tyr Leu
        1750                1755                1760

TCA AAA AAT AAA CTT GAT TCT GGT ATT GAG CCA GTA TTG AAG AAT GTT      5565
Ser Lys Asn Lys Leu Asp Ser Gly Ile Glu Pro Val Leu Lys Asn Val
    1765                1770                1775

GAA GAT CAA AAA AAC ACT AGT TTT TCC AAA GTA ATA TCC AAT GTA AAA      5613
Glu Asp Gln Lys Asn Thr Ser Phe Ser Lys Val Ile Ser Asn Val Lys
1780                1785                1790                1795

GAT GCA AAT GCA TAC CCA CAA ACT GTA AAT GAA GAT ATT TGC GTT GAG      5661
Asp Ala Asn Ala Tyr Pro Gln Thr Val Asn Glu Asp Ile Cys Val Glu
                1800                1805                1810

GAA CTT GTG ACT AGC TCT TCA CCC TGC AAA AAT AAA AAT GCA GCC ATT      5709
Glu Leu Val Thr Ser Ser Ser Pro Cys Lys Asn Lys Asn Ala Ala Ile
            1815                1820                1825

AAA TTG TCC ATA TCT AAT AGT AAT AAT TTT GAG GTA GGG CCA CCT GCA      5757
Lys Leu Ser Ile Ser Asn Ser Asn Asn Phe Glu Val Gly Pro Pro Ala
        1830                1835                1840

TTT AGG ATA GCC AGT GGT AAA ATC GTT TGT GTT TCA CAT GAA ACA ATT      5805
Phe Arg Ile Ala Ser Gly Lys Ile Val Cys Val Ser His Glu Thr Ile
    1845                1850                1855

AAA AAA GTG AAA GAC ATA TTT ACA GAC AGT TTC AGT AAA GTA ATT AAG      5853
Lys Lys Val Lys Asp Ile Phe Thr Asp Ser Phe Ser Lys Val Ile Lys
1860                1865                1870                1875

GAA AAC AAC GAG AAT AAA TCA AAA ATT TGC CAA ACG AAA ATT ATG GCA      5901
Glu Asn Asn Glu Asn Lys Ser Lys Ile Cys Gln Thr Lys Ile Met Ala
                1880                1885                1890

GGT TGT TAC GAG GCA TTG GAT GAT TCA GAG GAT ATT CTT CAT AAC TCT      5949
Gly Cys Tyr Glu Ala Leu Asp Asp Ser Glu Asp Ile Leu His Asn Ser
            1895                1900                1905

CTA GAT AAT GAT GAA TGT AGC ACG CAT TCA CAT AAG GTT TTT GCT GAC      5997
Leu Asp Asn Asp Glu Cys Ser Thr His Ser His Lys Val Phe Ala Asp
        1910                1915                1920

ATT CAG AGT GAA GAA ATT TTA CAA CAT AAC CAA AAT ATG TCT GGA TTG      6045
Ile Gln Ser Glu Glu Ile Leu Gln His Asn Gln Asn Met Ser Gly Leu
    1925                1930                1935

GAG AAA GTT TCT AAA ATA TCA CCT TGT GAT GTT AGT TTG GAA ACT TCA      6093
Glu Lys Val Ser Lys Ile Ser Pro Cys Asp Val Ser Leu Glu Thr Ser
1940                1945                1950                1955

GAT ATA TGT AAA TGT AGT ATA GGG AAG CTT CAT AAG TCA GTC TCA TCT      6141
Asp Ile Cys Lys Cys Ser Ile Gly Lys Leu His Lys Ser Val Ser Ser
                1960                1965                1970

GCA AAT ACT TGT GGG ATT TTT AGC ACA GCA AGT GGA AAA TCT GTC CAG      6189
Ala Asn Thr Cys Gly Ile Phe Ser Thr Ala Ser Gly Lys Ser Val Gln
            1975                1980                1985

GTA TCA GAT GCT TCA TTA CAA AAC GCA AGA CAA GTG TTT TCT GAA ATA      6237
Val Ser Asp Ala Ser Leu Gln Asn Ala Arg Gln Val Phe Ser Glu Ile
        1990                1995                2000

GAA GAT AGT ACC AAG CAA GTC TTT TCC AAA GTA TTG TTT AAA AGT AAC      6285
Glu Asp Ser Thr Lys Gln Val Phe Ser Lys Val Leu Phe Lys Ser Asn
```

-continued

```
        2005                2010                2015
GAA CAT TCA GAC CAG CTC ACA AGA GAA GAA AAT ACT GCT ATA CGT ACT         6333
Glu His Ser Asp Gln Leu Thr Arg Glu Glu Asn Thr Ala Ile Arg Thr
2020                2025                2030                2035

CCA GAA CAT TTA ATA TCC CAA AAA GGC TTT TCA TAT AAT GTG GTA AAT         6381
Pro Glu His Leu Ile Ser Gln Lys Gly Phe Ser Tyr Asn Val Val Asn
            2040                2045                2050

TCA TCT GCT TTC TCT GGA TTT AGT ACA GCA AGT GGA AAG CAA GTT TCC         6429
Ser Ser Ala Phe Ser Gly Phe Ser Thr Ala Ser Gly Lys Gln Val Ser
                2055                2060                2065

ATT TTA GAA AGT TCC TTA CAC AAA GTT AAG GGA GTG TTA GAG GAA TTT         6477
Ile Leu Glu Ser Ser Leu His Lys Val Lys Gly Val Leu Glu Glu Phe
            2070                2075                2080

GAT TTA ATC AGA ACT GAG CAT AGT CTT CAC TAT TCA CCT ACG TCT AGA         6525
Asp Leu Ile Arg Thr Glu His Ser Leu His Tyr Ser Pro Thr Ser Arg
            2085                2090                2095

CAA AAT GTA TCA AAA ATA CTT CCT CGT GTT GAT AAG AGA AAC CCA GAG         6573
Gln Asn Val Ser Lys Ile Leu Pro Arg Val Asp Lys Arg Asn Pro Glu
2100                2105                2110                2115

CAC TGT GTA AAC TCA GAA ATG GAA AAA ACC TGC AGT AAA GAA TTT AAA         6621
His Cys Val Asn Ser Glu Met Glu Lys Thr Cys Ser Lys Glu Phe Lys
            2120                2125                2130

TTA TCA AAT AAC TTA AAT GTT GAA GGT GGT TCT TCA GAA AAT AAT CAC         6669
Leu Ser Asn Asn Leu Asn Val Glu Gly Gly Ser Ser Glu Asn Asn His
            2135                2140                2145

TCT ATT AAA GTT TCT CCA TAT CTC TCT CAA TTT CAA CAA GAC AAA CAA         6717
Ser Ile Lys Val Ser Pro Tyr Leu Ser Gln Phe Gln Gln Asp Lys Gln
            2150                2155                2160

CAG TTG GTA TTA GGA ACC AAA GTC TCA CTT GTT GAG AAC ATT CAT GTT         6765
Gln Leu Val Leu Gly Thr Lys Val Ser Leu Val Glu Asn Ile His Val
            2165                2170                2175

TTG GGA AAA GAA CAG GCT TCA CCT AAA AAC GTA AAA ATG GAA ATT GGT         6813
Leu Gly Lys Glu Gln Ala Ser Pro Lys Asn Val Lys Met Glu Ile Gly
2180                2185                2190                2195

AAA ACT GAA ACT TTT TCT GAT GTT CCT GTG AAA ACA AAT ATA GAA GTT         6861
Lys Thr Glu Thr Phe Ser Asp Val Pro Val Lys Thr Asn Ile Glu Val
            2200                2205                2210

TGT TCT ACT TAC TCC AAA GAT TCA GAA AAC TAC TTT GAA ACA GAA GCA         6909
Cys Ser Thr Tyr Ser Lys Asp Ser Glu Asn Tyr Phe Glu Thr Glu Ala
            2215                2220                2225

GTA GAA ATT GCT AAA GCT TTT ATG GAA GAT GAT GAA CTG ACA GAT TCT         6957
Val Glu Ile Ala Lys Ala Phe Met Glu Asp Asp Glu Leu Thr Asp Ser
            2230                2235                2240

AAA CTG CCA AGT CAT GCC ACA CAT TCT CTT TTT ACA TGT CCC GAA AAT         7005
Lys Leu Pro Ser His Ala Thr His Ser Leu Phe Thr Cys Pro Glu Asn
2245                2250                2255

GAG GAA ATG GTT TTG TCA AAT TCA AGA ATT GGA AAA AGA AGA GGA GAG         7053
Glu Glu Met Val Leu Ser Asn Ser Arg Ile Gly Lys Arg Arg Gly Glu
2260                2265                2270                2275

CCC CTT ATC TTA GTG GGA GAA CCC TCA ATC AAA AGA AAC TTA TTA AAT         7101
Pro Leu Ile Leu Val Gly Glu Pro Ser Ile Lys Arg Asn Leu Leu Asn
            2280                2285                2290

GAA TTT GAC AGG ATA ATA GAA AAT CAA GAA AAA TCC TTA AAG GCT TCA         7149
Glu Phe Asp Arg Ile Ile Glu Asn Gln Glu Lys Ser Leu Lys Ala Ser
            2295                2300                2305

AAA AGC ACT CCA GAT GGC ACA ATA AAA GAT CGA AGA TTG TTT ATG CAT         7197
Lys Ser Thr Pro Asp Gly Thr Ile Lys Asp Arg Arg Leu Phe Met His
            2310                2315                2320

CAT GTT TCT TTA GAG CCG ATT ACC TGT GTA CCC TTT CGC ACA ACT AAG         7245
```

```
His Val Ser Leu Glu Pro Ile Thr Cys Val Pro Phe Arg Thr Thr Lys
        2325                2330                2335

GAA CGT CAA GAG ATA CAG AAT CCA AAT TTT ACC GCA CCT GGT CAA GAA    7293
Glu Arg Gln Glu Ile Gln Asn Pro Asn Phe Thr Ala Pro Gly Gln Glu
2340                2345                2350                2355

TTT CTG TCT AAA TCT CAT TTG TAT GAA CAT CTG ACT TTG GAA AAA TCT    7341
Phe Leu Ser Lys Ser His Leu Tyr Glu His Leu Thr Leu Glu Lys Ser
                2360                2365                2370

TCA AGC AAT TTA GCA GTT TCA GGA CAT CCA TTT TAT CAA GTT TCT GCT    7389
Ser Ser Asn Leu Ala Val Ser Gly His Pro Phe Tyr Gln Val Ser Ala
            2375                2380                2385

ACA AGA AAT GAA AAA ATG AGA CAC TTG ATT ACT ACA GGC AGA CCA ACC    7437
Thr Arg Asn Glu Lys Met Arg His Leu Ile Thr Thr Gly Arg Pro Thr
        2390                2395                2400

AAA GTC TTT GTT CCA CCT TTT AAA ACT AAA TCA CAT TTT CAC AGA GTT    7485
Lys Val Phe Val Pro Pro Phe Lys Thr Lys Ser His Phe His Arg Val
    2405                2410                2415

GAA CAG TGT GTT AGG AAT ATT AAC TTG GAG GAA AAC AGA CAA AAG CAA    7533
Glu Gln Cys Val Arg Asn Ile Asn Leu Glu Glu Asn Arg Gln Lys Gln
2420                2425                2430                2435

AAC ATT GAT GGA CAT GGC TCT GAT GAT AGT AAA AAT AAG ATT AAT GAC    7581
Asn Ile Asp Gly His Gly Ser Asp Asp Ser Lys Asn Lys Ile Asn Asp
                2440                2445                2450

AAT GAG ATT CAT CAG TTT AAC AAA AAC AAC TCC AAT CAA GCA GCA GCT    7629
Asn Glu Ile His Gln Phe Asn Lys Asn Asn Ser Asn Gln Ala Ala Ala
            2455                2460                2465

GTA ACT TTC ACA AAG TGT GAA GAA GAA CCT TTA GAT TTA ATT ACA AGT    7677
Val Thr Phe Thr Lys Cys Glu Glu Glu Pro Leu Asp Leu Ile Thr Ser
        2470                2475                2480

CTT CAG AAT GCC AGA GAT ATA CAG GAT ATG CGA ATT AAG AAG AAA CAA    7725
Leu Gln Asn Ala Arg Asp Ile Gln Asp Met Arg Ile Lys Lys Lys Gln
    2485                2490                2495

AGG CAA CGC GTC TTT CCA CAG CCA GGC AGT CTG TAT CTT GCA AAA ACA    7773
Arg Gln Arg Val Phe Pro Gln Pro Gly Ser Leu Tyr Leu Ala Lys Thr
2500                2505                2510                2515

TCC ACT CTG CCT CGA ATC TCT CTG AAA GCA GCA GTA GGA GGC CAA GTT    7821
Ser Thr Leu Pro Arg Ile Ser Leu Lys Ala Ala Val Gly Gly Gln Val
                2520                2525                2530

CCC TCT GCG TGT TCT CAT AAA CAG CTG TAT ACG TAT GGC GTT TCT AAA    7869
Pro Ser Ala Cys Ser His Lys Gln Leu Tyr Thr Tyr Gly Val Ser Lys
            2535                2540                2545

CAT TGC ATA AAA ATT AAC AGC AAA AAT GCA GAG TCT TTT CAG TTT CAC    7917
His Cys Ile Lys Ile Asn Ser Lys Asn Ala Glu Ser Phe Gln Phe His
        2550                2555                2560

ACT GAA GAT TAT TTT GGT AAG GAA AGT TTA TGG ACT GGA AAA GGA ATA    7965
Thr Glu Asp Tyr Phe Gly Lys Glu Ser Leu Trp Thr Gly Lys Gly Ile
    2565                2570                2575

CAG TTG GCT GAT GGT GGA TGG CTC ATA CCC TCC AAT GAT GGA AAG GCT    8013
Gln Leu Ala Asp Gly Gly Trp Leu Ile Pro Ser Asn Asp Gly Lys Ala
2580                2585                2590                2595

GGA AAA GAA GAA TTT TAT AGG GCT CTG TGT GAC ACT CCA GGT GTG GAT    8061
Gly Lys Glu Glu Phe Tyr Arg Ala Leu Cys Asp Thr Pro Gly Val Asp
                2600                2605                2610

CCA AAG CTT ATT TCT AGA ATT TGG GTT TAT AAT CAC TAT AGA TGG ATC    8109
Pro Lys Leu Ile Ser Arg Ile Trp Val Tyr Asn His Tyr Arg Trp Ile
            2615                2620                2625

ATA TGG AAA CTG GCA GCT ATG GAA TGT GCC TTT CCT AAG GAA TTT GCT    8157
Ile Trp Lys Leu Ala Ala Met Glu Cys Ala Phe Pro Lys Glu Phe Ala
        2630                2635                2640
```

```
                                              -continued

AAT AGA TGC CTA AGC CCA GAA AGG GTG CTT CTT CAA CTA AAA TAC AGA       8205
Asn Arg Cys Leu Ser Pro Glu Arg Val Leu Leu Gln Leu Lys Tyr Arg
        2645                2650                2655

TAT GAT ACG GAA ATT GAT AGA AGC AGA AGA TCG GCT ATA AAA AAG ATA       8253
Tyr Asp Thr Glu Ile Asp Arg Ser Arg Arg Ser Ala Ile Lys Lys Ile
2660                2665                2670                2675

ATG GAA AGG GAT GAC ACA GCT GCA AAA ACA CTT GTT CTC TGT GTT TCT       8301
Met Glu Arg Asp Asp Thr Ala Ala Lys Thr Leu Val Leu Cys Val Ser
                2680                2685                2690

GAC ATA ATT TCA TTG AGC GCA AAT ATA TCT GAA ACT TCT AGC AAT AAA       8349
Asp Ile Ile Ser Leu Ser Ala Asn Ile Ser Glu Thr Ser Ser Asn Lys
        2695                2700                2705

ACT AGT AGT GCA GAT ACC CAA AAA GTG GCC ATT ATT GAA CTT ACA GAT       8397
Thr Ser Ser Ala Asp Thr Gln Lys Val Ala Ile Ile Glu Leu Thr Asp
            2710                2715                2720

GGG TGG TAT GCT GTT AAG GCC CAG TTA GAT CCT CCC CTC TTA GCT GTC       8445
Gly Trp Tyr Ala Val Lys Ala Gln Leu Asp Pro Pro Leu Leu Ala Val
        2725                2730                2735

TTA AAG AAT GGC AGA CTG ACA GTT GGT CAG AAG ATT ATT CTT CAT GGA       8493
Leu Lys Asn Gly Arg Leu Thr Val Gly Gln Lys Ile Ile Leu His Gly
2740                2745                2750                2755

GCA GAA CTG GTG GGC TCT CCT GAT GCC TGT ACA CCT CTT GAA GCC CCA       8541
Ala Glu Leu Val Gly Ser Pro Asp Ala Cys Thr Pro Leu Glu Ala Pro
                2760                2765                2770

GAA TCT CTT ATG TTA AAG ATT TCT GCT AAC AGT ACT CGG CCT GCT CGC       8589
Glu Ser Leu Met Leu Lys Ile Ser Ala Asn Ser Thr Arg Pro Ala Arg
        2775                2780                2785

TGG TAT ACC AAA CTT GGA TTC TTT CCT GAC CCT AGA CCT TTT CCT CTG       8637
Trp Tyr Thr Lys Leu Gly Phe Phe Pro Asp Pro Arg Pro Phe Pro Leu
            2790                2795                2800

CCC TTA TCA TCG CTT TTC AGT GAT GGA GGA AAT GTT GGT TGT GTT GAT       8685
Pro Leu Ser Ser Leu Phe Ser Asp Gly Gly Asn Val Gly Cys Val Asp
2805                2810                2815

GTA ATT ATT CAA AGA GCA TAC CCT ATA CAG TGG ATG GAG AAG ACA TCA       8733
Val Ile Ile Gln Arg Ala Tyr Pro Ile Gln Trp Met Glu Lys Thr Ser
2820                2825                2830                2835

TCT GGA TTA TAC ATA TTT CGC AAT GAA AGA GAG GAA GAA AAG GAA GCA       8781
Ser Gly Leu Tyr Ile Phe Arg Asn Glu Arg Glu Glu Glu Lys Glu Ala
            2840                2845                2850

GCA AAA TAT GTG GAG GCC CAA CAA AAG AGA CTA GAA GCC TTA TTC ACT       8829
Ala Lys Tyr Val Glu Ala Gln Gln Lys Arg Leu Glu Ala Leu Phe Thr
        2855                2860                2865

AAA ATT CAG GAG GAA TTT GAA GAA CAT GAA GAA AAC ACA ACA AAA CCA       8877
Lys Ile Gln Glu Glu Phe Glu Glu His Glu Glu Asn Thr Thr Lys Pro
            2870                2875                2880

TAT TTA CCA TCA CGT GCA CTA ACA AGA CAG CAA GTT CGT GCT TTG CAA       8925
Tyr Leu Pro Ser Arg Ala Leu Thr Arg Gln Gln Val Arg Ala Leu Gln
        2885                2890                2895

GAT GGT GCA GAG CTT TAT GAA GCA GTG AAG AAT GCA GCA GAC CCA GCT       8973
Asp Gly Ala Glu Leu Tyr Glu Ala Val Lys Asn Ala Ala Asp Pro Ala
2900                2905                2910                2915

TAC CTT GAG GGT TAT TTC AGT GAA GAG CAG TTA AGA GCC TTG AAT AAT       9021
Tyr Leu Glu Gly Tyr Phe Ser Glu Glu Gln Leu Arg Ala Leu Asn Asn
            2920                2925                2930

CAC AGG CAA ATG TTG AAT GAT AAG AAA CAA GCT CAG ATC CAG TTG GAA       9069
His Arg Gln Met Leu Asn Asp Lys Lys Gln Ala Gln Ile Gln Leu Glu
        2935                2940                2945

ATT AGG AAG GCC ATG GAA TCT GCT GAA CAA AAG GAA CAA GGT TTA TCA       9117
Ile Arg Lys Ala Met Glu Ser Ala Glu Gln Lys Glu Gln Gly Leu Ser
            2950                2955                2960
```

```
AGG GAT GTC ACA ACC GTG TGG AAG TTG CGT ATT GTA AGC TAT TCA AAA      9165
Arg Asp Val Thr Thr Val Trp Lys Leu Arg Ile Val Ser Tyr Ser Lys
        2965                2970                2975

AAA GAA AAA GAT TCA GTT ATA CTG AGT ATT TGG CGT CCA TCA TCA GAT      9213
Lys Glu Lys Asp Ser Val Ile Leu Ser Ile Trp Arg Pro Ser Ser Asp
2980                2985                2990                2995

TTA TAT TCT CTG TTA ACA GAA GGA AAG AGA TAC AGA ATT TAT CAT CTT      9261
Leu Tyr Ser Leu Leu Thr Glu Gly Lys Arg Tyr Arg Ile Tyr His Leu
            3000                3005                3010

GCA ACT TCA AAA TCT AAA AGT AAA TCT GAA AGA GCT AAC ATA CAG TTA      9309
Ala Thr Ser Lys Ser Lys Ser Lys Ser Glu Arg Ala Asn Ile Gln Leu
        3015                3020                3025

GCA GCG ACA AAA AAA ACT CAG TAT CAA CAA CTA CCG GTT TCA GAT GAA      9357
Ala Ala Thr Lys Lys Thr Gln Tyr Gln Gln Leu Pro Val Ser Asp Glu
        3030                3035                3040

ATT TTA TTT CAG ATT TAC CAG CCA CGG GAG CCC CTT CAC TTC AGC AAA      9405
Ile Leu Phe Gln Ile Tyr Gln Pro Arg Glu Pro Leu His Phe Ser Lys
        3045                3050                3055

TTT TTA GAT CCA GAC TTT CAG CCA TCT TGT TCT GAG GTG GAC CTA ATA      9453
Phe Leu Asp Pro Asp Phe Gln Pro Ser Cys Ser Glu Val Asp Leu Ile
3060                3065                3070                3075

GGA TTT GTC GTT TCT GTT GTG AAA AAA ACA GGA CTT GCC CCT TTC GTC      9501
Gly Phe Val Val Ser Val Val Lys Lys Thr Gly Leu Ala Pro Phe Val
            3080                3085                3090

TAT TTG TCA GAC GAA TGT TAC AAT TTA CTG GCA ATA AAG TTT TGG ATA      9549
Tyr Leu Ser Asp Glu Cys Tyr Asn Leu Leu Ala Ile Lys Phe Trp Ile
        3095                3100                3105

GAC CTT AAT GAG GAC ATT ATT AAG CCT CAT ATG TTA ATT GCT GCA AGC      9597
Asp Leu Asn Glu Asp Ile Ile Lys Pro His Met Leu Ile Ala Ala Ser
        3110                3115                3120

AAC CTC CAG TGG CGA CCA GAA TCC AAA TCA GGC CTT CTT ACT TTA TTT      9645
Asn Leu Gln Trp Arg Pro Glu Ser Lys Ser Gly Leu Leu Thr Leu Phe
        3125                3130                3135

GCT GGA GAT TTT TCT GTG TTT TCT GCT AGT CCA AAA GAG GGC CAC TTT      9693
Ala Gly Asp Phe Ser Val Phe Ser Ala Ser Pro Lys Glu Gly His Phe
3140                3145                3150                3155

CAA GAG ACA TTC AAC AAA ATG AAA AAT ACT GTT GAG AAT ATT GAC ATA      9741
Gln Glu Thr Phe Asn Lys Met Lys Asn Thr Val Glu Asn Ile Asp Ile
            3160                3165                3170

CTT TGC AAT GAA GCA GAA AAC AAG CTT ATG CAT ATA CTG CAT GCA AAT      9789
Leu Cys Asn Glu Ala Glu Asn Lys Leu Met His Ile Leu His Ala Asn
        3175                3180                3185

GAT CCC AAG TGG TCC ACC CCA ACT AAA GAC TGT ACT TCA GGG CCG TAC      9837
Asp Pro Lys Trp Ser Thr Pro Thr Lys Asp Cys Thr Ser Gly Pro Tyr
        3190                3195                3200

ACT GCT CAA ATC ATT CCT GGT ACA GGA AAC AAG CTT CTG ATG TCT TCT      9885
Thr Ala Gln Ile Ile Pro Gly Thr Gly Asn Lys Leu Leu Met Ser Ser
        3205                3210                3215

CCT AAT TGT GAG ATA TAT TAT CAA AGT CCT TTA TCA CTT TGT ATG GCC      9933
Pro Asn Cys Glu Ile Tyr Tyr Gln Ser Pro Leu Ser Leu Cys Met Ala
3220                3225                3230                3235

AAA AGG AAG TCT GTT TCC ACA CCT GTC TCA GCC CAG ATG ACT TCA AAG      9981
Lys Arg Lys Ser Val Ser Thr Pro Val Ser Ala Gln Met Thr Ser Lys
            3240                3245                3250

TCT TGT AAA GGG GAG AAA GAG ATT GAT GAC CAA AAG AAC TGC AAA AAG     10029
Ser Cys Lys Gly Glu Lys Glu Ile Asp Asp Gln Lys Asn Cys Lys Lys
        3255                3260                3265

AGA AGA GCC TTG GAT TTC TTG AGT AGA CTG CCT TTA CCT CCA CCT GTT     10077
Arg Arg Ala Leu Asp Phe Leu Ser Arg Leu Pro Leu Pro Pro Pro Val
```

```
                3270              3275              3280
AGT CCC ATT TGT ACA TTT GTT TCT CCG GCT GCA CAG AAG GCA TTT CAG    10125
Ser Pro Ile Cys Thr Phe Val Ser Pro Ala Ala Gln Lys Ala Phe Gln
    3285              3290              3295

CCA CCA AGG AGT TGT GGC ACC AAA TAC GAA ACA CCC ATA AAG AAA AAA    10173
Pro Pro Arg Ser Cys Gly Thr Lys Tyr Glu Thr Pro Ile Lys Lys Lys
3300              3305              3310              3315

GAA CTG AAT TCT CCT CAG ATG ACT CCA TTT AAA AAA TTC AAT GAA ATT    10221
Glu Leu Asn Ser Pro Gln Met Thr Pro Phe Lys Lys Phe Asn Glu Ile
            3320              3325              3330

TCT CTT TTG GAA AGT AAT TCA ATA GCT GAC GAA GAA CTT GCA TTG ATA    10269
Ser Leu Leu Glu Ser Asn Ser Ile Ala Asp Glu Glu Leu Ala Leu Ile
        3335              3340              3345

AAT ACC CAA GCT CTT TTG TCT GGT TCA ACA GGA GAA AAA CAA TTT ATA    10317
Asn Thr Gln Ala Leu Leu Ser Gly Ser Thr Gly Glu Lys Gln Phe Ile
    3350              3355              3360

TCT GTC AGT GAA TCC ACT AGG ACT GCT CCC ACC AGT TCA GAA GAT TAT    10365
Ser Val Ser Glu Ser Thr Arg Thr Ala Pro Thr Ser Ser Glu Asp Tyr
    3365              3370              3375

CTC AGA CTG AAA CGA CGT TGT ACT ACA TCT CTG ATC AAA GAA CAG GAG    10413
Leu Arg Leu Lys Arg Arg Cys Thr Thr Ser Leu Ile Lys Glu Gln Glu
3380              3385              3390              3395

AGT TCC CAG GCC AGT ACG GAA GAA TGT GAG AAA AAT AAG CAG GAC ACA    10461
Ser Ser Gln Ala Ser Thr Glu Glu Cys Glu Lys Asn Lys Gln Asp Thr
            3400              3405              3410

ATT ACA ACT AAA AAA TAT ATC TAAGCATTTG CAAAGGCGAC AATAAATTAT       10512
Ile Thr Thr Lys Lys Tyr Ile
            3415

TGACGCTTAA CCTTTCCAGT TTATAAGACT GGAATATAAT TTCAAACCAC ACATTAGTAC  10572

TTATGTTGCA CAATGAGAAA AGAAATTAGT TTCAAATTTA CCTCAGCGTT TGTGTATCGG  10632

GCAAAAATCG TTTTGCCCGA TTCCGTATTG GTATACTTTT GCTTCAGTTG CATATCTTAA  10692

AACTAAATGT AATTTATTAA CTAATCAAGA AAAACATCTT TGGCTGAGCT CGGTGGCTCA  10752

TGCCTGTAAT CCCAACACTT TGAGAAGCTG AGGTGGGAGG AGTGCTTGAG GCCAGGAGTT  10812

CAAGACCAGC TGGGCAACA TAGGGAGACC CCCATCTTTA CGAAGAAAAA AAAAAAGGGG   10872

AAAAGAAAAT CTTTTAAATC TTTGGATTTG ATCACTACAA GTATTATTTT ACAAGTGAAA  10932

TAAACATACC ATTTTCTTTT AGATTGTGTC ATTAAATGGA ATGAGGTCTC TTAGTACAGT  10992

TATTTTGATG CAGATAATTC CTTTTAGTTT AGCTACTATT TTAGGGGATT TTTTTTAGAG  11052

GTAACTCACT ATGAAATAGT TCTCCTTAAT GCAAATATGT TGGTTCTGCT ATAGTTCCAT  11112

CCTGTTCAAA AGTCAGGATG AATATGAAGA GTGGTGTTTC CTTTTGAGCA ATTCTTCATC  11172

CTTAAGTCAG CATGATTATA AGAAAAATAG AACCCTCAGT GTAACTCTAA TTCCTTTTTA  11232

CTATTCCAGT GTGATCTCTG AAATTAAATT ACTTCAACTA AAAATTCAAA TACTTTAAAT  11292

CAGAAGATTT CATAGTTAAT TTATTTTTTT TTTCAACAAA ATGGTCATCC AAACTCAAAC  11352

TTGAGAAAAT ATCTTGCTTT CAAATTGACA CTA                               11385
```

(2) INFORMATION FOR SEQ ID NO:2:

(i) SEQUENCE CHARACTERISTICS:
        (A) LENGTH: 3418 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Ile Gly Ser Lys Glu Arg Pro Thr Phe Phe Glu Ile Phe Lys
 1               5                  10                  15

Thr Arg Cys Asn Lys Ala Asp Leu Gly Pro Ile Ser Leu Asn Trp Phe
             20                  25                  30

Glu Glu Leu Ser Ser Glu Ala Pro Pro Tyr Asn Ser Glu Pro Ala Glu
         35                  40                  45

Glu Ser Glu His Lys Asn Asn Asn Tyr Glu Pro Asn Leu Phe Lys Thr
         50                  55                  60

Pro Gln Arg Lys Pro Ser Tyr Asn Gln Leu Ala Ser Thr Pro Ile Ile
 65                  70                  75                  80

Phe Lys Glu Gln Gly Leu Thr Leu Pro Leu Tyr Gln Ser Pro Val Lys
                 85                  90                  95

Glu Leu Asp Lys Phe Lys Leu Asp Leu Gly Arg Asn Val Pro Asn Ser
             100                 105                 110

Arg His Lys Ser Leu Arg Thr Val Lys Thr Lys Met Asp Gln Ala Asp
             115                 120                 125

Asp Val Ser Cys Pro Leu Leu Asn Ser Cys Leu Ser Glu Ser Pro Val
             130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                 165                 170                 175

Pro Lys His Ile Ser Glu Ser Leu Gly Ala Glu Val Asp Pro Asp Met
             180                 185                 190

Ser Trp Ser Ser Ser Leu Ala Thr Pro Pro Thr Leu Ser Ser Thr Val
             195                 200                 205

Leu Ile Val Arg Asn Glu Glu Ala Ser Glu Thr Val Phe Pro His Asp
             210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                 245                 250                 255

Asn Gln Arg Glu Ala Ala Ser His Gly Phe Gly Lys Thr Ser Gly Asn
             260                 265                 270

Ser Phe Lys Val Asn Ser Cys Lys Asp His Ile Gly Lys Ser Met Pro
             275                 280                 285

Asn Val Leu Glu Asp Glu Val Tyr Glu Thr Val Val Asp Thr Ser Glu
             290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                 325                 330                 335

Asn Ala Asp Glu Cys Glu Lys Ser Lys Asn Gln Val Lys Glu Lys Tyr
             340                 345                 350

Ser Phe Val Ser Glu Val Glu Pro Asn Asp Thr Asp Pro Leu Asp Ser
             355                 360                 365

Asn Val Ala His Gln Lys Pro Phe Glu Ser Gly Ser Asp Lys Ile Ser
             370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                 405                 410                 415
```

-continued

```
Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
            435                 440                 445

Ile Ser Ser Leu Pro Lys Ser Glu Lys Pro Leu Asn Glu Glu Thr Val
            450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
            500                 505                 510

Lys Glu Thr Phe Asn Ala Ser Phe Ser Gly His Met Thr Asp Pro Asn
            515                 520                 525

Phe Lys Lys Glu Thr Glu Ala Ser Glu Ser Gly Leu Glu Ile His Thr
            530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
            580                 585                 590

Ala Ile His Asp Glu Thr Phe Tyr Lys Gly Lys Lys Ile Pro Lys Asp
            595                 600                 605

Gln Lys Ser Glu Leu Ile Asn Cys Ser Ala Gln Phe Glu Ala Asn Ala
            610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
            675                 680                 685

Lys Glu Ala Lys Cys Asn Lys Glu Lys Leu Gln Leu Phe Ile Thr Pro
690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Glu Val Leu Ala Ala
                725                 730                 735

Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
            755                 760                 765

Leu Ile Leu Thr Pro Thr Ser Lys Asp Val Leu Ser Asn Leu Val Met
            770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
```

-continued

```
              835                 840                 845
Val Gln Phe Asn Gln Asn Thr Asn Leu Arg Val Ile Gln Lys Asn Gln
850                 855                 860
Glu Glu Thr Thr Ser Ile Ser Lys Ile Thr Val Asn Pro Asp Ser Glu
865                 870                 875                 880
Glu Leu Phe Ser Asp Asn Glu Asn Asn Phe Val Phe Gln Val Ala Asn
                    885                 890                 895
Glu Arg Asn Asn Leu Ala Leu Gly Asn Thr Lys Glu Leu His Glu Thr
                900                 905                 910
Asp Leu Thr Cys Val Asn Glu Pro Ile Phe Lys Asn Ser Thr Met Val
            915                 920                 925
Leu Tyr Gly Asp Thr Gly Asp Lys Gln Ala Thr Gln Val Ser Ile Lys
    930                 935                 940
Lys Asp Leu Val Tyr Val Leu Ala Glu Glu Asn Lys Asn Ser Val Lys
945                 950                 955                 960
Gln His Ile Lys Met Thr Leu Gly Gln Asp Leu Lys Ser Asp Ile Ser
                965                 970                 975
Leu Asn Ile Asp Lys Ile Pro Glu Lys Asn Asn Asp Tyr Met Asn Lys
                980                 985                 990
Trp Ala Gly Leu Leu Gly Pro Ile Ser Asn His Ser Phe Gly Gly Ser
            995                 1000                1005
Phe Arg Thr Ala Ser Asn Lys Glu Ile Lys Leu Ser Glu His Asn Ile
    1010                1015                1020
Lys Lys Ser Lys Met Phe Phe Lys Asp Ile Glu Glu Gln Tyr Pro Thr
1025                1030                1035                1040
Ser Leu Ala Cys Val Glu Ile Val Asn Thr Leu Ala Leu Asp Asn Gln
                1045                1050                1055
Lys Lys Leu Ser Lys Pro Gln Ser Ile Asn Thr Val Ser Ala His Leu
                1060                1065                1070
Gln Ser Ser Val Val Val Ser Asp Cys Lys Asn Ser His Ile Thr Pro
            1075                1080                1085
Gln Met Leu Phe Ser Lys Gln Asp Phe Asn Ser Asn His Asn Leu Thr
    1090                1095                1100
Pro Ser Gln Lys Ala Glu Ile Thr Glu Leu Ser Thr Ile Leu Glu Glu
1105                1110                1115                1120
Ser Gly Ser Gln Phe Glu Phe Thr Gln Phe Arg Lys Pro Ser Tyr Ile
                1125                1130                1135
Leu Gln Lys Ser Thr Phe Glu Val Pro Glu Asn Gln Met Thr Ile Leu
                1140                1145                1150
Lys Thr Thr Ser Glu Glu Cys Arg Asp Ala Asp Leu His Val Ile Met
            1155                1160                1165
Asn Ala Pro Ser Ile Gly Gln Val Asp Ser Ser Lys Gln Phe Glu Gly
    1170                1175                1180
Thr Val Glu Ile Lys Arg Lys Phe Ala Gly Leu Leu Lys Asn Asp Cys
1185                1190                1195                1200
Asn Lys Ser Ala Ser Gly Tyr Leu Thr Asp Glu Asn Glu Val Gly Phe
                1205                1210                1215
Arg Gly Phe Tyr Ser Ala His Gly Thr Lys Leu Asn Val Ser Thr Glu
                1220                1225                1230
Ala Leu Gln Lys Ala Val Lys Leu Phe Ser Asp Ile Glu Asn Ile Ser
            1235                1240                1245
Glu Glu Thr Ser Ala Glu Val His Pro Ile Ser Leu Ser Ser Ser Lys
    1250                1255                1260
```

-continued

```
Cys His Asp Ser Val Val Ser Met Phe Lys Ile Glu Asn His Asn Asp
1265                1270                1275                1280

Lys Thr Val Ser Glu Lys Asn Asn Lys Cys Gln Leu Ile Leu Gln Asn
                1285                1290                1295

Asn Ile Glu Met Thr Thr Gly Thr Phe Val Glu Glu Ile Thr Glu Asn
            1300                1305                1310

Tyr Lys Arg Asn Thr Glu Asn Glu Asp Asn Lys Tyr Thr Ala Ala Ser
        1315                1320                1325

Arg Asn Ser His Asn Leu Glu Phe Asp Gly Ser Asp Ser Ser Lys Asn
    1330                1335                1340

Asp Thr Val Cys Ile His Lys Asp Glu Thr Asp Leu Leu Phe Thr Asp
1345                1350                1355                1360

Gln His Asn Ile Cys Leu Lys Leu Ser Gly Gln Phe Met Lys Glu Gly
                1365                1370                1375

Asn Thr Gln Ile Lys Glu Asp Leu Ser Asp Leu Thr Phe Leu Glu Val
            1380                1385                1390

Ala Lys Ala Gln Glu Ala Cys His Gly Asn Thr Ser Asn Lys Glu Gln
        1395                1400                1405

Leu Thr Ala Thr Lys Thr Glu Gln Asn Ile Lys Asp Phe Glu Thr Ser
    1410                1415                1420

Asp Thr Phe Phe Gln Thr Ala Ser Gly Lys Asn Ile Ser Val Ala Lys
1425                1430                1435                1440

Glu Ser Phe Asn Lys Ile Val Asn Phe Phe Asp Gln Lys Pro Glu Glu
                1445                1450                1455

Leu His Asn Phe Ser Leu Asn Ser Glu Leu His Ser Asp Ile Arg Lys
            1460                1465                1470

Asn Lys Met Asp Ile Leu Ser Tyr Glu Glu Thr Asp Ile Val Lys His
        1475                1480                1485

Lys Ile Leu Lys Glu Ser Val Pro Val Gly Thr Gly Asn Gln Leu Val
    1490                1495                1500

Thr Phe Gln Gly Gln Pro Glu Arg Asp Glu Lys Ile Lys Glu Pro Thr
1505                1510                1515                1520

Leu Leu Gly Phe His Thr Ala Ser Gly Lys Lys Val Lys Ile Ala Lys
                1525                1530                1535

Glu Ser Leu Asp Lys Val Lys Asn Leu Phe Asp Glu Lys Glu Gln Gly
            1540                1545                1550

Thr Ser Glu Ile Thr Ser Phe Ser His Gln Trp Ala Lys Thr Leu Lys
        1555                1560                1565

Tyr Arg Glu Ala Cys Lys Asp Leu Glu Leu Ala Cys Glu Thr Ile Glu
    1570                1575                1580

Ile Thr Ala Ala Pro Lys Cys Lys Glu Met Gln Asn Ser Leu Asn Asn
1585                1590                1595                1600

Asp Lys Asn Leu Val Ser Ile Glu Thr Val Val Pro Pro Lys Leu Leu
                1605                1610                1615

Ser Asp Asn Leu Cys Arg Gln Thr Glu Asn Leu Lys Thr Ser Lys Ser
            1620                1625                1630

Ile Phe Leu Lys Val Lys Val His Glu Asn Val Glu Lys Glu Thr Ala
        1635                1640                1645

Lys Ser Pro Ala Thr Cys Tyr Thr Asn Gln Ser Pro Tyr Ser Val Ile
    1650                1655                1660

Glu Asn Ser Ala Leu Ala Phe Tyr Thr Ser Cys Ser Arg Lys Thr Ser
1665                1670                1675                1680
```

-continued

```
Val Ser Gln Thr Ser Leu Leu Glu Ala Lys Lys Trp Leu Arg Glu Gly
            1685                1690                1695
Ile Phe Asp Gly Gln Pro Glu Arg Ile Asn Thr Ala Asp Tyr Val Gly
        1700                1705                1710
Asn Tyr Leu Tyr Glu Asn Asn Ser Asn Ser Thr Ile Ala Glu Asn Asp
    1715                1720                1725
Lys Asn His Leu Ser Glu Lys Gln Asp Thr Tyr Leu Ser Asn Ser Ser
1730                1735                1740
Met Ser Asn Ser Tyr Ser Tyr His Ser Asp Glu Val Tyr Asn Asp Ser
1745                1750                1755                1760
Gly Tyr Leu Ser Lys Asn Lys Leu Asp Ser Gly Ile Glu Pro Val Leu
            1765                1770                1775
Lys Asn Val Glu Asp Gln Lys Asn Thr Ser Phe Ser Lys Val Ile Ser
        1780                1785                1790
Asn Val Lys Asp Ala Asn Ala Tyr Pro Gln Thr Val Asn Glu Asp Ile
    1795                1800                1805
Cys Val Glu Glu Leu Val Thr Ser Ser Pro Cys Lys Asn Lys Asn
1810                1815                1820
Ala Ala Ile Lys Leu Ser Ile Ser Asn Ser Asn Asn Phe Glu Val Gly
1825                1830                1835                1840
Pro Pro Ala Phe Arg Ile Ala Ser Gly Lys Ile Val Cys Val Ser His
            1845                1850                1855
Glu Thr Ile Lys Lys Val Lys Asp Ile Phe Thr Asp Ser Phe Ser Lys
        1860                1865                1870
Val Ile Lys Glu Asn Asn Glu Asn Lys Ser Lys Ile Cys Gln Thr Lys
    1875                1880                1885
Ile Met Ala Gly Cys Tyr Glu Ala Leu Asp Asp Ser Glu Asp Ile Leu
    1890                1895                1900
His Asn Ser Leu Asp Asn Asp Glu Cys Ser Thr His Ser His Lys Val
1905                1910                1915                1920
Phe Ala Asp Ile Gln Ser Glu Glu Ile Leu Gln His Asn Gln Asn Met
            1925                1930                1935
Ser Gly Leu Glu Lys Val Ser Lys Ile Ser Pro Cys Asp Val Ser Leu
        1940                1945                1950
Glu Thr Ser Asp Ile Cys Lys Cys Ser Ile Gly Lys Leu His Lys Ser
    1955                1960                1965
Val Ser Ser Ala Asn Thr Cys Gly Ile Phe Ser Thr Ala Ser Gly Lys
    1970                1975                1980
Ser Val Gln Val Ser Asp Ala Ser Leu Gln Asn Ala Arg Gln Val Phe
1985                1990                1995                2000
Ser Glu Ile Glu Asp Ser Thr Lys Gln Val Phe Ser Lys Val Leu Phe
            2005                2010                2015
Lys Ser Asn Glu His Ser Asp Gln Leu Thr Arg Glu Glu Asn Thr Ala
        2020                2025                2030
Ile Arg Thr Pro Glu His Leu Ile Ser Gln Lys Gly Phe Ser Tyr Asn
    2035                2040                2045
Val Val Asn Ser Ser Ala Phe Ser Gly Phe Ser Thr Ala Ser Gly Lys
    2050                2055                2060
Gln Val Ser Ile Leu Glu Ser Ser Leu His Lys Val Lys Gly Val Leu
2065                2070                2075                2080
Glu Glu Phe Asp Leu Ile Arg Thr Glu His Ser Leu His Tyr Ser Pro
            2085                2090                2095
Thr Ser Arg Gln Asn Val Ser Lys Ile Leu Pro Arg Val Asp Lys Arg
```

-continued

```
              2100                2105                2110
Asn Pro Glu His Cys Val Asn Ser Glu Met Glu Lys Thr Cys Ser Lys
        2115                2120                2125
Glu Phe Lys Leu Ser Asn Asn Leu Asn Val Gly Gly Ser Ser Glu
        2130                2135                2140
Asn Asn His Ser Ile Lys Val Ser Pro Tyr Leu Ser Gln Phe Gln Gln
2145                2150                2155                2160
Asp Lys Gln Gln Leu Val Leu Gly Thr Lys Val Ser Leu Val Glu Asn
                2165                2170                2175
Ile His Val Leu Gly Lys Glu Gln Ala Ser Pro Lys Asn Val Lys Met
            2180                2185                2190
Glu Ile Gly Lys Thr Glu Thr Phe Ser Asp Val Pro Val Lys Thr Asn
        2195                2200                2205
Ile Glu Val Cys Ser Thr Tyr Ser Lys Asp Ser Glu Asn Tyr Phe Glu
    2210                2215                2220
Thr Glu Ala Val Glu Ile Ala Lys Ala Phe Met Glu Asp Asp Glu Leu
2225                2230                2235                2240
Thr Asp Ser Lys Leu Pro Ser His Ala Thr His Ser Leu Phe Thr Cys
                2245                2250                2255
Pro Glu Asn Glu Glu Met Val Leu Ser Asn Ser Arg Ile Gly Lys Arg
            2260                2265                2270
Arg Gly Glu Pro Leu Ile Leu Val Gly Glu Pro Ser Ile Lys Arg Asn
        2275                2280                2285
Leu Leu Asn Glu Phe Asp Arg Ile Ile Glu Asn Gln Glu Lys Ser Leu
    2290                2295                2300
Lys Ala Ser Lys Ser Thr Pro Asp Gly Thr Ile Lys Asp Arg Arg Leu
2305                2310                2315                2320
Phe Met His His Val Ser Leu Glu Pro Ile Thr Cys Val Pro Phe Arg
                2325                2330                2335
Thr Thr Lys Glu Arg Gln Glu Ile Gln Asn Pro Asn Phe Thr Ala Pro
            2340                2345                2350
Gly Gln Glu Phe Leu Ser Lys Ser His Leu Tyr Glu His Leu Thr Leu
        2355                2360                2365
Glu Lys Ser Ser Ser Asn Leu Ala Val Ser Gly His Pro Phe Tyr Gln
    2370                2375                2380
Val Ser Ala Thr Arg Asn Glu Lys Met Arg His Leu Ile Thr Thr Gly
2385                2390                2395                2400
Arg Pro Thr Lys Val Phe Val Pro Pro Phe Lys Thr Lys Ser His Phe
                2405                2410                2415
His Arg Val Glu Gln Cys Val Arg Asn Ile Asn Leu Glu Glu Asn Arg
            2420                2425                2430
Gln Lys Gln Asn Ile Asp Gly His Gly Ser Asp Asp Ser Lys Asn Lys
        2435                2440                2445
Ile Asn Asp Asn Glu Ile His Gln Phe Asn Lys Asn Asn Ser Asn Gln
    2450                2455                2460
Ala Ala Ala Val Thr Phe Thr Lys Cys Glu Glu Pro Leu Asp Leu
2465                2470                2475                2480
Ile Thr Ser Leu Gln Asn Ala Arg Asp Ile Gln Asp Met Arg Ile Lys
                2485                2490                2495
Lys Lys Gln Arg Gln Arg Val Phe Pro Gln Pro Gly Ser Leu Tyr Leu
            2500                2505                2510
Ala Lys Thr Ser Thr Leu Pro Arg Ile Ser Leu Lys Ala Ala Val Gly
        2515                2520                2525
```

-continued

```
Gly Gln Val Pro Ser Ala Cys Ser His Lys Gln Leu Tyr Thr Tyr Gly
    2530                2535                2540
Val Ser Lys His Cys Ile Lys Ile Asn Ser Lys Asn Ala Glu Ser Phe
2545                2550                2555                2560
Gln Phe His Thr Glu Asp Tyr Phe Gly Lys Glu Ser Leu Trp Thr Gly
                2565                2570                2575
Lys Gly Ile Gln Leu Ala Asp Gly Gly Trp Leu Ile Pro Ser Asn Asp
    2580                2585                2590
Gly Lys Ala Gly Lys Glu Glu Phe Tyr Arg Ala Leu Cys Asp Thr Pro
    2595                2600                2605
Gly Val Asp Pro Lys Leu Ile Ser Arg Ile Trp Val Tyr Asn His Tyr
    2610                2615                2620
Arg Trp Ile Ile Trp Lys Leu Ala Ala Met Glu Cys Ala Phe Pro Lys
2625                2630                2635                2640
Glu Phe Ala Asn Arg Cys Leu Ser Pro Glu Arg Val Leu Leu Gln Leu
                2645                2650                2655
Lys Tyr Arg Tyr Asp Thr Glu Ile Asp Arg Ser Arg Ser Ala Ile
    2660                2665                2670
Lys Lys Ile Met Glu Arg Asp Asp Thr Ala Ala Lys Thr Leu Val Leu
    2675                2680                2685
Cys Val Ser Asp Ile Ile Ser Leu Ser Ala Asn Ile Ser Glu Thr Ser
    2690                2695                2700
Ser Asn Lys Thr Ser Ser Ala Asp Thr Gln Lys Val Ala Ile Ile Glu
2705                2710                2715                2720
Leu Thr Asp Gly Trp Tyr Ala Val Lys Ala Gln Leu Asp Pro Pro Leu
                2725                2730                2735
Leu Ala Val Leu Lys Asn Gly Arg Leu Thr Val Gly Gln Lys Ile Ile
    2740                2745                2750
Leu His Gly Ala Glu Leu Val Gly Ser Pro Asp Ala Cys Thr Pro Leu
    2755                2760                2765
Glu Ala Pro Glu Ser Leu Met Leu Lys Ile Ser Ala Asn Ser Thr Arg
    2770                2775                2780
Pro Ala Arg Trp Tyr Thr Lys Leu Gly Phe Phe Pro Asp Pro Arg Pro
2785                2790                2795                2800
Phe Pro Leu Pro Leu Ser Ser Leu Phe Ser Asp Gly Gly Asn Val Gly
                2805                2810                2815
Cys Val Asp Val Ile Ile Gln Arg Ala Tyr Pro Ile Gln Trp Met Glu
    2820                2825                2830
Lys Thr Ser Ser Gly Leu Tyr Ile Phe Arg Asn Glu Arg Glu Glu Glu
    2835                2840                2845
Lys Glu Ala Ala Lys Tyr Val Glu Ala Gln Gln Lys Arg Leu Glu Ala
    2850                2855                2860
Leu Phe Thr Lys Ile Gln Glu Glu Phe Glu Glu His Glu Glu Asn Thr
2865                2870                2875                2880
Thr Lys Pro Tyr Leu Pro Ser Arg Ala Leu Thr Arg Gln Gln Val Arg
                2885                2890                2895
Ala Leu Gln Asp Gly Ala Glu Leu Tyr Glu Ala Val Lys Asn Ala Ala
    2900                2905                2910
Asp Pro Ala Tyr Leu Glu Gly Tyr Phe Ser Glu Glu Gln Leu Arg Ala
    2915                2920                2925
Leu Asn Asn His Arg Gln Met Leu Asn Asp Lys Lys Gln Ala Gln Ile
    2930                2935                2940
```

-continued

```
Gln Leu Glu Ile Arg Lys Ala Met Glu Ser Ala Glu Gln Lys Glu Gln
2945                2950                2955                2960

Gly Leu Ser Arg Asp Val Thr Thr Val Trp Lys Leu Arg Ile Val Ser
                2965                2970                2975

Tyr Ser Lys Lys Glu Lys Asp Ser Val Ile Leu Ser Ile Trp Arg Pro
            2980                2985                2990

Ser Ser Asp Leu Tyr Ser Leu Leu Thr Glu Gly Lys Arg Tyr Arg Ile
        2995                3000                3005

Tyr His Leu Ala Thr Ser Lys Ser Lys Ser Ser Glu Arg Ala Asn
    3010                3015                3020

Ile Gln Leu Ala Ala Thr Lys Lys Thr Gln Tyr Gln Gln Leu Pro Val
3025                3030                3035                3040

Ser Asp Glu Ile Leu Phe Gln Ile Tyr Gln Pro Arg Glu Pro Leu His
                3045                3050                3055

Phe Ser Lys Phe Leu Asp Pro Asp Phe Gln Pro Ser Cys Ser Glu Val
            3060                3065                3070

Asp Leu Ile Gly Phe Val Val Ser Val Val Lys Lys Thr Gly Leu Ala
        3075                3080                3085

Pro Phe Val Tyr Leu Ser Asp Glu Cys Tyr Asn Leu Leu Ala Ile Lys
    3090                3095                3100

Phe Trp Ile Asp Leu Asn Glu Asp Ile Ile Lys Pro His Met Leu Ile
3105                3110                3115                3120

Ala Ala Ser Asn Leu Gln Trp Arg Pro Glu Ser Lys Ser Gly Leu Leu
                3125                3130                3135

Thr Leu Phe Ala Gly Asp Phe Ser Val Phe Ser Ala Ser Pro Lys Glu
            3140                3145                3150

Gly His Phe Gln Glu Thr Phe Asn Lys Met Lys Asn Thr Val Glu Asn
        3155                3160                3165

Ile Asp Ile Leu Cys Asn Glu Ala Glu Asn Lys Leu Met His Ile Leu
    3170                3175                3180

His Ala Asn Asp Pro Lys Trp Ser Thr Pro Thr Lys Asp Cys Thr Ser
3185                3190                3195                3200

Gly Pro Tyr Thr Ala Gln Ile Ile Pro Gly Thr Gly Asn Lys Leu Leu
                3205                3210                3215

Met Ser Ser Pro Asn Cys Glu Ile Tyr Tyr Gln Ser Pro Leu Ser Leu
            3220                3225                3230

Cys Met Ala Lys Arg Lys Ser Val Ser Thr Pro Val Ser Ala Gln Met
        3235                3240                3245

Thr Ser Lys Ser Cys Lys Gly Glu Lys Glu Ile Asp Asp Gln Lys Asn
    3250                3255                3260

Cys Lys Lys Arg Arg Ala Leu Asp Phe Leu Ser Arg Leu Pro Leu Pro
3265                3270                3275                3280

Pro Pro Val Ser Pro Ile Cys Thr Phe Val Ser Pro Ala Ala Gln Lys
                3285                3290                3295

Ala Phe Gln Pro Pro Arg Ser Cys Gly Thr Lys Tyr Glu Thr Pro Ile
            3300                3305                3310

Lys Lys Lys Glu Leu Asn Ser Pro Gln Met Thr Pro Phe Lys Lys Phe
        3315                3320                3325

Asn Glu Ile Ser Leu Leu Glu Ser Asn Ser Ile Ala Asp Glu Glu Leu
    3330                3335                3340

Ala Leu Ile Asn Thr Gln Ala Leu Leu Ser Gly Ser Thr Gly Glu Lys
3345                3350                3355                3360

Gln Phe Ile Ser Val Ser Glu Ser Thr Arg Thr Ala Pro Thr Ser Ser
```

```
                    3365                3370                3375
Glu Asp Tyr Leu Arg Leu Lys Arg Arg Cys Thr Thr Ser Leu Ile Lys
            3380                3385                3390
Glu Gln Glu Ser Ser Gln Ala Ser Thr Glu Glu Cys Glu Lys Asn Lys
            3395                3400                3405
Gln Asp Thr Ile Thr Thr Lys Lys Tyr Ile
        3410                3415
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 1..2
        (D) OTHER INFORMATION: /note= "(NH2) at nucleotide 1"

(xi) SEQUENCE DESCRIPTION: SEQ ID NO:3:

GTAGTGCAAG GCTCGAGAAC NNNNNNNNNN NN                        32

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 1..2
        (D) OTHER INFORMATION: /note= "(NH2) at nucleotide 1"

(xi) SEQUENCE DESCRIPTION: SEQ ID NO:4:

TGAGTAGAAT TCTAACGGCC GTCATTGTTC                             30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO

```
        (iv) ANTI-SENSE: NO (vi) ORIGINAL SOURCE:
             (A) ORGANISM: Homo sapiens (ix) FEATURE:
             (A) NAME/KEY: misc_feature
             (B) LOCATION: 29..30
             (D) OTHER INFORMATION: /note= "(NH2) at nucleotide 30"

(xi) SEQUENCE DESCRIPTION: SEQ ID NO:5:

GAACAATGAC GGCCGTTAGA ATTCTACTCA                                            30

(2) INFORMATION FOR SEQ ID NO:6:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:6:

TCAGTAGAAT TCTAACGGCC GTCAT                                                 25

INFORMATION FOR SEQ ID NO:7:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (vi) ORIGINAL SOURCE:
             (A) ORGANISM: Homo sapiens (ix) FEATURE:
             (A) NAME/KEY: misc_feature
             (B) LOCATION: 1..2
             (D) OTHER INFORMATION: /note= "(PO4) at nucleotide 1"

(xi) SEQUENCE DESCRIPTION: SEQ ID NO:7:

GTAGTGCAAG GCTCGAGAAC                                                       20

(2) INFORMATION FOR SEQ ID NO:8:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO
```

(iv) ANTI-SENSE: NO (vi) ORIGINAL SOURCE:
            (A) ORGANISM: Homo sapiens (ix) FEATURE:
            (A) NAME/KEY: misc_feature
            (B) LOCATION: 1..2
            (D) OTHER INFORMATION: /note= "(PO4) at nucleotide 1"

(xi) SEQUENCE DESCRIPTION: SEQ ID NO:8:

TGAGTAGAAT TCTAACGGCC GTCATTG                                                    27

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 32..33
        (D) OTHER INFORMATION: /note= "(NH2) at nucleotide 33"

(xi) SEQUENCE DESCRIPTION: SEQ ID NO:9:

CCTTCACACG CGTATCGATT AGTCACNNNN NNN                                              33

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 1..2
        (D) OTHER INFORMATION: /note= "(PO4) at nucleotide 1"

(xi) SEQUENCE DESCRIPTION: SEQ ID NO:10:

GTGACTAATC GATACGCGTG TGAAGGTGC                                                   29

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "primer"

(iii) HYPOTHETICAL: NO (iv) ANTI-SENSE: NO (vi) ORIGINAL SOURCE:
            (A) ORGANISM: Homos sapiens (ix) FEATURE:
            (A) NAME/KEY: misc_feature
            (B) LOCATION: 1..2
            (D) OTHER INFORMATION: /note= "Biotinylated at nucleotide
                1"

(xi) SEQUENCE DESCRIPTION: SEQ ID NO:11:

TTGAAGAACA ACAGGACTTT CACTA                                          25

(2) INFORMATION FOR SEQ ID NO:12:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:12:

CACCTTCACA CGCGTATCG                                                 19

(2) INFORMATION FOR SEQ ID NO:13:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:13:

GTTCGTAATT GTTGTTTTA TGTTCAG                                         27

(2) INFORMATION FOR SEQ ID NO:14:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:14:

CCTTCACACG CGTATCGATT AG						22

(2) INFORMATION FOR SEQ ID NO:15:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:15:

TTTGGATCAT TTTCACACTG TC						22

(2) INFORMATION FOR SEQ ID NO:16:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:16:

GTGCTCATAG TCAGAAATGA AG						22

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:17:

TCTTCCCATC CTCACAGTAA G						21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:18:

GTACTGGGTT TTTAGCAAGC A                                     21

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:19:

GGTTAAAACT AAGGTGGGA                                       19

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:20:

ATTTGCCCAG CATGACACA                                       19

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                 (A) ORGANISM: Homo sapiens (xi) SEQUENCE DESCRIPTION: SEQ ID NO:21:

TTTCCCAGTA TAGAGGAGA                                                            19

(2) INFORMATION FOR SEQ ID NO:22:

(i) SEQUENCE CHARACTERISTICS:
                 (A) LENGTH: 21 base pairs
                 (B) TYPE: nucleic acid
                 (C) STRANDEDNESS: single
                 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                 (A) ORGANISM: Homo sapiens (xi) SEQUENCE DESCRIPTION: SEQ ID NO:22:

GTAGGAAAAT GTTTCATTTA A                                                         21

(2) INFORMATION FOR SEQ ID NO:23:

(i) SEQUENCE CHARACTERISTICS:
                 (A) LENGTH: 21 base pairs
                 (B) TYPE: nucleic acid
                 (C) STRANDEDNESS: single
                 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                 (A) ORGANISM: Homo sapiens (xi) SEQUENCE DESCRIPTION: SEQ ID NO:23:

ATCTAAAGTA GTATTCCAAC A                                                         21

(2) INFORMATION FOR SEQ ID NO:24:

(i) SEQUENCE CHARACTERISTICS:
                 (A) LENGTH: 19 base pairs
                 (B) TYPE: nucleic acid
                 (C) STRANDEDNESS: single
                 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                 (A) ORGANISM: Homo sapiens (xi) SEQUENCE DESCRIPTION: SEQ ID NO:24:

GGGGGTAAAA AAAGGGGAA                                                            19

(2) INFORMATION FOR SEQ ID NO:25:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:25:

GAGATAAGTC AGGTATGATT                                               20

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:26:

AATTGCCTGT ATGAGGCAGA                                               20

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:27:

GGCAATTCAG TAAACGTTAA                                               20

(2) INFORMATION FOR SEQ ID NO:28:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:28:

ATTGTCAGTT ACTAACACAC                                                                20

(2) INFORMATION FOR SEQ ID NO:29:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Homo sapiens (xi) SEQUENCE DESCRIPTION: SEQ ID NO:29:

GTGTCATGTA ATCAAATAGT                                                                20

(2) INFORMATION FOR SEQ ID NO:30:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Homo sapiens (xi) SEQUENCE DESCRIPTION: SEQ ID NO:30:

CAGGTTTAGA GACTTTCTC                                                                 19

(2) INFORMATION FOR SEQ ID NO:31:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Homo sapiens (xi) SEQUENCE DESCRIPTION: SEQ ID NO:31:

GGACCTAGGT TGATTGCA                                                                  18

(2) INFORMATION FOR SEQ ID NO:32:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:32:

GTCAAGAAAG GTAAGGTAA                                                    19

(2) INFORMATION FOR SEQ ID NO:33:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:33:

CTATGAGAAA GGTTGTGAG                                                    19

(2) INFORMATION FOR SEQ ID NO:34:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:34:

CCTAGTCTTG CTAGTTCTT                                                    19

(2) INFORMATION FOR SEQ ID NO:35:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: homo sapiens (xi) SEQUENCE DESCRIPTION: SEQ ID NO:35:

AACAGTTGTA GATACCTCTG AA                                                22

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:36:

GACTTTTTGA TACCCTGAAA TG          22

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:37:

CAGCATCTTG AATCTCATAC AG          22

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:38:

CATGTATACA GATGATGCCT AAG          23

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:39:

AACTTAGTGA AAAATATTTA GTGA                                                  24

(2) INFORMATION FOR SEQ ID NO:40:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:40:

ATACATCTTG ATTCTTTTCC AT                                                    22

(2) INFORMATION FOR SEQ ID NO:41:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:41:

TTTAGTGAAT GTGATTGATG GT                                                    22

(2) INFORMATION FOR SEQ ID NO:42:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:42:

AGAACCAACT TTGTCCTTAA                                                       20

(2) INFORMATION FOR SEQ ID NO:43:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:43:

TTAGATTTGT GTTTTGGTTG AA                                               22

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:44:

TAGCTCTTTT GGGACAATTC                                                  20

(2) INFORMATION FOR SEQ ID NO:45:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:45:

ATGGAAAAGA ATCAAGATGT AT                                               22

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
```

(A) ORGANISM: Homo sapiens (xi) SEQUENCE DESCRIPTION: SEQ ID NO:46:

CCTAATGTTA TGTTCAGAGA G                                              21

(2) INFORMATION FOR SEQ ID NO:47:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:47:

GCTACCTCCA AAACTGTGA                                                 19

(2) INFORMATION FOR SEQ ID NO:48:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:48:

GTGTAAAGCA GCATATAAAA AT                                             22

(2) INFORMATION FOR SEQ ID NO:49:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:49:

CTTGCTGCTG TCTACCTG                                                  18

(2) INFORMATION FOR SEQ ID NO:50:

(i) SEQUENCE CHARACTERISTICS:
            (A) LENGTH: 20 base pairs
            (B) TYPE: nucleic acid
            (C) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:50:

AGTGGTCTTA AGATAGTCAT                                                    20

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:51:

CCATAATTTA ACACCTAGCC A                                                  21

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:52:

CCAAAAAAGT TAAATCTGAC A                                                  21

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:53:

```
GGCTTTTATT CTGCTCATGG C                                              21

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:54:

CCTCTGCAGA AGTTTCCTCA C                                              21

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:55:

AACGGACTTG CTATTTACTG A                                              21

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:56:

AGTACCTTGC TCTTTTTCAT C                                              21

(2) INFORMATION FOR SEQ ID NO:57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)
```

```
        (iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:57:

CAGCTAGCGG GAAAAAAGTT A                                              21

(2) INFORMATION FOR SEQ ID NO:58:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:58:

TTCGGAGAGA TGATTTTTGT C                                              21

(2) INFORMATION FOR SEQ ID NO:59:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:59:

GCCTTAGCTT TTTACACAA                                                 19

(2) INFORMATION FOR SEQ ID NO:60:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:60:

TTTTTGATTA TATCTCGTTG                                                20

(2) INFORMATION FOR SEQ ID NO:61:
```

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:61:

TTATTCTCGT TGTTTTCCTT A                                              21

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:62:

CCATTAAATT GTCCATATCT A                                              21

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:63:

GACGTAGGTG AATAGTGAAG A                                              21

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

(vi) ORIGINAL SOURCE:
             (A) ORGANISM: Homo sapiens (xi) SEQUENCE DESCRIPTION: SEQ ID NO:64:

TCAAATTCCT CTAACACTCC                                                    20

(2) INFORMATION FOR SEQ ID NO:65:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:65:

GAAGATAGTA CCAAGCAAGT C                                                  21

(2) INFORMATION FOR SEQ ID NO:66:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:66:

TGAGACTTTG GTTCCTAATA C                                                  21

(2) INFORMATION FOR SEQ ID NO:67:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:67:

AGTAACGAAC ATTCAGACCA G                                                  21

(2) INFORMATION FOR SEQ ID NO:68:

(i) SEQUENCE CHARACTERISTICS:
             (A) LENGTH: 20 base pairs
             (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:68:

GTCTTCACTA TTCACCTACG                                                20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:69:

CCCCCAAACT GACTACACAA                                                20

(2) INFORMATION FOR SEQ ID NO:70:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:70:

AGCATACCAA GTCTACTGAA T                                              21

(2) INFORMATION FOR SEQ ID NO:71:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:71:
```

```
ACTCTTTCAA ACATTAGGTC A                                              21

(2) INFORMATION FOR SEQ ID NO:72:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:72:

TTGGAGAGGC AGGTGGAT                                                  18

(2) INFORMATION FOR SEQ ID NO:73:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:73:

CTATAGAGGG AGAACAGAT                                                 19

(2) INFORMATION FOR SEQ ID NO:74:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:74:

TTTATGCTGA TTTCTGTTGT AT                                             22

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)
```

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:75:

ATAAAACGGG AAGTGTTAAC T                                                  21

(2) INFORMATION FOR SEQ ID NO:76:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:76:

CTGTGAGTTA TTTGGTGCAT                                                    20

(2) INFORMATION FOR SEQ ID NO:77:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:77:

GAATACAAAA CAGTTACCAG A                                                  21

(2) INFORMATION FOR SEQ ID NO:78:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:78:

CACCACCAAA GGGGGAAA                                                      18

```
(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:79:

AAATGAGGGT CTGCAACAAA                                                20

(2) INFORMATION FOR SEQ ID NO:80:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:80:

GTCCGACCAG AACTTGAG                                                  18

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:81:

AGCCATTTGT AGGATACTAG                                                20

(2) INFORMATION FOR SEQ ID NO:82:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

```
       (vi) ORIGINAL SOURCE:
            (A) ORGANISM: Homo sapiens (xi) SEQUENCE DESCRIPTION: SEQ ID NO:82:

CTACTAGACG GGCGGAG                                                      17

(2) INFORMATION FOR SEQ ID NO:83:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:83:

ATGTTTTTGT AGTGAAGATT CT                                                22

(2) INFORMATION FOR SEQ ID NO:84:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:84:

TAGTTCGAGA GACAGTTAAG                                                   20

(2) INFORMATION FOR SEQ ID NO:85:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:85:

CAGTTTTGGT TTGTTATAAT TG                                                22

(2) INFORMATION FOR SEQ ID NO:86:

(i) SEQUENCE CHARACTERISTICS:
            (A) LENGTH: 21 base pairs
```

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:86:

CAGAGAATAG TTGTAGTTGT T                                              21

(2) INFORMATION FOR SEQ ID NO:87:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:87:

AACCTTAACC CATACTGCC                                                 19

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:88:

TTCAGTATCA TCCTATGTGG                                                20

(2) INFORMATION FOR SEQ ID NO:89:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
```

(xi) SEQUENCE DESCRIPTION: SEQ ID NO:89:

TTTTATTCTC AGTTATTCAG TG                            22

(2) INFORMATION FOR SEQ ID NO:90:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:90:

GAAATTGAGC ATCCTTAGTA A                             21

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:91:

AATTCTAGAG TCACACTTCC                               20

(2) INFORMATION FOR SEQ ID NO:92:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:92:

ATATTTTTAA GGCAGTTCTA GA                            22

(2) INFORMATION FOR SEQ ID NO:93:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:93:

TTACACACAC CAAAAAAGTC A                                              21

(2) INFORMATION FOR SEQ ID NO:94:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:94:

TGAAAACTCT TATGATATCT GT                                             22

(2) INFORMATION FOR SEQ ID NO:95:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:95:

TGAATGTTAT ATATGTGACT TTT                                            23

(2) INFORMATION FOR SEQ ID NO:96:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:96:

CTTGTTGCTA TTCTTTGTCT A                                              21

```
(2) INFORMATION FOR SEQ ID NO:97:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:97:

CCCTAGATAC TAAAAAATAA AG                                              22

(2) INFORMATION FOR SEQ ID NO:98:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:98:

CTTTTAGCAG TTATATAGTT TC                                              22

(2) INFORMATION FOR SEQ ID NO:99:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:99:

GCCAGAGAGT CTAAAACAG                                                  19

(2) INFORMATION FOR SEQ ID NO:100:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO
```

```
        (iv) ANTI-SENSE: NO (vi) ORIGINAL SOURCE:
             (A) ORGANISM: Homo sapiens (xi) SEQUENCE DESCRIPTION: SEQ ID NO:100:

CTTTGGGTGT TTTATGCTTG                                              20

(2) INFORMATION FOR SEQ ID NO:101:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:101:

TTTGTTGTAT TTGTCCTGTT TA                                           22

(2) INFORMATION FOR SEQ ID NO:102:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:102:

ATTTTGTTAG TAAGGTCATT TTT                                          23

(2) INFORMATION FOR SEQ ID NO:103:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:103:

GTTCTGATTG CTTTTTATTC C                                            21

(2) INFORMATION FOR SEQ ID NO:104:

(i) SEQUENCE CHARACTERISTICS:
```

```
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:104:

ATCACTTCTT CCATTGCATC                                           20

(2) INFORMATION FOR SEQ ID NO:105:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:105:

CCGTGGCTGG TAAATCTG                                             18

(2) INFORMATION FOR SEQ ID NO:106:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:106:

CTGGTAGCTC CAACTAATC                                            19

(2) INFORMATION FOR SEQ ID NO:107:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
```

(xi) SEQUENCE DESCRIPTION: SEQ ID NO:107:

ACCGGTACAA ACCTTTCATT G                                              21

(2) INFORMATION FOR SEQ ID NO:108:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:108:

CTATTTTGAT TTGCTTTTAT TATT                                           24

(2) INFORMATION FOR SEQ ID NO:109:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:109:

GCTATTTCCT TGATACTGGA C                                              21

(2) INFORMATION FOR SEQ ID NO:110:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:110:

TTGGAAACAT AAATATGTGG G                                              21

(2) INFORMATION FOR SEQ ID NO:111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:111:

ACTTACAGGA GCCACATAAC                                                        20

(2) INFORMATION FOR SEQ ID NO:112:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:112:

CTACATTAAT TATGATAGGC TCG                                                    23

(2) INFORMATION FOR SEQ ID NO:113:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:113:

GTACTAATGT GTGGTTTGAA A                                                      21

(2) INFORMATION FOR SEQ ID NO:114:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:114:

TCAATGCAAG TTCTTCGTCA GC                                                     22

(2) INFORMATION FOR SEQ ID NO:115:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:115:

GGGAAGCTTC ATAAGTCAGT C          21

(2) INFORMATION FOR SEQ ID NO:116:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:116:

TTTGTAATGA AGCATCTGAT ACC        23

(2) INFORMATION FOR SEQ ID NO:117:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:117:

AATGATGAAT GTAGCACGC            19

(2) INFORMATION FOR SEQ ID NO:118:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:118:

```
GTCTGAATGT TCGTTACT                                                    18

(2) INFORMATION FOR SEQ ID NO:119:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:119:

ACCATCAAAC ACATCATCC                                                   19

(2) INFORMATION FOR SEQ ID NO:120:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:120:

AGAAAGTAAC TTGGAGGGAG                                                  20

(2) INFORMATION FOR SEQ ID NO:121:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:121:

CTCCTGAAAC TGTTCCCTTG G                                                21

(2) INFORMATION FOR SEQ ID NO:122:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:122:
```

-continued

```
TAATGGTGCT GGGATATTTG G                                              21

(2) INFORMATION FOR SEQ ID NO:123:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:123:

GAATGTCGAA GAGCTTGTC                                                 19

(2) INFORMATION FOR SEQ ID NO:124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:124:

AAACATACGC TTAGCCAGAC                                                20
```

CHROMOSOME 13-LINKED BREAST CANCER SUSCEPTIBILITY GENE

CROSS REFERENCE TO RELATED APPLICATION

This application is a divisional of application Ser. No. 08/639,501, U.S. Pat. No. 5,837,492; filed on Apr. 29, 1996, U.S. Pat. No. 5,837,492; which is a continuation-in-part of application Ser. No. 08/585,391, filed on Jan. 11, 1996, now abandoned; which is a continuation-in-part of application Ser. No. 08/576,559 filed on Dec. 21, 1995, now abandoned; which is a continuation-in-part of application Ser. No. 08/575,359, filed on Dec. 20, 1995, now abandoned; which is a continuation-in-part of application Ser. No. 08/573,779, filed on Dec. 18, 1995, now abandoned; all of which are incorporated herein by reference.

FIELD OF THE INVENTION

The present invention relates generally to the field of human genetics. Specifically, the present invention relates to methods and materials used to isolate and detect a human cancer as predisposing gene (BRCA2), some mutant alleles of which cause susceptibility to cancer, in particular, breast cancer in females and males. More specifically, the invention relates to germline mutations in the BRCA2 gene and their use in the diagnosis of predisposition to breast cancer. The present invention further relates to somatic mutations in the BRCA2 gene in human breast cancer and their use in the diagnosis and prognosis of human breast cancer. Additionally, the invention relates to somatic mutations in the BRCA2 gene in other human cancers and their use in the diagnosis and prognosis of human cancers. The invention also relates to the therapy of human cancers which have a mutation in the BRCA2 gene, including gene therapy, protein replacement therapy and protein mimetics. The invention further relates to the screening of drugs for cancer therapy. Finally, the invention relates to the screening of the BRCA2 gene for mutations, which are useful for diagnosing the predisposition to breast cancer.

The publications and other materials used herein to illuminate the background of the invention, and in particular, cases to provide additional details respecting the practice, are incorporated herein by reference, and for convenience, are referenced by author and date in the following text and respectively grouped in the appended List of References.

BACKGROUND OF THE INVENTION

The genetics of cancer is complicated, involving multiple dominant, positive regulators of the transformed state (oncogenes) as well as multiple recessive, negative regulators (tumor suppressor genes). Over one hundred oncogenes have been characterized. Fewer than a dozen tumor suppressor genes have been identified, but the number is expected to increase beyond fifty (Knudson, 1993).

The involvement of so many genes underscores the complexity of the growth control mechanisms that operate in cells to maintain the integrity of normal tissue. This complexity is manifest in another way. So far, no single gene has been shown to participate in the development of all, or even the majority of human cancers. The most common oncogenic mutations are in the H-ras gene, found in 10–15% of all solid tumors (Anderson et al., 1992). The most frequently mutated tumor suppressor genes are the TP53 gene, homozygously deleted in roughly 50% of all tumors, and CDKN2, which was homozygously deleted in 46% of tumor cell lines examined (Kamb et al., 1994a). Without a target that is common to all transformed cells, the dream of a "magic bullet" that can destroy or revert cancer cells while leaving normal tissue unharmed is improbable. The hope for a new generation of specifically targeted antitumor drugs may rest on the ability to identify tumor suppressor genes or oncogenes that play general roles in control of cell division.

The tumor suppressor genes which have been cloned and characterized influence susceptibility to: 1) Retinoblastoma (RB1); 2) Wilms' tumor (WT1); 3) Li-Fraumeni (TP53); 4) Familial adenomatous polyposis (APC); 5) Neurofibromatosis type 1 (NF1); 6) Neurofibromatosis type 2 (NF2); 7) von Hippel-Lindau syndrome (VHL); 8) Multiple endocrine neoplasia type 2A (MEN2A), and 9) Melanoma (CDKN2).

Tumor suppressor loci that have been mapped genetically but not yet isolated include genes for: Multiple endocrine neoplasia type 1 (MEN1); Lynch cancer family syndrome 2 (LCFS2); Neuroblastoma (NB); Basal cell nevus syndrome (BCNS); Beckwith-Wiedemann syndrome (BWS); Renal cell carcinoma (RCC); Tuberous sclerosis 1 (TSC1); and Tuberous sclerosis 2 (TSC2). The tumor suppressor genes that have been characterized to date encode products with similarities to a variety of protein types, including DNA binding proteins (WT1), ancillary transcription regulators (RB1), GTPase activating proteins or GAPs (NF1), cytoskeletal components (NF2), membrane bound receptor kinases (MEN2A), cell cycle regulators (CDKN2) and others with no obvious similarity to known proteins (APC and VHL).

In many cases, the tumor suppressor gene originally identified through genetic studies has been shown to be lost or mutated in some sporadic tumors. This result suggests that regions of chromosomal aberration may signify the position of important tumor suppressor genes involved both in genetic predisposition to cancer and in sporadic cancer.

One of the hallmarks of several tumor suppressor genes characterized to date is that they are deleted at high frequency in certain tumor types. The deletions often involve loss of a single allele, a so-called loss of heterozygosity (LOH), but may also involve homozygous deletion of both alleles. For LOH, the remaining allele is presumed to be nonfunctional, either because of a preexisting inherited mutation, or because of a secondary sporadic mutation. Breast cancer is one of the most significant diseases that affects women. At the current rate, American women have a 1 in 8 risk of developing breast cancer by age 95 (American Cancer Society, 1992). Treatment of breast cancer at later stages is often futile and disfiguring, making early detection a high priority in medical management of the disease. Ovarian cancer, although less frequent than breast cancer, is often rapidly fatal and is the fourth most common cause of cancer mortality in American women. Genetic factors contribute to an ill-defined proportion of breast cancer incidence, estimated to be about 5% of all cases but approximately 25% of cases diagnosed before age 40 (Claus el al., 1991). Breast cancer has been subdivided into two types, early-age onset and late-age onset, based on an inflection in the age-specific incidence curve around age 50. Mutation of one gene, BRCA1, is thought to account for approximately 45% of familial breast cancer, but at least 80% of families with both breast and ovarian cancer (Easton et al., 1993).

The BRCA1 gene has been isolated (Futreal et al., 1994; Miki et al., 1994) following an intense effort following its mapping in 1990 (Hall et al., 1990; Narod et al., 1991). A second locus, BRCA2, has recently been mapped to chromosome 13 (Wooster et al., 1994) and appears to account for a proportion of early-onset breast cancer roughly equal to BRCA1, but confers a lower risk of ovarian cancer. The remaining susceptibility to early-onset breast cancer is divided between as-yet unmapped genes for familial cancer, and rarer germline mutations in genes such as TP53 (Malkin et al., 1990). It has also been suggested that heterozygote carriers for defective forms of the Ataxia-Telangiectasia gene are at higher risk for breast cancer (Swift et al., 1976; Swift el al., 1991). Late-age onset breast cancer is also often familial although the risks in relatives are not as high as those for early-onset breast cancer (Cannon-Albright et al., 1994; Mettlin et al., 1990). However, the percentage of such cases due to genetic susceptibility is unknown.

Breast cancer has long been recognized to be, in part, a familial disease (Anderson, 1972). Numerous investigators have examined the evidence for genetic inheritance and concluded that the data are most consistent with dominant inheritance for a major susceptibility locus or loci (Bishop and Gardner, 1980; Go et al., 1983; Williams and Anderson, 1984; Bishop et al., 1988; Newman et al., 1988; Claus et al., 1991). Recent results demonstrate that at least three loci exist which convey susceptibility to breast cancer as well as other cancers. These loci are the TP53 locus on chromosome 17p (Malkin et al., 1990), a 17q-linked susceptibility locus known as BRCA1 (Hall et al., 1990), and one or more loci responsible for the unmapped residual. Hall et al. (1990) indicated that the inherited breast cancer susceptibility in kindreds with early age onset is linked to chromosome 17q21; although subsequent studies by this group using a more appropriate genetic model partially refuted the limitation to early onset breast cancer (Margaritte et al., 1992).

Most strategies for cloning the chromosome 13-linked breast cancer predisposing gene (BRCA2) require precise genetic localization studies. The simplest model for the functional role of BRCA2 holds that alleles of BRCA2 that predispose to cancer are recessive to wild type alleles; that is, cells that contain at least one wild type BRCA2 allele are not cancerous. However, cells that contain one wild type BRCA2 allele and one predisposing allele may occasionally suffer loss of the wild type allele either by random mutation or by chromosome loss during cell division (nondisjunction). All the progeny of such a mutant cell lack the wild type function of BRCA2 and may develop into tumors. According to this model, predisposing alleles of BRCA2 are recessive, yet susceptibility to cancer is inherited in a dominant fashion: women who possess one predisposing allele (and one wild type allele) risk developing cancer, because their mammary epithelial cells may spontaneously lose the wild type BRCA2 allele. This model applies to a group of cancer susceptibility loci known as tumor suppressors or antioncogenes, a class of genes that includes the retinoblastoma gene and neurofibromatosis gene. By inference this model may explain the BRCA1 function, as has recently been suggested (Smith et al., 1992).

A second possibility is that BRCA2 predisposing alleles are truly dominant; that is, a wild type allele of BRCA2 cannot overcome the tumor forming role of the predisposing allele. Thus, a cell that carries both wild type and mutant alleles would not necessarily lose the wild type copy of BRCA2 before giving rise to malignant cells. Instead, mammary cells in predisposed individuals would undergo some other stochastic change(s) leading to cancer.

If BRCA2 predisposing alleles are recessive, the BRCA2 gene is expected to be expressed in normal mammary tissue but not functionally expressed in mammary tumors. In contrast, if BRCA2 predisposing alleles are dominant, the wild type BRCA2 gene may or may not be expressed in normal mammary tissue. However, the predisposing allele will likely be expressed in breast tumor cells.

The chromosome 13 linkage of BRCA2 was independently confirmed by studying fifteen families that had multiple cases of early-onset breast cancer cases that were not linked to BRCA1 (Wooster et al., 1994). These studies claimed to localize the gene within a large region, 6 centi-Morgans (cM), or approximately 6 million base pairs, between the markers D13S289 and D13S267, placing BRCA2 in a physical region defined by 13q12–13. The size of these regions and the uncertainty associated with them has made it difficult to design and implement physical mapping and/or cloning strategies for isolating the BRCA2 gene. Like BRCA1, BRCA2 appears to confer a high risk of early-onset breast cancer in females. However, BRCA2 does not appear to confer a substantially elevated risk of ovarian cancer, although it does appear to confer an elevated risk of male breast cancer (Wooster, et al., 1994).

Identification of a breast cancer susceptibility locus would permit the early detection of susceptible individuals and greatly increase our ability to understand the initial steps which lead to cancer. As susceptibility loci are often altered during tumor progression, cloning these genes could also be important in the development of better diagnostic and prognostic products, as well as better cancer therapies.

SUMMARY OF THE INVENTION

The present invention relates generally to the field of human genetics. Specifically, the present invention relates to methods and materials used to isolate and detect a human breast cancer predisposing gene (BRCA2), some alleles of which cause susceptibility to cancer, in particular breast cancer in females and males. More specifically, the present invention relates to germline mutations in the BRCA2 gene and their use in the diagnosis of predisposition to breast cancer. The invention further relates to somatic mutations in the BRCA2 gene in human breast cancer and their use in the diagnosis and prognosis of human breast cancer. Additionally, the invention relates to somatic mutations in the BRCA2 gene in other human cancers and their use in the diagnosis and prognosis of human cancers. The invention also relates to the therapy of human cancers which have a mutation in the BRCA2 gene, including gene therapy, protein replacement therapy and protein mimetics. The invention further relates to the screening of drugs for cancer therapy. Finally, the invention relates to the screening of the BRCA2 gene for mutations, which are useful for diagnosing the predisposition to breast cancer.

BRIEF DESCRIPTION OF THF DRAWINGS

FIG. 1 shows a schematic map of STSs, P1s, BACs and YACs in the BRCA2 region.

FIG. 2 shows the sequence-space relationship between the cDNA clones, hybrid selected clones, cDNA PCR products and genomic sequences used to assemble the BRCA2 transcript sequence. 2-Br-C:RACE is a biotin-capture RACE product obtained from both human breast and human thymus cDNA. The cDNA clone λ sC713.1 was identified by screening a pool of human testis and HepG2 cDNA libraries with hybrid selected clone GT 713. The sequence 1-BR:CG026 →5 kb was generated from a PCR product beginning at the exon ⅞ junction (within λ sC713.1) and terminating within an hybrid selected clone that is part of exon 11. The sequence of exon 11 was corrected by comparison to hybrid selected clones, genomic sequence in the public domain and radioactive DNA sequencing gels. Hybrid selected clones located within that exon (clone names beginning with nH or GT) are placed below it. The cDNA clones λ wCBF1B8.1, λ wCBF1A5.1, λ wCBF1 A5.12, λ wCBF1B6.2 and λ wCBF1B6.3 were identified by screening a pool of human mammary gland, placenta, testis and HepG2 cDNA libraries with the exon trapped clones wXBF1B8, wXPF1A5 and wXBF1B6. The clone λ wCBF1B6.3 is chimeric (indicated by the dashed line), but its 5' end contained an important overlap with λ wCBF1A5.1. denotes the translation initiator. denotes the translation terminator.

FIGS. 3A–3D show the DNA sequence of the BRCA2 gene (which is also set forth in SEQ ID NO:1).

FIG. 4 shows the genomic organization of the BRCA2 gene. The exons (boxes and/or vertical lines) are parsed across the genomic sequences (ftp://genome.wustl.edu/pub/gscl/brca;) (horizontal lines) such that their sizes and spacing are proportional. The name of each genomic sequence is given at the left side of the figure. The sequences 92M18.00541 and 92M18.01289 actually overlap. Distances between the other genomic sequences are not known. Neither the public database nor our sequence database contained genomic sequences overlapping with exon 21.

Exons 1, 11 and 21 are numbered. "*" denotes two adjacent exons spaced closely enough that they are not resolved at this scale.

FIGS. 5A–5D show a loss of heterozygosity (LOH) analysis of primary breast tumors. Alleles of STR markers are indicated below the chromatogram. Shown are one example of a tumor heterozygous at BRCA2 (FIGS. 5A and 5B) and an example of a tumor with LOH at BRCA2 (FIGS. 5C and 5D). Fluorescence units are on the ordinate; size in basepairs is on the abscissa. N is for normal (FIGS. 5A and 5C) and T is for tumor (FIGS. 5B and 5D).

DETAILED DESCRIPTION OF THE INVENTION

Figure 1:
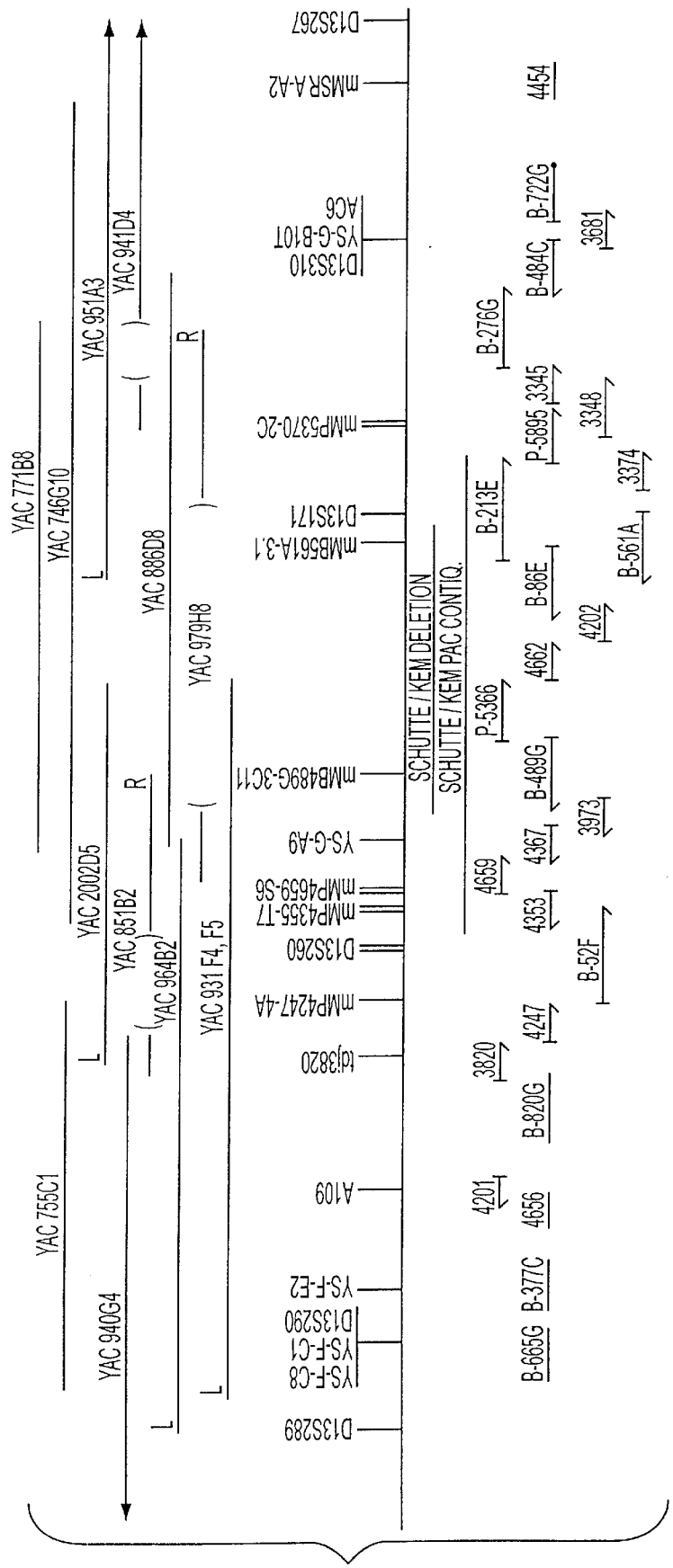

The present invention relates generally to the field of human genetics. Specifically, the present invention relates to methods and materials used to isolate and detect a human breast cancer predisposing gene (BRCA2), some alleles of which cause susceptibility to cancer, in particular breast cancer in females and males. More specifically, the present invention relates to germline mutations in the BRCA2 gene and their use in the diagnosis of predisposition to breast cancer. The invention further relates to somatic mutations in the BRCA2 gene in human breast cancer and their use in the diagnosis and prognosis of human breast cancer. Additionally, the invention relates to somatic mutations in the BRCA2 gene in other human cancers and their use in the diagnosis and prognosis of human cancers. The invention also relates to the therapy of human cancers which have a mutation in the BRCA2 gene, including gene therapy, protein replacement therapy and protein mimetics. The invention further relates to the screening of drugs for cancer therapy. Finally, the invention relates to the screening of the BRCA2 gene for mutations, which are useful for diagnosing the predisposition to breast cancer.

The present invention provides an isolated polynucleotide comprising all, or a portion of the BRCA2 locus or of a mutated BRCA2 locus, preferably at least eight bases and not more than about 100 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the BRCA2 locus or its expression product in an analyte. Such methods may further comprise the step of amplifying the portion of the BRCA2 locus, and may further include a step of providing a set of polynucleotides which are primers for amplification of said portion of the BRCA2 locus. The method is useful for either diagnosis of the predisposition to cancer or the diagnosis or prognosis of cancer.

The present invention also provides isolated antibodies, preferably monoclonal antibodies, which specifically bind to an isolated polypeptide comprised of at least five amino acid residues encoded by the BRCA2 locus.

The present invention also provides kits for detecting in an analyte a polynucleotide comprising a portion of the BRCA2 locus, the kits comprising a polynucleotide complementary to the portion of the BRCA2 locus packaged in a suitable container, and instructions for its use.

The present invention further provides methods of preparing a polynucleotide comprising polymerizing nucleotides to yield a sequence comprised of at least eight consecutive nucleotides of the BRCA2 locus; and methods of preparing a polypeptide comprising polymerizing amino acids to yield a sequence comprising at least five amino acids encoded within the BRCA2 locus.

The present invention further provides methods of screening the BRCA2 gene to identify mutations. Such methods may further comprise the step of amplifying a portion of the BRCA2 locus, and may further include a step of providing a set of polynucleotides which are primers for amplification of said portion of the BRCA2 locus. The method is useful for identifying mutations for use in either diagnosis of the predisposition to cancer or the diagnosis or prognosis of cancer.

The present invention further provides methods of screening suspected BRCA2 mutant alleles to identify mutations in the BRCA2 gene.

In addition, the present invention provides methods of screening drugs for cancer therapy to identify suitable drugs for restoring BRCA2 gene product function.

Finally, the present invention provides the means necessary for production of gene-based therapies directed at cancer cells. These therapeutic agents may take the form of polynucleotides comprising all or a portion of the BRCA2 locus placed in appropriate vectors or delivered to target cells in more direct ways such that the function of the BRCA2 protein is reconstituted. Therapeutic agents may also take the form of polypeptides based on either a portion of, or the entire protein sequence of BRCA2. These may functionally replace the activity of BRCA2 in vivo.

It is a discovery of the present invention that the BRCA2 locus which predisposes individuals to breast cancer, is a gene encoding a BRCA2 protein. This gene is termed BRCA2 herein. It is a discovery of the present invention that mutations in the BRCA2 locus in the germline are indicative of a predisposition to breast cancer in both men and women. Finally, it is a discovery of the present invention that somatic mutations in the BRCA2 locus are also associated with breast cancer and other cancers, which represents an indicator of these cancers or of the prognosis of these cancers. The mutational events of the BRCA2 locus can involve deletions, insertions and point mutations within the coding sequence and the non-coding sequence.

Starting from a region on human chromosome 13 of the human genome, which has a size estimated at about 6 million base pairs, a smaller region of 1 to 1.5 million bases which contains a genetic locus, BRCA2, which causes susceptibility to cancer, including breast cancer, has been identified.

The region containing the BRCA2 locus was identified using a variety of genetic techniques. Genetic mapping techniques initially defined the BRCA2 region in terms of recombination with genetic markers. Based upon studies of large extended families ("kindreds") with multiple cases of breast cancer, a chromosomal region has been pinpointed that contains the BRCA2 gene. A region which contains the BRCA2 locus is physically bounded by the markers D13S289 and D13S267.

The use of the genetic markers provided by this invention allowed the identification of clones which cover the region from a human yeast artificial chromosome (YAC) or a human bacterial artificial chromosome (BAC) library. It also allowed for the identification and preparation of more easily manipulated P1 and BAC clones from this region and the construction of a contig from a subset of the clones. These P1s, YACs and BACs provide the basis for cloning the BRCA2 locus and provide the basis for developing reagents effective, for example, in the diagnosis and treatment of breast and/or ovarian cancer. The BRCA2 gene and other potential susceptibility genes have been isolated from this region. The isolation was done using software trapping (a computational method for identifying sequences likely to contain coding exons, from contiguous or discontinuous genomic DNA sequences), hybrid selection techniques and direct screening, with whole or partial cDNA inserts from P1s and BACs, in the region to screen cDNA libraries. These methods were used to obtain sequences of loci expressed in breast and other tissue. These candidate loci were analyzed to identify sequences which confer cancer susceptibility. We have discovered that there are mutations in the coding sequence of the BRCA2 locus in kindreds which are responsible for the chromosome 13-linked cancer susceptibility known as BRCA2. The present invention not only facilitates the early detection of certain cancers, so vital to patient survival, but also permits the detection of susceptible individuals before they develop cancer.

Population Resources

Large, well-documented Utah kindreds are especially important in providing good resources for human genetic studies. Each large kindred independently provides the power to detect whether a BRCA2 susceptibility allele is segregating in that family. Recombinants informative for localization and isolation of the BRCA2 locus could be obtained only from kindreds large enough to confirm the presence of a susceptibility allele. Large sibships are especially important for studying breast cancer, since penetrance of the BRCA2 susceptibility allele is reduced both by age and sex, making informative sibships difficult to find. Furthermore, large sibships are essential for constructing haplotypes of deceased individuals by inference from the haplotypes of their close relatives.

While other populations may also provide beneficial information, such studies generally require much greater effort, and the families are usually much smaller and thus less informative. Utah's age-adjusted breast cancer incidence is 20% lower than the average U.S. rate. The lower incidence in Utah is probably due largely to an early age at first pregnancy, increasing the probability that cases found in Utah kindreds carry a genetic predisposition.

Genetic Mapping

Given a set of informative families, genetic markers are essential for linking a disease to a region of a chromosome. Such markers include restriction fragment length polymorphisms (RFLPs) (Botstein et al., 1980), markers with a variable number of tandem repeats (VNTRs) (Jeffreys et cl., 1985, Nakamura et al., 1987), and an abundant class of DNA polymorphisms based on short tandem repeats (STRs), especially repeats of CpA (Weber and May, 1989; Litt et al., 1989). To generate a genetic map, one selects potential genetic markers and tests them using DNA extracted from members of the kindreds being studied.

Genetic markers useful in searching for a genetic locus associated with a disease can be selected on an ad hoc basis, by densely covering a specific chromosome, or by detailed analysis of a specific region of a chromosome. A preferred method for selecting genetic markers linked with a disease involves evaluating the degree of informativeness of kindreds to determine the ideal distance between genetic markers of a given degree of polymorphism, then selecting markers from known genetic maps which are ideally spaced for maximal efficiency. Informativeness of kindreds is measured by the probability that the markers will be heterozygous in unrelated individuals. It is also most efficient to use STR markers which are detected by amplification of the target nucleic acid sequence using PCR; such markers are highly informative, easy to assay (Weber and May, 1989), and can be assayed simultaneously using multiplexing strategies (Skolnick and Wallace, 1988), greatly reducing the number of experiments required.

Once linkage has been established, one needs to find markers that flank the disease locus, i.e., one or more markers proximal to the disease locus, and one or more markers distal to the disease locus. Where possible, candidate markers can be selected from a known genetic map. Where none is known, new markers can be identified by the STR technique, as shown in the Examples.

Genetic mapping is usually an iterative process. In the present invention, it began by defining flanking genetic markers around the BRCA2 locus, then replacing these flanking markers with other markers that were successively closer to the BRCA2 locus. As an initial step, recombination events, defined by large extended kindreds, helped specifically to localize the BRCA2 locus as either distal or proximal to a specific genetic marker (Wooster el al., 1994).

The region surrounding BRCA2, until the disclosure of the present invention, was not well mapped and there were few markers. Therefore, short repetitive sequences were developed from cosmids, P1s, BACs and YACs, which physically map to the region and were analyzed in order to develop new genetic markers. Novel STRs were found which were both polymorphic and which mapped to the BRCA2 region.

Physical Mapping

Three distinct methods were employed to physically map the region. The first was the use of yeast artificial chromosomes (YACs) to clone the BRCA2 region. The second was the creation of a set of P1, BAC and cosmid clones which cover the region containing the BRCA2 locus.

Yeast Artificial Chromosomes (YACs). Once a sufficiently small region containing the BRCA2 locus was identified, physical isolation of the DNA in the region proceeded by identifying a set of overlapping YACs which covers the region. Useful YACs can be isolated from known libraries, such as the St. Louis and CEPH YAC libraries, which are widely distributed and contain approximately 50,000 YACs each. The YACs isolated were from these publicly accessible libraries and can be obtained from a number of sources including the Michigan Genome Center.

Clearly, others who had access to these YACs, without the disclosure of the present invention, would not have known the value of the specific YACs we selected since they would not have known which YACs were within, and which YACs outside of, the smallest region containing the BRCA2 locus.

P1 and BAC Clones. In the present invention, it is advantageous to proceed by obtaining P1 and BAC clones to cover this region. The smaller size of these inserts, compared to YAC inserts, makes them more useful as specific hybridization probes. Furthermore, having the cloned DNA in bacterial cells, rather than in yeast cells, greatly increases the ease with which the DNA of interest can be manipulated, and improves the signal-to-noise ratio of hybridization assays.

P1 and BAC clones are obtained by screening libraries constructed from the total human genome with specific sequence tagged sites (STSs) derived from the YACs, P1 s and BACs, isolated as described herein.

These P1 and BAC clones can be compared by interspersed repetitive sequence (IRS) PCR and/or restriction enzyme digests followed by gel electrophoresis and comparison of the resulting DNA fragments ("fingerprints") (Maniatis el al., 1982). The clones can also be characterized by the presence of STSs. The fingerprints are used to define an overlapping contiguous set of clones which covers the region but is not excessively redundant, referred to herein as a "minimum tiling path". Such a minimum tiling path forms the basis for subsequent experiments to identify cDNAs which may originate from the BRCA2 locus.

P1 clones (Sternberg, 1990; Sternberg et al., 1990; Pierce el al., 1992; Shizuya et al., 1992) were isolated by Genome Sciences using PCR primers provided by us for screening. BACs were provided by hybridization techniques in Dr. Mel Simon's laboratory and by analysis of PCR pools in our laboratory. The strategy of using P1 and BAC clones also permitted the covering of the genomic region with an independent set of clones not derived from YACs. This guards against the possibility of deletions in YACs. These new sequences derived from the P1 and BAC clones provide the material for further screening for candidate genes, as described below.

Gene Isolation.

There are many techniques for testing genomic clones for the presence of sequences likely to be candidates for the coding sequence of a locus one is attempting to isolate, including but not limited to: (a) zoo blots, (b) identifying HTF islands, (c) exon trapping, (d) hybridizing cDNA to P1s, BAC or YACs and (e) screening cDNA libraries.

(a) Zoo blots. The first technique is to hybridize cosmids to Southern blots to identify DNA sequences which are evolutionarily conserved, and which therefore give positive hybridization signals with DNA from species of varying degrees of relationship to humans (such as monkey, cow, chicken, pig, mouse and rat). Southern blots containing such DNA from a variety of species are commercially available (Clonetech, Cat. 7753-1).

(b) Identifying HTF islands. The second technique involves finding regions rich in the nucleotides C and G, which often occur near or within coding sequences. Such sequences are called HTF (HpaI tiny fragment) or CpG islands, as restriction enzymes specific for sites which contain CpG dimers cut frequently in these regions (Lindsay et al., 1987).

(c) Exon trapping. The third technique is exon trapping, a method that identifies sequences in genomic DNA which contain splice junctions and therefore are likely to comprise coding sequences of genes. Exon amplification (Buckler et al., 1991) is used to select and amplify exons from DNA clones described above. Exon amplification is based on the selection of RNA sequences which are flanked by functional 5' and/or 3' splice sites. The products of the exon amplification are used to screen the breast cDNA libraries to identify a manageable number of candidate genes for further study. Exon trapping can also be performed on small segments of sequenced DNA using computer programs or by software trapping.

(d) Hybridizing cDNA to P1s. BACs or YACs. The fourth technique is a modification of the selective enrichment technique which utilizes hybridization of cDNA to cosmids, P1s, BACs or YACs and permits transcribed sequences to be identified in, and recovered from cloned genomic DNA (Kandpal et al., 1990). The selective enrichment technique, as modified for the present purpose, involves binding DNA from the region of BRCA2 present in a YAC to a column matrix and selecting cDNAs from the relevant libraries which hybridize with the bound DNA, followed by amplification and purification of the bound DNA, resulting in a great enrichment for cDNAs in the region represented by the cloned genomic DNA.

(e) Identification of cDNAs. The fifth technique is to identify cDNAs that correspond to the BRCA2 locus. Hybridization probes containing putative coding sequences, selected using any of the above techniques, are used to screen various libraries, including breast tissue cDNA libraries and any other necessary libraries.

Another variation on the theme of direct selection of cDNA can be used to find candidate genes for BRCA2 (Lovett et al., 1991; Futreal, 1993). This method uses cosmid, P1 or BAC DNA as the probe. The probe DNA is digested with a blunt cutting restriction enzyme such as HaeIII. Double stranded adapters are then ligated onto the DNA and serve as binding sites for primers in subsequent PCR amplification reactions using biotinylated primers. Target cDNA is generated from mRNA derived from tissue samples, e.g., breast tissue, by synthesis of either random primed or oligo(dT) primed first strand followed by second strand synthesis. The cDNA ends are rendered blunt and ligated onto double-stranded adapters. These adapters serve as amplification sites for PCR. The target and probe sequences are denatured and mixed with human $C_o$t-1 DNA to block repetitive sequences. Solution hybridization is carried out to high $C_o$t-½ values to ensure hybridization of rare target cDNA molecules. The annealed material is then captured on avidin beads, washed at high stringency and the retained cDNAs are eluted and amplified by PCR. The selected cDNA is subjected to further rounds of enrichment before cloning into a plasmid vector for analysis.

Testing the cDNA for Candidacy

Proof that the cDNA is the BRCA2 locus is obtained by finding sequences in DNA extracted from affected kindred members which create abnormal BRCA2 gene products or abnormal levels of BRCA2 gene product. Such BRCA2 susceptibility alleles will co-segregate with the disease in large kindreds. They will also be present at a much higher frequency in non-kindred individuals with breast cancer then in individuals in the general population. Finally, since tumors often mutate somatically at loci which are in other instances mutated in the germline, we expect to see normal germline BRCA2 alleles mutated into sequences which are identical or similar to BRCA2 susceptibility alleles in DNA extracted from tumor tissue. Whether one is comparing BRCA2 sequences from tumor tissue to BRCA2 alleles from the germline of the same individuals, or one is comparing germline BRCA2 alleles from cancer cases to those from unaffected individuals, the key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and non-conservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary, tertiary or quaternary protein structure. Silent mutations or those resulting in conservative amino acid substitutions would not generally be expected to disrupt protein function.

According to the diagnostic and prognostic method of the present invention, alteration of the wild-type BRCA2 locus is detected. In addition, the method can be performed by detecting the wild-type BRCA2 locus and confirming the lack of a predisposition to cancer at the BRCA2 locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are somatically mutated, then a late neoplastic state is indicated. The finding of BRCA2 mutations thus provides both diagnostic and prognostic information. A BRCA2 allele which is not deleted (e.g., found on the sister chromosome to a chromosome carrying a BRCA2 deletion) can be screened for other mutations, such as insertions, small deletions, and point mutations. It is believed that many mutations found in tumor tissues will be those leading to decreased expression of the BRCA2 gene product. However, mutations leading to non-functional gene products would also lead to a cancerous state. Point mutational events may occur in regulatory regions. Such as in the promoter of the gene, leading to loss or diminution of expression of the mRNA. Point mutations may also abolish proper RNA processing, leading to loss of expression of the BRCA2 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below.

Predisposition to cancers, such as breast cancer, and the other cancers identified herein, can be ascertained by testing any tissue of a human for mutations of the BRCA2 gene. For example, a person who has inherited a germline BRCA2 mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the BRCA2 gene. Alteration of a wild-type BRCA2 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. For a gene as large as BRCA2, manual sequencing is very labor-intensive, but under optimal conditions, mutations in the coding sequence of a gene are rarely missed. Another approach is the single-stranded conformation polymorphism assay (SSCA) (Orita el al., 1989). This method does not detect all sequence changes, especially if the DNA fragment size is greater than 200 bp, but can be optimized to detect most DNA sequence variation. The reduced detection sensitivity is a disadvantage but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe el al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

In order to detect the alteration of the wild-type BRCA2 gene in a tissue, it is helpful to isolate the tissue free from surrounding normal tissues. Means for enriching tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of cancer cases, tumors, or both. Southern blots displaying hybridizing fragments (differing in length from control DNA when probed with sequences near or including the BRCA2 locus) indicate a possible mutation. If restriction enzymes which produce very large restriction fragments are used, then pulsed field gel electrophoresis (PFGE) is employed.

Detection of point mutations may be accomplished by molecular cloning of the BRCA2 allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined.

There are six well known methods for a more complete, yet still indirect, test for confirming the presence of a susceptibility allele: I) single stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano & Kidd, 1989). For allele-specific PCR, primers are used which hybridize at their 3' ends to a particular BRCA2 mutation. If the particular BRCA2 mutation is not present, an amplification product is not observed. Amplification Refractory Mutation System (ARMS) can also be used, as disclosed in European Patent Application Publication No. 0332435 and in Newton et al., 1989.

Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the BRCA2 mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type BRCA2 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the BRCA2 mRNA or gene but can be a segment of either. If the riboprobe comprises only a segment of the BRCA2 mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the BRCA2 gene can also be detected using Southern hybridization, especially if the changes are gross rearrangements, such as deletions and insertions.

DNA sequences of the BRCA2 gene which have been amplified by use of PCR may also be screened using allele-specific probes. These probes are nucleic acid oligomers, each of which contains a region of the BRCA2 gene sequence harboring a known mutation. For example, one oligomer may be about 30 nucleotides in length, corresponding to a portion of the BRCA2 gene sequence. By use of a battery of such allele-specific probes, PCR amplification products can be screened to identify the presence of a previously identified mutation in the BRCA2 gene. Hybridization of allele-specific probes with amplified BRCA2 sequences can be performed, for example, on a nylon filter. Hybridization to a particular probe under stringent hybridization conditions indicates the presence of the same mutation in the tumor tissue as in the allele-specific probe.

The most definitive test for mutations in a candidate locus is to directly compare genomic BRCA2 sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of BRCA2 can be detected by examining the non-coding regions, such as introns and regulatory sequences near or within the BRCA2 gene. An early indication that mutations in noncoding regions are important may come from Northern blot experiments that reveal messenger RNA molecules of abnormal size or abundance in cancer patients as compared to control individuals.

Alteration of BRCA2 mRNA expression can be detected by any techniques known in the art.

These include Northern blot analysis, PCR amplification and RNase protection. Diminished mRNA expression indicates an alteration of the wild-type BRCA2 gene. Alteration of wild-type BRCA2 genes can also be detected by screening for alteration of wild-type BRCA2 protein. For example, monoclonal antibodies immunoreactive with BRCA2 can be used to screen a tissue. Lack of cognate antigen would indicate a BRCA2 mutation. Antibodies specific for products of mutant alleles could also be used to detect mutant BRCA2 gene product. Such immunological assays can be done in any convenient formats known in the art. These include Western blots, immunohistochemical assays and ELISA assays. Any means for detecting an altered BRCA2 protein can be used to detect alteration of wild-type BRCA2 genes. Functional assays, such as protein binding determinations, can be used. In addition, assays can be used which detect BRCA2 biochemical function. Finding a mutant BRCA2 gene product indicates alteration of a wild-type BRCA2 gene.

Mutant BRCA2 genes or gene products can also be detected in other human body samples, such as serum, stool, urine and sputum. The same techniques discussed above for detection of mutant BRCA2 genes or gene products in tissues can be applied to other body samples. Cancer cells are sloughed off from tumors and appear in such body samples. In addition, the BRCA2 gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant BRCA2 genes or gene products.

The methods of diagnosis of the present invention are applicable to any tumor in which BRCA2 has a role in tumorigenesis. The diagnostic method of the present invention is useful for clinicians, so they can decide upon an appropriate course of treatment.

The primer pairs of the present invention are useful for determination of the nucleotide sequence of a particular BRCA2 allele using PCR. The pairs of single-stranded DNA primers can be annealed to sequences within or surrounding the BRCA2 gene on chromosome 13 in order to prime amplifying DNA synthesis of the BRCA2 gene itself. A complete set of these primers allows synthesis of all of the nucleotides of the BRCA2 gene coding sequences, i.e., the exons. The set of primers preferably allows synthesis of both intron and exon sequences. Allele-specific primers can also be used. Such primers anneal only to particular BRCA2 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from BRCA2 sequences or sequences adjacent to BRCA2, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the BRCA2 open reading frame shown in SEQ ID NO:1 and in FIG. 3, design of particular primers, in addition to those disclosed below, is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the BRCA2 gene or mRNA using other techniques.

It has been discovered that individuals with the wild-type BRCA2 gene do not have cancer which results from the BRCA2 allele. However, mutations which interfere with the function of the BRCA2 protein are involved in the pathogenesis of cancer. Thus, the presence of an altered (or a mutant) BRCA2 gene which produces a protein having a loss of function, or altered function, directly correlates to an increased risk of cancer. In order to detect a BRCA2 gene mutation, a biological sample is prepared and analyzed for a difference between the sequence of the BRCA2 allele being analyzed and the sequence of the wild-type BRCA2 allele. Mutant BRCA2 alleles can be initially identified by any of the techniques described above. The mutant alleles are then sequenced to identify the specific mutation of the particular mutant allele. Alternatively, mutant BRCA2 alleles can be initially identified by identifying mutant (altered) BRCA2 proteins, using conventional techniques. The mutant alleles are then sequenced to identify the specific mutation for each allele. The mutations, especially those which lead to an altered function of the BRCA2 protein, are then used for the diagnostic and prognostic methods of the present invention.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. These methods are well known and widely practiced in the art. See, e.g. U.S. Pat. Nos. 4.683,195 and 4.683.202 and Innis et al., 1990 (for PCR); and Wu et al., 1989a (for LCR). Reagents and hardware for conducting PCR are commercially available. Primers useful to amplify sequences from the BRCA2 region are preferably complementary to, and hybridize specifically to sequences in the BRCA2 region or in regions that flank a target region therein. BRCA2 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the BRCA2 polypeptides and fragments thereof or to polynucleotide sequences from the BRCA2 region, particularly from the BRCA2 locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the BRCA2 polypeptide or fragment. Monoclonal antibodies may be made by injecting mice with the protein polypeptides, fusion proteins or fragments thereof. Monoclonal antibodies will be screened by ELISA and tested for specific immunoreactivity with BRCA2 polypeptide or fragments thereof. See, Harlow & Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow & Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow & Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al. 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. The polynucleotides may be composed of DNA, RNA, or synthetic nucleotide analogs.

A "biological sample" refers to a sample of tissue or fluid suspected of containing an analyte polynucleotide or polypeptide from an individual including, but not limited to, e.g., plasma, serum, spinal fluid., lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"BRCA2 Allele" refers to normal alleles of the BRCA2 locus as well as alleles carrying variations that predispose individuals to develop cancer of many sites including, for example, breast, ovarian and stomach cancer. Such predisposing alleles are also called "BRCA2 susceptibility alleles".

"BRCA2 Locus," "BRCA2 Gene," "BRCA2 Nucleic Acids" or "BRCA2 Polynucleotide" each refer to polynucleotides, all of which are in the BRCA2 region, that are likely to be expressed in normal tissue, certain alleles of which predispose an individual to develop breast, ovarian and stomach cancers. Mutations at the BRCA2 locus may be involved in the initiation and/or progression of other types of tumors. The locus is indicated in part by mutations that predispose individuals to develop cancer. These mutations fall within the BRCA2 region described infra. The BRCA2 locus is intended to include coding sequences, intervening sequences and regulatory elements controlling transcription and/or translation. The BRCA2 locus is intended to include all allelic variations of the DNA sequence.

These terms, when applied to a nucleic acid, refer to a nucleic acid which encodes a BRCA2 polypeptide, fragment, homolog or variant, including, e.g., protein fusions or deletions. The nucleic acids of the present invention will possess a sequence which is either derived from, or substantially similar to a natural BRCA2-encoding gene or one having substantial homology with a natural BRCA2-encoding gene or a portion thereof. The coding sequence for a BRCA2 polypeptide is shown in SEQ ID NO:1 and FIG. 3, with the amino acid sequence shown in SEQ ID NO:2.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide link-ages substitute for phosphate linkages in the backbone of the molecule.

The present invention provides recombinant nucleic acids comprising all or part of the BRCA2 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in MRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a BRCA2-encoding sequence.

Techniques for nucleic acid manipulation are described generally, for example, in Sambrook el al., 1989 or Ausubel el al., 1992. Reagents useful in applying such techniques, such as restriction enzymes and the like, are widely known in the art and commercially available from such vendors as New England BioLabs, Boehringer Mannheim, Amersham, Promega Biotec, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using, appropriate probes. See, GenBank, National Institutes of Health.

"BRCA2 Region" refers to a portion of human chromosome 13 bounded by the markers tdj3820 and YS-G-B10T. This region contains the BRCA2 locus, including the BRCA2 gene.

As used herein, the terms "BRCA2 locus," "BRCA2 allele" and "BRCA2 region" all refer to the double-stranded DNA comprising the locus, allele, or region, as well as either of the single-stranded DNAs comprising the locus, allele or region.

As used herein, a "portion" of the BRCA2 locus or region or allele is defined as having a minimal size of at least about eight nucleotides, or preferably about 15 nucleotides, or more preferably at least about 25 nucleotides, and may have a minimal size of at least about 40 nucleotides.

"BRCA2 protein" or "BRCA2 polypeptide" refer to a protein or polypeptide encoded by the BRCA2 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native BRCA2 sequence, preferably in excess of about 90%, and more preferably at least about 95% homologous. Also included are proteins encoded by DNA which hybridize under high or low stringency conditions, to BRCA2-encoding nucleic acids and closely related polypeptides or proteins retrieved by antisera to the BRCA2 protein (s).

The length of polypeptide sequences compared for homology will generally be at least about 16 amino acids, usually at least about 20 residues, more usually at least about 24 residues, typically at least about 28 residues, and preferably more than about 35 residues. "Operably linked" refers to a juxtaposition wherein the components so described are in a relationship permitting them to function in their intended manner. For instance, a promoter is operably linked to a coding sequence if the promoter affects its transcription or expression.

"Probes". Polynucleotide polymorphisms associated with BRCA2 alleles which predispose to certain cancers or are associated with most cancers are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/ adventitious bindings, that is, which minimize noise. Since such indications identify neutral DNA polymorphisms as well as mutations, these indications need further analysis to demonstrate detection of a BRCA2 susceptibility allele.

Probes for BRCA2 alleles may be derived from the sequences of the BRCA2 region or its cDNAs. The probes may be of any suitable length, which span all or a portion of the BRCA2 region, and which allow specific hybridization to the BRCA2 region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding BRCA2 are preferred as probes. The probes may also be used to determine whether mRNA encoding BRCA2 is present in a cell or tissue.

"Protein modifications or fragments" are provided by the present invention for BRCA2 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$p, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of BRCA2 polypeptides. Immunological activities include both immunogenic function in a target immune system, as well as sharing of immunological epitopes for binding, serving as either a competitor or substitute antigen for an epitope of the BRCA2 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for BRCA2 polypeptides or fragments thereof is described below.

The present invention also provides for fusion polypeptides, comprising BRCA2 polypeptides and fragments. Homologous polypeptides may be fusions between two or more BRCA2 polypeptide sequences or between the sequences of BRCA2 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See, e.g., Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the BRCA2 polypeptides from other biological material, such as from cells transformed with recombinant nucleic acids encoding BRCA2, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% w/w of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A BRCA2 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type.

Synthetically made forms or molecules expressed by heterologous cells are inherently isolated molecules. "Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur & Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity.

"Substantially similar function" refers to the function of a modified nucleic acid or a modified protein, with reference to the wild-type BRCA2 nucleic acid or wild-type BRCA2 polypeptide. The modified polypeptide will be substantially homologous to the wild-type BRCA2 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type BRCA2 polypeptide. Alternatively, the similarity of function (activity) of the modified polypeptide may be higher than the activity of the wild-type BRCA2 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type BRCA2 gene function produces the modified protein described above.

Homology, for polypeptides, is typically measured using( sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie & Fink, 1991. A general discussion of techniques and materials for human gene mapping, including mapping of human chromosome 13, is provided, e.g., in White and Lalouel, 1988.

Preparation of recombinant or chemically synthesized nucleic acids; vectors, transformation, host cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, e.g., in Sambrook et al., 1989 or Ausubel et al., 1992.

The polynucleotides of the present invention may also be produced by chemical synthesis, e.g., by the phosphoramidite method described by Beaucage & Carruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native BRCA2 protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook el al, 1989 or Ausubel et al. 1992.

An appropriate promoter and other necessary vector sequences will be selected so as to be functional in the host, and may include, when appropriate, those naturally associated with BRCA2 genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England BioLabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al, 1978) or promoters derived from murine Moloney leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al. 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al, 1989 and Ausubel et al, 1992. The introduction of the polynucleotides into the host cell by any method known in the art, including inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the BRCA2 nucleic acids or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan, 1979. Examples of commonly used mammalian host cell lines are VERO and HeLa cells, Chinese hamster ovary (CHO) cells, and WI38. BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example in studying the characteristics of BRCA2 polypeptides.

Antisense polynucleotide sequences are useful in preventing or diminishing the expression of the BRCA2 locus, as will be appreciated by those skilled in the art. For example, polynucleotide vectors containing all or a portion of the BRCA2 locus or other sequences from the BRCA2 region (particularly those flanking the BRCA2 locus) may be placed under the control of a promoter in an antisense orientation and introduced into a cell. Expression of such an antisense construct within a cell will interfere with BRCA2 transcription and/or translation and/or replication.

The probes and primers based on the BRCA2 gene sequences disclosed herein are used to identify homologous BRCA2 gene sequences and proteins in other species. These BRCA2 gene sequences and proteins are used in the diagnostic/prognostic, therapeutic and drug screening methods described herein for the species from which they have been isolated.

Methods of Use: Nucleic Acid Diagnosis and Diagnostic Kits

In order to detect the presence of a BRCA2 allele predisposing an individual to cancer, a biological sample such as blood is prepared and analyzed for the presence or absence of susceptibility alleles of BRCA2. In order to detect the presence of neoplasia, the progression toward malignancy of a precursor lesion, or as a prognostic indicator, a biological sample of the lesion is prepared and analyzed for the presence or absence of mutant alleles of BRCA2. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant BRCA2 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte.

The region of the probes which is used to bind to the analyte can be made completely complementary to the targeted region of human chromosome 13. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis el al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews & Kricka, 1988, Landegren et al., 1988; Mittlin, 1989; U.S. Pat. No. 4,868,105, and in EPO Publication No. 225,807.

As noted above, non-PCR based screening assays are also contemplated in this invention. An exemplary non-PCR based procedure is provided in Example 6. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyne-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to preparation of oligodeoxynucleotide-alkaline phosphatase conjugates and their use as hybridization probes, see Jablonski et al., 1986.

Two-step label amplification methodologies are known in the art. These assays work on the principle that a small ligand (such as digoxigenin, biotin, or the like) is attached to a nucleic acid probe capable of specifically binding BRCA2. Exemplary probes can be developed on the basis of the sequence set forth in SEQ ID NO:1 and FIG. 3 of this patent application. Allele-specific probes are also contemplated within the scope of this example, and exemplary allele specific probes include probes encompassing the predisposing mutations described below, including those described in Table 2.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions.

For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting BRCA2. Thus, in one example to detect the presence of BRCA2 in a cell sample, more than one probe complementary to BRCA2 is employed and in particular the number of different probes is alternatively 2, 3, or 5 different nucleic acid probe sequences. In another example, to detect the presence of mutations in the BRCA2 gene sequence in a patient, more than one probe complementary to BRCA2 is employed where the cocktail includes probes capable of binding to the allele-specific mutations identified in populations of patients with alterations in BRCA2. In this embodiment, any number of probes can be used, and will preferably include probes corresponding to the major gene mutations identified as predisposing an individual to breast cancer. Some candidate probes contemplated within the scope of the invention include probes that include the allele-specific mutations described below and those that have the BRCA2 regions shown in SEQ ID NO:1 and FIG. 3, both 5' and 3' to the mutation site.

Methods of Use: Peptide Diagnosis and Diagnostic Kits

The neoplastic condition of lesions can also be detected on the basis of the alteration of wild-type BRCA2 polypeptide. Such alterations can be determined by sequence analysis in accordance with conventional techniques. More preferably, antibodies (polyclonal or monoclonal) are used to detect differences in, or the absence of BRCA2 peptides. The antibodies may be prepared as discussed above under the heading "Antibodies" and as further shown in Examples 9 and 10. Other techniques for raising and purifying antibodies are well known in the art and any such techniques may be chosen to achieve the preparations claimed in this invention. In a preferred embodiment of the invention, antibodies will immunoprecipitate BRCA2 proteins from solution as well as react with BRCA2 protein on Western or immunoblots of polyacrylamide gels. In another preferred embodiment, antibodies will detect BRCA2 proteins in paraffin or frozen tissue sections, using immunocytochemical techniques.

Preferred embodiments relating to methods for detecting BRCA2 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David el al. in U.S. Pat. Nos. 4,376,110 and 4,486,530, hereby incorporated by reference, and exemplified in Example 9.

Methods of Use: Drug Screening

This invention is particularly useful for screening compounds by using the BRCA2 polypeptide or binding fragment thereof in any of a variety of drug screening techniques.

The BRCA2 polypeptide or fragment employed in such a test may either be free in solution, affixed to a solid support, or home on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a BRCA2 polypeptide or fragment and the agent being tested, or examine the degree to which the formation of a complex between a BRCA2 polypeptide or fragment and a known ligand is interfered with by the agent being tested.

Thus, the present invention provides methods of screening for drugs comprising contacting such an agent with a BRCA2 polypeptide or fragment thereof and assaying (i) for the presence of a complex between the agent and the BRCA2 polypeptide or fragment, or (ii) for the presence of a complex between the BRCA2 polypeptide or fragment and a ligand, by methods well known in the art. In such competitive binding assays the BRCA2 polypeptide or fragment is typically labeled. Free BRCA2 polypeptide or fragment is separated from that present in a protein:protein complex, and the amount of free (i.e., uncomplexed) label is a measure of the binding of the agent being tested to BRCA2 or its interference with BRCA2:ligand binding, respectively.

Another technique for drug screening provides high throughput screening for compounds having suitable binding affinity to the BRCA2 polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with BRCA2 polypeptide and washed. Bound BRCA2 polypeptide is then detected by methods well known in the art. Purified BRCA2 can be coated directly onto plates for use in the aforementioned drug screening techniques. However non-neutralizing antibodies to the polypeptide can be used to capture antibodies to immobilize the BRCA2 polypeptide on the solid phase.

This invention also contemplates the use of competitive drug screening assays in which neutralizing antibodies capable of specifically binding the BRCA2 polypeptide compete with a test compound for binding to the BRCA2 polypeptide or fragments thereof. In this manner, the antibodies can be used to detect the presence of any peptide which shares one or more antigenic determinants of the BRCA2 polypeptide.

A further technique for drug screening involves the use of host eukaryotic cell lines or cells (such as described above) which have a nonfunctional BRCA2 gene. These host cell lines or cells are defective at the BRCA2 polypeptide level. The host cell lines or cells are grown in the presence of drug compound. The rate of growth of the host cells is measured to determine if the compound is capable of regulating the growth of BRCA2 defective cells.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., BRCA2 polypeptide) or, for example, of the BRCA2-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., BRCA2 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor.

The anti-id could then be used to identify and isolate peptides from banks of chemically or biologically produced banks of peptides. Selected peptides would then act as the pharmacore.

Thus, one may design drugs which have, e.g., improved BRCA2 polypeptide activity or stability or which act as inhibitors, agonists, antagonists, etc. of BRCA2 polypeptide activity. By virtue of the availability of cloned BRCA2 sequences, sufficient amounts of the BRCA2 polypeptide may be made available to perform such analytical studies as x-ray crystallography. In addition, the knowledge of the BRCA2 protein sequence provided herein will guide those employing computer modeling techniques in place of, or in addition to x-ray crystallography.

Methods of Use: Gene Therapy

According to the present invention, a method is also provided of supplying wild-type BRCA2 function to a cell which carries mutant BRCA2 alleles. Supplying such a function should suppress neoplastic growth of the recipient cells. The wild-type BRCA2 gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant BRCA2 allele, the gene fragment should encode a part of the BRCA2 protein which is required for non-neoplastic growth of the cell. More preferred is the situation where the wild-type BRCA2 gene or a part thereof is introduced into the mutant cell in such a way that it recombines with the endogenous mutant BRCA2 gene present in the cell. Such recombination requires a double recombination event which results in the correction of the BRCA2 gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the routineer. Cells transformed with the wild-type BRCA2 gene can be used as model systems to study cancer remission and drug treatments which promote such remission.

As generally discussed above, the BRCA2 gene or fragment, where applicable, may be employed in gene therapy methods in order to increase the amount of the expression products of such genes in cancer cells. Such gene therapy is particularly appropriate for use in both cancerous and pre-cancerous cells, in which the level of BRCA2 polypeptide is absent or diminished compared to normal cells. It may also be useful to increase the level of expression of a given BRCA2 gene even in those tumor cells in which the mutant gene is expressed at a "normal" level, but the gene product is not fully functional.

Gene therapy would be carried out according to generally accepted methods, for example, as described by Friedman, 1991. Cells from a patient's tumor would be first analyzed by the diagnostic methods described above, to ascertain the production of BRCA2 polypeptide in the tumor cells. A virus or plasmid vector (see further details below), containing a copy of the BRCA2 gene linked to expression control elements and capable of replicating inside the tumor cells, is prepared. Suitable vectors are known, such as disclosed in U.S. Pat. No. 5,252,479 and PCT published application WO 93/07282. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi el al., 1990), herpesviruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al., 1984; Mann and Baltimore. 1985; Miller el al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster el al., 1981; Constantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim el al., 1992); and direct DNA uptake and receptor-mediated DNA transfer (Wolff el al., 1990; Wu el al. 1991; Zenke el al., 1990; Wu et al., 1989b; Wolff et al., 1991; Wagner et al., 1990; Wagner el al., 1991; Cotten el al., 1990; Curiel et al., 1991a; Curiel et al., 1991b). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Gene transfer techniques which target DNA directly to breast and ovarian tissues, e.g., epithelial cells of the breast or ovaries, is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. One appropriate receptor/ligand pair may include the estrogen receptor and its ligand, estrogen (and estrogen analogues). These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy involves two steps which can be performed singly or jointly. In the first step, prepubescent females who carry a BRCA2 susceptibility allele are treated with a gene delivery vehicle such that some or all of their mammary ductal epithelial precursor cells receive at least one additional copy of a functional normal BRCA2 allele. In this step, the treated individuals have reduced risk of breast cancer to the extent that the effect of the susceptible allele has been countered by the presence of the normal allele. In the second step of a preventive therapy, predisposed young females, in particular women who have received the proposed gene therapeutic treatment, undergo hormonal therapy to mimic the effects on the breast of a full term pregnancy.

Methods of Use: Peptide Therapy

Peptides which have BRCA2 activity can be supplied to cells which carry mutant or missing BRCA2 alleles. The sequence of the BRCA2 protein is disclosed in SEQ ID NO:2. Protein can be produced by expression of the cDNA sequence in bacteria, for example, using known expression vectors. Alternatively, BRCA2 polypeptide can be extracted from BRCA2-producing mammalian cells. In addition, the techniques of synthetic chemistry can be employed to synthesize BRCA2 protein. Any of such techniques can provide the preparation of the present invention which comprises the BRCA2 protein. The preparation is substantially free of other human proteins. This is most readily accomplished by synthesis in a microorganism or in vitro.

Active BRCA2 molecules can be introduced into cells by microinjection or by use of liposomes, for example. Alternatively, some active molecules may be taken up by cells, actively or by diffusion. Extracellular application of the BRCA2 gene product may be sufficient to affect tumor growth. Supply of molecules with BRCA2 activity should lead to partial reversal of the neoplastic state. Other molecules with BRCA2 activity (for example, peptides, drugs or organic compounds) may also be used to effect such a reversal. Modified polypeptides having substantially similar function are also used for peptide therapy.

Methods of Use: Transformed Hosts

Similarly, cells and animals which carry a mutant BRCA2 allele can be used as model systems to study and test for substances which have potential as therapeutic agents. The cells are typically cultured epithelial cells. These may be isolated from individuals with BRCA2 mutations, either somatic or germline. Alternatively, the cell line can be engineered to carry the mutation in the BRCA2 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant BRCA2 alleles, usually from a second animal species, as well as insertion of disrupted homologous genes. Alternatively, the endogenous BRCA2 gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott el al., 1992; Snouwaert et al., 1992; Donehower el al., 1992). After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

The present invention is described by reference to the following Examples, which are offered by way of illustration and are not intended to limit the invention in any manner. Standard techniques well known in the art or the techniques specifically described below were utilized.

EXAMPLE 1

Ascertain and Study Kindreds Likely to Have a Chromosome 13-Linked Breast Cancer Susceptibility Locus Extensive cancer prone kindreds were ascertained from a defined population providing a large set of extended kindreds with multiple cases of breast cancer and many relatives available to study. The large number of meioses present in these large kindreds provided the power to detect whether the BRCA2 locus was segregating, and increased the opportunity for informative recombinants to occur within the small region being investigated. This vastly improved the chances of establishing linkage to the BRCA2 region, and greatly facilitated the reduction of the BRCA2 region to a manageable size, which permits identification of the BRCA2 locus itself.

Each kindred was extended through all available connecting relatives, and to all informative first degree relatives of each proband or cancer case. For these kindreds, additional breast cancer cases and individuals with cancer at other sites of interest who also appeared in the kindreds were identified through the tumor registry linked files. All breast cancers reported in the kindred which were not confirmed in the Utah Cancer Registry were researched. Medical records or death certificates were obtained for confirmation of all cancers. Each key connecting individual and all informative individuals were invited to participate by providing a blood sample from which DNA was extracted. We also sampled spouses and relatives of deceased cases so that the genotype of the deceased cases could be inferred from the genotypes of their relatives.

Kindreds which had three or more cancer cases with inferable genotypes were selected for linkage studies to chromosome 13 markers. These included kindreds originally ascertained from the linked databases for a study of proliferative breast disease and breast cancer (Skolnick et al., 1990). The criterion for selection of these kindreds was the presence of two sisters or a mother and her daughter with breast cancer. Additionally, kindreds which have been studied since 1980 as part of our breast cancer linkage studies and kindreds ascertained from the linked databases for the presence of clusters of male and female breast cancer and self-referred kindreds with early onset breast cancer were included. These kindreds were investigated and expanded in our clinic in the manner described above.

For each sample collected in these kindreds, DNA was extracted from blood or paraffin-embedded tissue blocks using standard laboratory protocols. Genotyping in this study was restricted to short tandem repeat (STR) markers since, in general, they have high heterozygosity and PCR methods offer rapid turnaround while using very small amounts of DNA. To aid in this effort, STR markers on chromosome 13 were developed by screening a chromosome specific cosmid library for clones which contained short tandem repeats of 2, 3 or 4, localized to the short arm in the region of the Rb tumor suppressor locus. Oligonucleotide sequences for markers not developed in our laboratory were obtained from published reports, or as part of the Breast Cancer Linkage Consortium, or from other investigators. All genotyping films were scored blindly with a standard lane marker used to maintain consistent coding of alleles. Key samples underwent duplicate typing for all relevant markers.

LOD scores for each kindred were calculated for two recombination fraction values, 0.001 and 0.1. (For calculation of LOD scores, see Ott 1985). Likelihoods were computed under the model derived by Claus et al., 1991, which assumes an estimated gene frequency of 0.003, a lifetime risk in female gene carriers of about 0.80, and population based age-specific risks for breast cancer in non-gene carriers. Allele frequencies for the markers used for the LOD score calculations were calculated from our own laboratory typings of unrelated individuals in the CEPH panel (White and Lalouel, 1988).

Kindred 107 is the largest chromosome 13-linked breast cancer family reported to date by any group. The evidence of linkage to chromosome 13 for this family is overwhelming. In smaller kindreds, sporadic cancers greatly confound the analysis of linkage and the correct identification of key recombinants.

In order to improve the characterization of our recombinants and define closer flanking markers, a dense map of this relatively small region on chromosome 13 was required. Our approach was to analyze existing STR markers provided by other investigators and any newly developed markers from our laboratory in our chromosome linked kindreds. FIG. 1 shows the location of ten markers used in the genetic analysis. Table 1 gives the LOD scores for linkage for each of the 19 kindreds in our study, which reduced the region to approximately 1.5 Mb.

TABLE 1

Haplotype and Phenotype Data for the 18 Families

| | Number of Cancer Cases(1) | | | | Posterior | tdj | D13S | | | mb | D13S | 5370- | | D13S | D13S |
|---|---|---|---|---|---|---|---|---|---|---|---|---|---|---|---|
| Kindred | FBR | MBR | OV | LOD | Probability (2) | 3820 | 4247 | 260 | GA9 | 561 | 171 | 2C | A6C | 310 | 267 |
| 107* | 22 | 3 | 2 | 5.06 | 1.00 | 8 | 28 | 4 | 10 | 8 | 3 | 2 | 6 | 4 | 12 |
| 8001 | 0 | 3 | 0 | n.d. | 0.90 | 8 | 30 | 6 | 10 | 7 | 10 | 5 | 5 | 5 | 4 |
| 8004 | 1 | 2 | 0 | n.d. | 0.90 | 9 | 11 | 4 | 4 | 7 | 8 | 6 | 8 | 4 | 12 |
| 2044* | 8 | 1 | 4 | 2.13 | 1.00 | 9 | 12 | 10 | 7 | 5 | 9 | 6 | 5 | 4 | 8 |
| 2043* | 2 | 1 | 1 | 0.86 | 0.98 | 6 | 30 | 3 | 12 | 7 | 10 | 5 | 8 | 4 | 12 |
| 2018 | 3 | 1 | 0 | n.d. | 0.90 | 9 | 12 | 7 | 3 | 8 | 3 | 6 | 6 | 5 | 8 |
| 937 | 3 | 1 | 0 | n.d. | 0.90 | 8 | 10 | 4 | — | — | 8 | 10 | 6 | 7 | 7 |
| 1018* | 9 | 1 | 0 | 2.47 | 1.00 | 6 | 17 | 8 | 10 | 5 | 8 | 2 | 5 | 4 | 8 |
| 2328 | 11 | 1 | 0 | 0.42 | 0.96 | 9 | 10 | 3 | 10 | 5 | 8 | 5 | 5 | 7 | 12 |
| 2263 | 2 | 1 | 0 | n.d. | 0.90 | 9 | 28 | 8 | — | 8 | 4 | — | — | 7 | 12 |
| 8002 | 2 | 1 | 0 | n.d. | 0.90 | 3 | 29 | 7 | 10 | 5 | 8 | 5 | 5 | 5 | 8 |
| 8003 | 2 | 1 | 0 | n.d. | 0.90 | 4 | 12 | 6 | 10 | 6 | 3 | 4 | 5 | 4 | 8 |
| 2367 | 6 | 0 | 1 | 0.40 | 0.85 | 6 | 28 | 7 | 10 | 12 | 3 | 7 | 5 | 5 | 4 |
| 2388 | 3 | 0 | 1 | 0.92 | 0.95 | 8 | 16 | 7 | 12 | 4 | 10 | 4 | 5 | 5 | 12 |
| 2027* | 4 | 0 | 0 | 0.39 | 0.85 | 4 | 11 | 3 | 10 | 7 | 10 | 5 | 6 | 7 | 12 |
| 4328 | 4 | 0 | 0 | 0.44 | 0.87 | 9 | 10 | 8 | 4 | 8 | 3 | 7 | 8 | 5 | 12 |
| 2355 | 3 | 0 | 0 | 0.36 | 0.84 | 9 | 10 | 6 | 4 | 6 | 3 | 7 | 3 | 5 | 8 |
| 2327 | 11 | 0 | 0 | 1.92 | 0.99 | 3 | 12 | 2 | 9 | 5 | 10 | 5 | 5 | 3 | 4 |
| 1019 | 2 | 2 | 0 | | | | | | | | | | | | |

*Families reported in Wooster et al. (1994).
n.d. = not determined
(1)Excludes cases known to be sporadic (i.e., do not share the BRCA2 haplotype segregating in the family).
FBR = female breast cancer under 60 years.
MBR = male breast cancer
OV = ovarian cancer
(2) Posterior probability assumes that, a priori, 90% of families with male breast and early onset female breast cancers that are unlinked to BRCA1 are due to BRCA2, and 70% of female breast cancer families unlinked to BRCA1 are due to BRCA1.

Table 1 also gives the posterior probability of a kindred having a BRCA2 mutation based on LOD scores and prior probabilities. Four of these markers (D13S171, D13S260, D13S310 and D13S267) were previously known. The other six markers were found as part of our search for BRCA2. We were able to reduce the region to 1.5 megabases based on a recombinant in Kindred 107 with marker tdj3820 at the left boundary, and a second recombinant in Kindred 2043 with marker YS-G-B10T at the right boundary (see FIG. 1) which is at approximately the same location as AC6 and D13S3 10. Furthermore, a homozygous deletion was found in a pancreatic tumor cell line in the BRCA2 region which may have been driven by BRCA2 itself; this deletion is referred to as the Schutte/Kern deletion in FIG. 1 (Schutte et al., 1995). The Schutte/Kern contig in FIG. 1 refers to these authors' physical map which covers the deletion.

EXAMPLE 2

Development of Genetic and Physical Resources in the Region of Interest

To increase the number of highly polymorphic loci in the BRCA2 region, we developed a number of STR markers in our laboratory from P1s, BACs and YACs which physically map to the region. These markers allowed us to further refine the region (see Table 1 and the discussion above).

STSs in the desired region were used to identify YACs which contained them. These YACs were then used to identify subclones in P1s or BACs. These subclones were then screened for the presence of a short tandem repeats. Clones with a strong signal were selected preferentially, since they were more likely to represent repeats which have a large number of repeats and/or are of near-perfect fidelity to the pattern. Both of these characteristics are known to increase the probability of polymorphism (Weber et al., 1990). These clones were sequenced directly from the vector to locate the repeat. We obtained a unique sequence on one side of the short tandem repeat by using one of a set of possible primers complementary to the end of the repeat. Based on this unique sequence, a primer was made to sequence back across the repeat in the other direction, yielding a unique sequence for design of a second primer flanking it. STRs were then screened for polymorphism on a small group of unrelated individuals and tested against the hybrid panel to confirm their physical localization. New markers which satisfied these criteria were then typed in a set of unrelated individuals from Utah to obtain allele frequencies appropriate for the study of this population. Many of the other markers reported in this study were also tested in unrelated individuals to obtain similarly appropriate allele frequencies.

Using the procedure described above, novel STRs were found from these YACs which were both polymorphic and localized to the BRCA2 region. FIG. 1 shows a schematic map of STSs, P1s. BACs and YACs in the BRCA2 region.

EXAMPLE 3

Identification of Candidate cDNA Clones for the BRCA2 Locus by Genomic Analysis of the Contig Region 1. General Methods Complete screen of the plausible region. The first method to identify candidate cDNAs, although labor intensive, used known techniques. The method comprised the screening of P1 and BAC clones in the contig to identify putative coding sequences. The clones containing putative coding sequences were then used as probes on filters of cDNA libraries to identify candidate cDNA clones for future analysis. The clones were screened for putative coding sequences by either of two methods.

The P1 clones to be analyzed were digested with a restriction enzyme to release the human DNA from the vector DNA. The DNA was separated on a 14 cm, 0.5% agarose gel run overnight at 20 volts for 16 hours. The human DNA bands were cut out of the gel and electroeluted from the gel wedge at 100 volts for at least two hours in 0.5× Tris Acetate buffer (Maniatis et al., 1982).

The eluted Not I digested DNA (~15 kb to 25 kb) was then digested with EcoRI restriction enzyme to give smaller fragments (~0.5 kb to 5.0 kb) which melt apart more easily for the next step of labeling the DNA with radionucleotides. The DNA fragments were labeled by means of the hexamer random prime labeling method (Boehringer-Mannheim, Cat. #1004760). The labeled DNA was spermine precipitated (add 100 µl TE, 5 µl 0.1 M spermine, and 5 µl of 10 mg/ml salmon sperm DNA) to remove unincorporated radionucleotides. The labeled DNA was then resuspended in 100 µl TE, 0.5 M NaCl at 65° C. for 5 minutes and then blocked with Human $C_o$t-1 DNA for 2–4 hrs. as per the manufacturer's instructions (Gibco/BRL, Cat. #5279SA). The $C_o$t-1 blocked probe was incubated on the filters in the blocking solution overnight at 42° C. The filters were washed for 30 minutes at room temperature in 2×SSC, 0.1% SDS, and then in the same buffer for 30 minutes at 55° C. The filters were then exposed 1 to 3 days at –70° C. to Kodak XAR-5 film with an intensifying screen. Thus, the blots were hybridized with either the pool of Eco-RI fragments from the insert, or each of the fragments individually.

The human DNA from clones in the region was isolated as whole insert or as EcoRI fragments and labeled as described above. The labeled DNA was used to screen filters of various cDNA libraries under the same conditions described above except that the cDNA filters undergo a more stringent wash of 0.1×SSC, 0.1% SDS at 65° C. for 30 minutes twice.

Most of the cDNA libraries used to date in our studies (libraries from normal breast tissue, breast tissue from a woman in her eighth month of pregnancy and a breast malignancy) were prepared at Clonetech, Inc. The cDNA library generated from breast tissue of an 8 month pregnant woman is available from Clonetech (Cat. #HL1037a) in the Lambda gt-10 vector, and is grown in C600Hf1 bacterial host cells. Normal breast tissue and malignant breast tissue samples were isolated from a 37 year old Caucasian female and one-gram of each tissue was sent to Clonetech for mRNA processing and cDNA library construction. The latter two libraries were generated using both random and oligo-dT priming, with size selection of the final products which were then cloned into the Lambda Zap II vector, and grown in XL1-blue strain of bacteria as described by the manufacturer. Additional tissue-specific cDNA libraries include human fetal brain (Stratagene, Cat. 936206), human testis (Clonetech Cat. HL3024), human thymus (Clonetech Cat. HL1127n), human brain (Clonetech Cat. HL11810), human placenta (Clonetech Cat 1075b), and human skeletal muscle (Clonetech Cat. HL1124b).

The cDNA libraries were plated with their host cells on NZCYM plates, and filter lifts are made in duplicate from each plate as per Maniatis et al. (1982). Insert (human) DNA from the candidate genomic clones was purified and radioactively labeled to high specific activity. The radioactive DNA was then hybridized to the cDNA filters to identify those cDNAs which correspond to genes located within the candidate cosmid clone. cDNAs identified by this method were picked, replated, and screened again with the labeled clone insert or its derived EcoRI fragment DNA to verify their positive status. Clones that were positive after this second round of screening were then grown up and their DNA purified for Southern blot analysis and sequencing. Clones were either purified as plasmid through in vivo excision of the plasmid from the Lambda vector as described in the protocols from the manufacturers, or isolated from the Lambda vector as a restriction fragment and subcloned into plasmid vector.

The Southern blot analysis was performed in duplicate, one using the original genomic insert DNA as a probe to verify that cDNA insert contains hybridizing sequences. The second blot was hybridized with cDNA insert DNA from the largest cDNA clone to identify which clones represent the same gene. All cDNAs which hybridize with the genomic clone and are unique were sequenced and the DNA analyzed to determine if the sequences represent known or unique genes.

All cDNA clones which appear to be unique were further analyzed as candidate BRCA2 loci. Specifically, the clones are hybridized to Northern blots to look for breast specific expression and differential expression in normal versus breast tumor RNAs. They are also analyzed by PCR on =clones in the BRCA2 region to verify their location. To map the extent of the locus, full length cDNAs are isolated and their sequences used as PCR probes on the YACs and the clones surrounding and including the original identifying clones. Intron-exon boundaries are then further defined through sequence analysis.

We have screened the normal breast, 8 month pregnant breast and fetal brain cDNA libraries with Eco RI fragments from cosmid BAC and P1 clones in the region. Potential BRCA2 cDNA clones were identified among the three libraries. Clones were picked, replated, and screened again with the original probe to verify that they were positive.

Analysis of hybrid-selected cDNA. cDNA fragments obtained from direct selection were checked by Southern blot hybridization against the probe DNA to verify that they originated from the contig. Those that passed this test were sequenced in their entirety. The set of DNA sequences obtained in this way were then checked against each other to find independent clones that overlapped.

The direct selection of cDNA method (Lovett et al., 1991; Futreal, 1993) is utilized with P1 and BAC DNA as the probe. The probe DNA is digested with a blunt cutting restriction enzyme such as HaeIII. Double-stranded adapters are then ligated onto the DNA and serve as binding sites for primers in subsequent PCR amplification reactions using biotinylated primers. Target cDNA is (generated from mRNA derived from tissue samples, e.g., breast tissue, by synthesis of either random primed or oligo(dT) primed first strand, followed by second strand synthesis. The cDNA ends are rendered blunt and ligated onto double-stranded adapters. These adapters serve as amplification sites for PCR. The target and probe sequences are denatured and mixed with human $C_o$t-1 DNA to block repetitive sequences. Solution hybridization is carried out to high $C_o$t-½ values to ensure hybridization of rare target cDNA molecules. The annealed material is then captured on avidin beads, washed at high stringency and the retained cDNAs are eluted and amplified by PCR. The selected cDNA is subjected to further rounds of enrichment before cloning into a plasmid vector for analysis.

HTF island analysis. A method for identifying cosmids to use as probes on the cDNA libraries was HTF island analysis. HTF islands are segments of DNA which contain a very high frequency of unmethylated CpG dinucleotides (Tonolio et al., 1990) and are revealed by the clustering of restriction sites of enzymes whose recognition sequences include CpG dinucleotides. Enzymes known to be useful in HTF-island analysis are AscI, NotI, BssHII, EagI, SacII, NaeI, NarI, SmaI, and MluI (Anand, 1992).

Analysis of candidate clones. One or more of the candidate genes generated from above were sequenced and the information used for identification and classification of each expressed gene. The DNA sequences were compared to known genes by nucleotide sequence comparisons and by translation in all frames followed by a comparison with known amino acid sequences. This was accomplished using Genetic Data Environment (GDE) version 2.2 software and the Basic Local Alignment Search Tool (Blast) series of client/server software packages (e.g., BLASTN 1.3.13MP), for sequence comparison against both local and remote sequence databases (e.g., GenBank), running on Sun SPARC workstations. Sequences reconstructed from collections of cDNA clones identified with the cosmids and P1s have been generated. All candidate genes that represented new sequences were analyzed further to test their candidacy for the putative BRCA2 locus.

Mutation screening. To screen for mutations in the affected pedigrees, two different approaches were followed. First, genomic DNA isolated from family members known to carry the susceptibility allele of BRCA2 was used as a template for amplification of candidate gene sequences by PCR. If the PCR primers flank or overlap an intron/exon boundary, the amplified fragment will be larger than predicted from the cDNA sequence or will not be present in the amplified mixture. By a combination of such amplification experiments and sequencing of P1 or BAC clones using the set of designed primers it is possible to establish the intron/exon structure and ultimately obtain the DNA sequences of genomic DNA from the kindreds.

A second approach that is much more rapid if the intron/exon structure of the candidate gene is complex involves sequencing fragments amplified from cDNA synthesized from lymphocyte mRNA extracted from pedigree blood which was used as a substrate for PCR amplification using the set of designed primers. If the candidate gene is expressed to a significant extent in lymphocytes, such experiments usually produce amplified fragments that can be sequenced directly without knowledge of intron/exon junctions.

The products of such sequencing reactions were analyzed by gel electrophoresis to determine positions in the sequence that contain either mutations such as deletions or insertions, or base pair substitutions that cause amino acid changes or other detrimental effects.

Any sequence within the BRCA2 region that is expressed in breast is considered to be a =candidate gene for BRCA2. Compelling evidence that a given candidate gene corresponds to BRCA2 comes from a demonstration that kindred families contain defective alleles of the candidate.

2. Specific Methods

Hybrid selection. Two distinct methods of hybrid selection were used in this work.

Method 1: cDNA preparation and selection. Randomly primed cDNA was prepared from poly $(A)^+$RNA of mammary gland, ovary testis, fetal brain and placenta tissues and from total RNA of the cell line Caco-2 (ATCC HTB 37). cDNAs were homopolymer tailed and then hybrid selected for two consecutive rounds of hybridization to immobilized P1 or BAC DNA as described previously. (Parimoo et al., 1991; Rommens et al., 1994). Groups of two to four overlapping P1 and/or BAC clones were used in individual selection experiments. Hybridizing cDNA was collected, passed over a G50 Fine Sephadex column and amplified using tailed primers. The products were then digested with EcoRI, size selected on agarose gels, and ligated into pBluescript (Stratagene) that had been digested with EcoRI and treated with calf alkaline phosphatase (Boehringer Mannheim). Ligation products were transformed into competent DH5α *E. coli* cells (Life Technologies, Inc.).

Characterization of Retrieved cDNAs. 200 to 300 individual colonies from each ligation (from each 250 kbases of genomic DNA) were picked and gridded into microtiter plates for ordering and storage. Cultures were replica transferred onto Hybond N membranes (Amersham) supported by LB agar with ampicillin. Colonies were allowed to propagate and were subsequently lysed with standard procedures. Initial analysis of the cDNA clones involved a prescreen for ribosomal sequences and subsequent cross screenings for detection of overlap and redundancy.

Approximately 10–25% of the clones were eliminated as they hybridized strongly with radiolabeled cDNA obtained from total RNA. Plasmids from 25 to 50 clones from each selection experiment that did not hybridize in prescreening were isolated for further analysis. The retrieved cDNA fragments were verified to originate from individual starting genomic clones by hybridization to restriction digests of DNAs of the starting clones, of a hamster hybrid cell line (GM10898A) that contains chromosome 13 as its only human material and to human genomic DNA. The clones were tentatively assigned into groups based on the overlapping or non-overlapping intervals of the genomic clones. Of the clones tested, approximately 85% mapped appropriately to the starting clones.

Method 2 (Lovett et al., 1991): cDNA Preparation. Poly (A) enriched RNA from human mammary gland, brain, lymphocyte and stomach were reverse-transcribed using the tailed random primer $XN_{12}$

[5'-(NH$_2$)-GTAGTGCAAGGCTCGAGAACNNNNNNNNNN] (SEQ ID NO:3)

and Superscript II reverse transcriptase (Gibco BRL). After second strand synthesis and end polishing, the ds cDNA was purified on Sepharose CL-4B columns (Pharmacia). cDNAs were "anchored" by ligation of a double-stranded oligo RP

[5'-(NH$_2$)-TGAGTAGAATTCTAACGGCCGTCATTGTTC (SEQ ID NO:4)

annealed to

5'-GAACAATGACGGCCGTTAGAATTCTACTCA-(NH$_2$) (SEQ ID NO:5)]

to their 5' ends (5' relative to mRNA) using T4 DNA ligase. Anchored ds cDNA was then repurified on Sepharose CL-4B columns.

Selection. cDNAs from mammary gland, brain, lymphocyte and stomach tissues were first amplified using a nested version of RP (RP.A: 5'-TGAGTAGAATTCTAACGGCCGTCAT) (SEQ ID NO:6)

and

XPCR [5'-(PO$_4$)-GTAGTGCAAGGCTCGAGAAC (SEQ ID NO:7)]

and purified by fractionation on Sepharose CL-4B. Selection probes were prepared from purified P1s, BACs or PACs by digestion with HinfI and Exonuclease III. The single-stranded probe was photolabelled with photobiotin (Gibco BRL) according to the manufacturer's recommendations. Probe, cDNA and Cot-1 DNA were hybridized in 2.4M TEA-CL, 10 mM NaPO$_4$, 1 mM EDTA. Hybridized cDNAs were captured on streptavidin-paramagnetic particles (Dynal), eluted, reamplified with a further nested version of RP

[RP.B: 5'-(PO$_4$)-TGAGTAGAATTCTAACGGCCGTCATTG (SEQ ID NO:8)]

and XPCR, and size-selected on Sepharose CL-6B. The selected, amplified cDNA was hybridized with an additional aliquot of probe and $C_o$t-1 DNA. Captured and eluted products were amplified again with RP.B and XPCR, size-selected by gel electrophoresis and cloned into dephosphorylated HincII cut pUC18. Ligation products were transformed into XL2-Blue ultra-competent cells (Stratagene).

Analysis. Approximately 192 colonies for each single-probe selection experiment were amplified by colony PCR using vector primers and blotted in duplicate onto Zeta Probe nylon filters (Bio-Rad). The filters were hybridized using standard procedures with either random primed $C_o$t-1 DNA or probe DNA (P1, BAC or PAC). Probe-positive, $C_o$t-1 negative clones were sequenced in both directions using vector primers on an ABI 377 sequencer.

Exon Trapping. Exon amplification was performed using a minimally overlapping set of BACs, P1s and PACs in order to isolate a number of gene sequences from the BRCA2 candidate region. Pools of genomic clones were assembled, containing from 100–300 kb of DNA in the form of 1–3 overlapping genomic clones. Genomic clones were digested with PstI or BamHI+BglII and ligated into PstI or BamHI sites of the pSPL3 splicing vector. The exon amplification technique was performed (Church et al., 1993) and the end products were cloned in the pAMP1 plasmid from the Uracil DNA Glycosylase cloning system (BRL). Approximately 6000 clones were picked, propagated in 96 well plates, stamped onto filters, and analyzed for the presence of vector and repeat sequences by hybridization. Each clone insert was PCR amplified and tested for redundancy, localization and human specificity by hybridization to grids of exons and dot blots of the parent genomic DNA. Unique candidate exons were sequenced, searched against the databases, and used for hybridization to cDNA libraries.

5' RACE. The 5' end of BRCA2 was identified by a modified RACE protocol called biotin capture RACE. Poly (A) enriched RNA from human mammary gland and thymus was reverse-transcribed using the tailed random primer $XN_{12}$

[5'(NH$_2$)-GTAGTGCAAGGCTCGAGAACNNN (SEQ ID NO:3)]

and Superscript II reverse transcriptase (Gibco BRL). The RNA strand was hydrolyzed in NaOH and first strand cDNA purified by fractionation on Sepharose CL-4B (Pharmacia). First strand cDNAs were "anchored" by ligation of a double-stranded oligo with a 7 bp random 5' overhang [ds UCA: 5'-CCTTCACACGCGTATCGATTAGTCACNNNNNNN-(NH$_2$) (SEQ ID NO:9) annealed to 5'-(PO$_4$)-GTGACTAATCGATACGCGTGTGAAGGTGC (SEQ ID NO:10)] to their 3' ends using T4 DNA ligase. After ligation, the anchored cDNA was repurified by fractionation on Sepharose CL-4B. The 5' end of BRCA2 was amplified using a biotinylated reverse primer [5'-(B)-TTGAAGAACAACAGGACTTTCACTA] (SEQ ID NO:11) and a nested version of UCA [UCP.A: 5'-CACCTTCACACGCGTATCG (SEQ ID NO:12)]. PCR products were fractionated. on an agarose gel, gel purified, and captured on streptavidin-paramagnetic particles (Dynal). Captured cDNA was reamplified using a nested reverse primer [5'-GTTCGTAATTGTTGTTTTTATGTTCAG] (SEQ ID NO:13) and a further nested version of UCA [UCP.B: 5'-CCTTCACACGCGTATCGATTAG] (SEQ ID NO:14)]. This PCR reaction gave a single sharp band on an agarose gel; the DNA was gel purified and sequenced in both directions on an ABI 377 sequencer.

cDNA Clones. Human cDNA libraries were screened with $^{32}$P-labeled hybrid selected or exon trapped clones. Phage eluted from tertiary plaques were PCR amplified with vector-specific primers and then sequenced on an ABI 377 sequencer.

Northern Blots. Multiple Tissue Northern (MTN) filters, which are loaded with 2 µg per lane of poly(A)+RNA derived from a number of human tissues, were purchased from Clonetech. $^{32}$P-random-primer labeled probes corresponding to retrieved cDNAs GT 713 (BRCA2 exons 3–7), k wCPF1B8.1 (3' end of exon 11 into exon 20), and glyceraldehyde-3-phosphate dehydrogenase (GAPDH) were used to probe the filters. Prehybridizations were at 42° C. in 50% formamide, 5×SSPE, 1% SDS, 5×Denhardt's mixture, 0.2 mg/ml denatured salmon testis DNA and 2 μg/ml poly (A). Hybridizations were in the same solution with the addition of dextran sulfate to 4% and probe. Stringency washes were in 0.1×SSC/0.1% SDS at RT-PCR Analysis. Ten μg of total RNA extracted from five human breast cancer cell lines (ZR-75-1, T-47D, MDA-MB-231, MDA-MB468 and BT-20) and three human prostate cancer cell lines (LNCaP, DU145 and PC-3) (RNAs provided by Dr. Claude Labrie, CHUL Research Center) were reverse transcribed using the primer mH20-D105#RA

[5'-TTTGGATCATTTTCACACTGTC] (SEQ ID NO:15)]

and Superscript II reverse transcriptase (Gibco BRL). Thereafter, the single strand cDNAs were amplified using the primers CG0269FB:

[5'-GTGCTCATAGTCAGAAATGAAG] (SEQ ID NO:16)]

and mH20-1D05#RA (this is the primer pair that was used to island hop from the exon 7/8 junction into exon 11; the PCR product is about 1.55 kb). PCR products were fractionated on a 1.2% agarose gel.

PCR Amplification and Mutation Screening. All 26 coding exons of BRCA2 and their associated splice sites were amplified from genomic DNA as described (Kamb et al., 1994b). The DNA sequences of the primers, some of which lie in flanking intron sequence, used for amplification and sequencing appear in Table 2. Some of the exons (2 through 10, 11-5, 11-6, 11-7 and 23 through 27) were amplified by a simple one-step method. The PCR conditions for those exons were: single denaturing step of 95° C. (1 min.); 40 cycles of 96° C. (6 sec.), $T_{ann.}$=55° C. (15 sec.), 72° C. (1 min.). Other exons (11–22) required nested reamplification after the primary PCR reaction. In these cases, the initial amplification was carried out with the primers in the first two columns of Table 2 for 19 cycles as described above. Nested reamplification for these exons was carried out for 28 or 32 cycles at the same conditions with the primers appearing in the third column of Table 2. The buffer conditions were as described (Kamb et al., 1994b). The products were purified from 0.8% agarose gels using Qiaex beads (Qiagen). The purified products were analyzed by cycle sequencing with $\alpha$-$P^{32}$dATP with Ampli-Cycle™ Sequencing Kit (Perkin Elmer, Branchburg, N.J.). The reaction products were fractionated on 6% polyacrylamide gels. All (A) reactions were loaded adjacent each other, followed by the (C) reactions, etc. Detection of polymorphisms was carried out visually and confirmed on the other strand.

TABLE 2

Primers for Amplifying BRCA2 Exons

| EXON | FORWARD PRIMER | REVERSE PRIMER | NESTED PRIMER |
|---|---|---|---|
| 2 | TGTTCCCATCCTCACAGTAAG*[17] | GTACTGGGTTTTTAGCAAGCA*[18] | |
| 3 | GGTTAAAACTAAGGTGGGA*[19] | ATTTGCCCAGCATGACACA*[20] | |
| 4 | TTTCCCAGTATAGAGGAGA*[21] | GTAGGAAAATGTTTCATTTAA*[22] | |
| 5 | ATCTAAAGTAGTATTCCAACA*[23] | GGGGGTAAAAAAAGGGGAA*[24] | |
| 6 | GAGATAAGTCAGGTATGATT*[25] | AATTGCCTGTATGAGGCAGA*[26] | |
| 7 | GGCAATTCAGTAAACGTTAA*[27] | ATTGTCAGTTACTAACACAC*[28] | |
| 8 | GTGTCATGTAATCAAATAGT*[29] | CAGGTTTAGAGACTTTCTC*[30] | |
| 9 | GGACCTAGGTTGATTGCA*[31] | GTCAAGAAAGGTAAGGTAA*[32] | |
| 10-1 | CTATGAGAAAGGTTGTGAG*[33] | CCTAGTCTTGCTAGTTCTT*[34] | |
| 10-2 | AACAGTTGTAGATACCTCTGAA*[35] | GACTTTTTGATACCCTGAAATG*[36] | |
| 10-3 | CAGCATCTTGAATCTCATACAG*[37] | CATGTATACAGATGATGCCTAAG*[38] | |
| 11-1 | AACTTAGTGAAAAATATTTAGTGA*[39] | ATACATCTTGATTCTTTTCCAT*[40] | TTTAGTGAATGTGATTGATGGT*[41] |
| 11-2 | AGAACCAACTTTGTCCTTAA*[42] | TTAGATTTGTGTTTTGGTTGAA*[43] | TAGCTCTTTTGGGACAATTC*[44] |
| 11-3 | ATGGAAAAGAATCAAGATGTAT*[45] | CCTAATGTTATGTTCAGAGAG*[46] | GCTACCTCCAAAACTGTGA*[47] |
| 11-4 | GTGTAAAGCAGCATATAAAAAT*[48] | CTTGCTGCTGTCTACCTG*[49] | AGTGGTCTTAAGATAGTCAT*[50] |
| 11-5 | CCATAATTTAACACCTAGCCA**[51] | CCAAAAAAGTTAAATCTGACA**[52] | |
| | GGCTTTTATTCTGCTCATGGC*[53] | CCTCTGCAGAAGTTTCCTCAC*[54] | |
| 11-6 | AACGGACTTGCTATTTACTGA*[55] | AGTACCTTGCTCTTTTTCATC*[56] | |
| 11-7 | CAGCTAGCGGGAAAAAAGTTA*[57] | TTCGGAGAGATGATTTTTGTC*[58] | |
| 11-8 | GCCTTAGCTTTTTACACAA*[59] | TTTTTGATTATATCTCGTTG*[60] | TTATTCTCGTTGTTTTCCTTA*[61] |
| 11-9 | CCATTAAATTGTCCATATCTA*[62] | GACGTAGGTGAATAGTGAAGA*[63] | TCAAATTCCTCTAACACTCC*[64] |
| 11-10 | GAAGATAGTACCAAGCAAGTC*[65] | TGAGACTTTGGTTCCTAATAC*[66] | AGTAACGAACATTCAGACCAG*[67] |
| 11-11 | GTCTTCACTATTCACCTACG*[68] | CCCCCAAACTGACTACACAA*[69] | AGCATACCAAGTCTACTGAAT*[70] |
| 12 | ACTCTTTCAAACATTAGGTCA*[71] | TTGGAGAGGCAGGTGGAT*[72] | CTATAGAGGGAGAACAGAT*[73] |
| 13 | TTTATGCTGATTTCTGTTGTAT*[74] | ATAAAACGGGAAGTGTTAACT*[75] | CTGTGAGTTATTTGGTGCAT*[76] |
| 14 | GAATACAAAACAGTTACCAGA*[77] | CACCACCAAAGGGGGAAA*[78] | AAATGAGGGTCTGCAACAAA*[79] |
| 15 | GTCCGACCAGAACTTGAG*[80] | AGCCATTTGTAGGATACTAG*[81] | CTACTAGACGGGCGGAG*[82] |
| 16 | ATGTTTTTGTAGTGAAGATTCT*[83] | TAGTTCGAGAGACAGTTAAG*[84] | CAGTTTTGGTTTGTTATAATTG*[85] |
| 17 | CAGAGAATAGTTGTAGTTGTT*[86] | AACCTTAACCCATACTGCC*[87] | TTCAGTATCATCCTATGTGG*[88] |
| 18 | TTTTATTCTCGTTATTCAGTG*[89] | GAAATTGAGCATCCTTAGTAA*[90] | AATTCTAGAGTCACACTTCC*[91] |
| 19 | ATATTTTTAAGGCAGTTCTAGA*[92] | TTACACACACCAAAAAAGTCA*[93] | TGAAAACTCTTTATGATATCTGT*[94] |
| 20 | TGAATGTTATATATGTGACTTTT*[95] | CTTGTTGCTATTCTTTGTCTA*[96] | CCCTAGATACTAAAAAATAAAG*[97] |
| 21 | CTTTTAGCAGTTATATAGTTTC*[98] | GCCAGAGAGTCTAAAACAG*[99] | CTTTGGGTGTTTTATGCTTG*[100] |
| 22 | TTTGTTGTATTTGTCCTGTTTA*[101] | ATTTTGTTAGTAAGGTCATTTTT*[102] | GTTCTGATTGCTTTTTATTCC*[103] |

TABLE 2-continued

Primers for Amplifying BRCA2 Exons

| EXON | FORWARD PRIMER | REVERSE PRIMER | NESTED PRIMER |
|---|---|---|---|
| 23 | ATCACTTCTTCCATTGCATC*(104) | CCGTGGCTGGTAAATCTG*(105) | |
| 24 | CTGGTAGCTCCAACTAATC*(106) | ACCGGTACAAACCTTTCATTG*(107) | |
| 25 | CTATTTTGATTTGCTTTTATTATT*(108) | GCTATTTCCTTGATACTGGAC*(109) | |
| 26 | TTGGAAACATAAATATGTGGG*(110) | ACTTACAGGAGCCACATAAC*(111) | |
| 27 | CTACATTAATTATGATAGGCTNCG**(112) | GTACTAATGTGTGGTTTGAAA**(113) | |
| | | TCAATGCAAGTTCTTCGTCAGC*(114) | |

Primers with an "*" were used for sequencing.
Primers without an "*" were replaced by the internal nested primer for both the second round of PCR and sequencing.
For large exons requiring internal sequencing primers, primers with an "**" were used to amplify the exon
Number in parathensis referes to the SEQ ID NO: for each primer.

EXAMPLE 4

Identification of BRCA2

Figure 2:
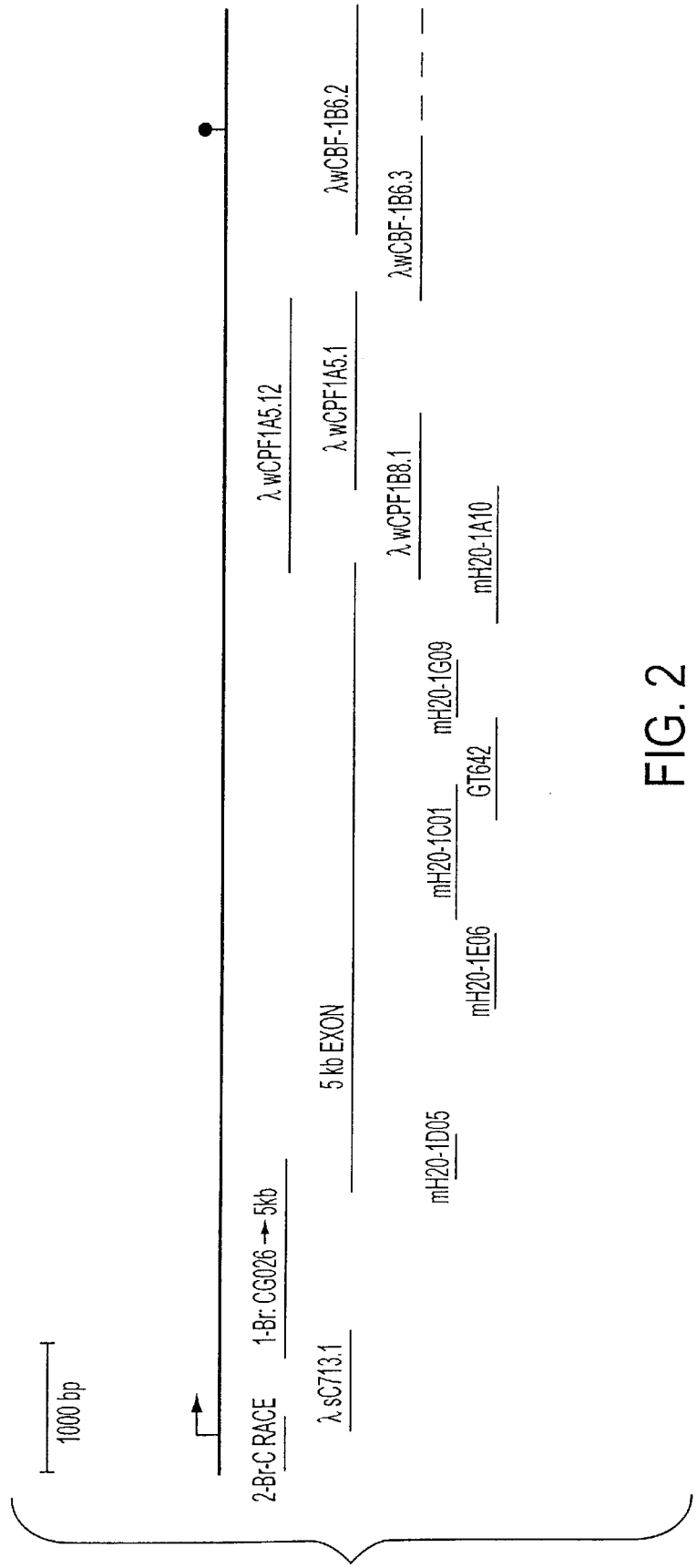
Figure 4:
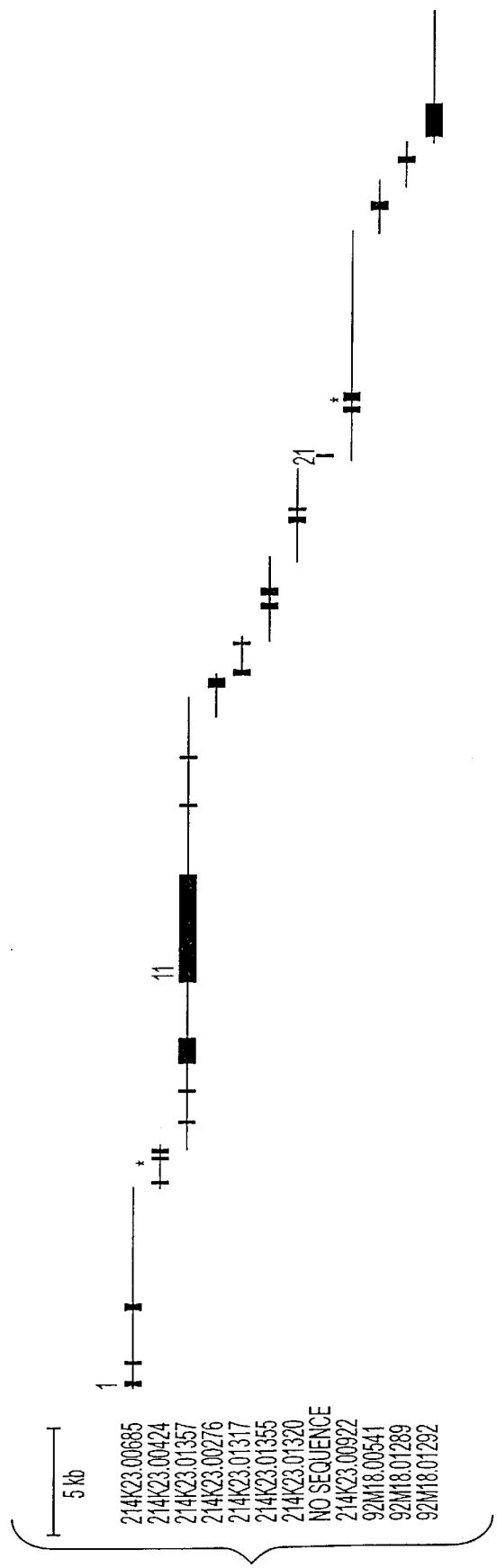
Figure 5A:
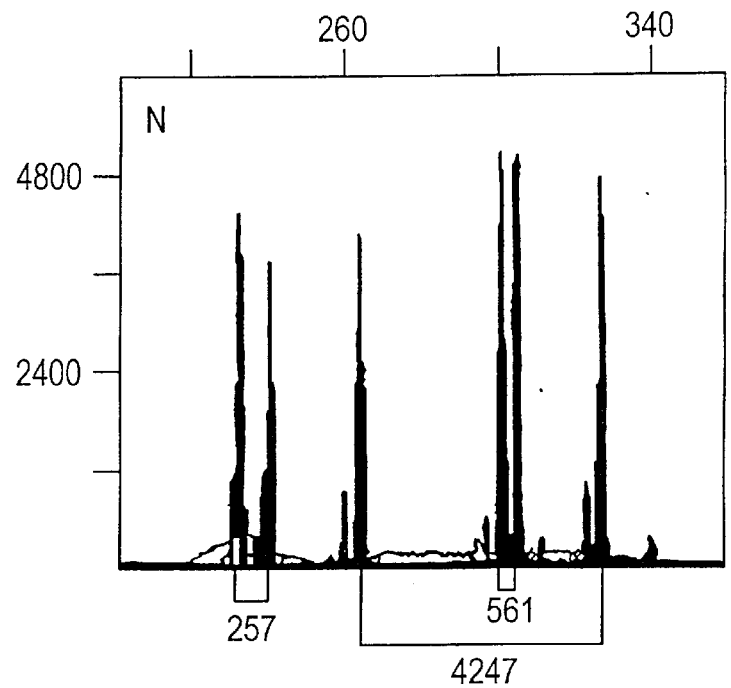
Figure 5B:
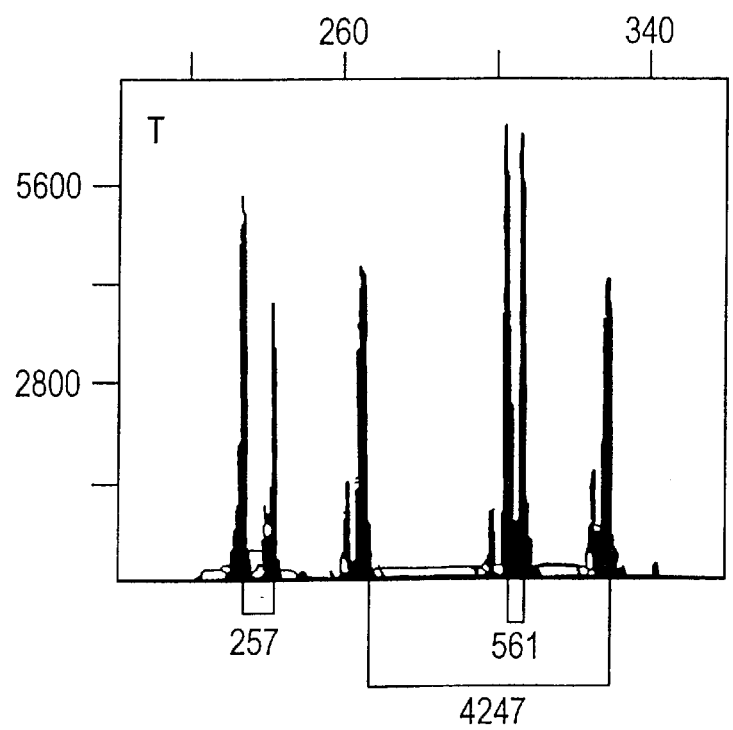
Figure 5C:
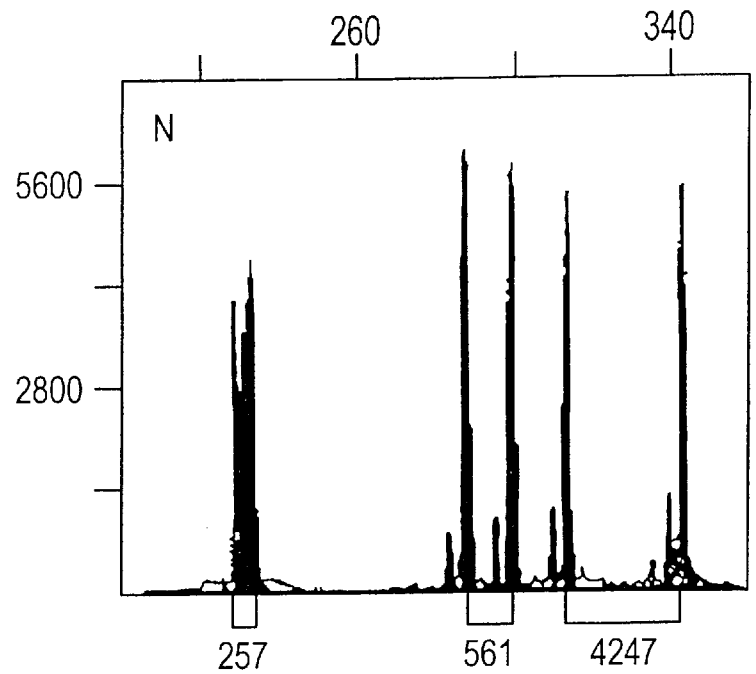
Figure 5D:
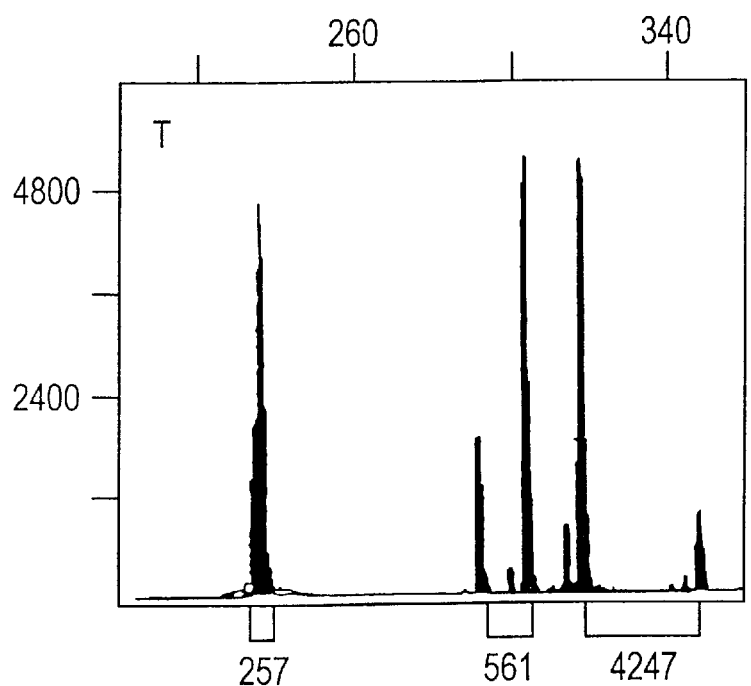

Assembly of the full-length BRCA2 sequence. The full-length sequence of BRCA2 was assembled by combination of several smaller sequences obtained from hybrid selection, exon trapping, cDNA library screening, genomic sequencing, and PCR experiments using cDNA as template for amplification (i.e., "island hopping") (FIG. 2). The extreme 5' end of the mRNA including the predicted translational start site was identified by a modified 5'RACE protocol (Stone et al., 1995). The first nucleotide in the sequence (nucleotide 1) is a non-template G, an indication that the mRNA cap is contained in the sequence. One of the exons (exon 11) located on the interior of the BRCA2 cDNA is nearly 5 kb. A portion of exon 11 was identified by analysis of roughly 900 kb of genomic sequence in the public domain (ftp://genome.wust1.edu/pub/gscl/brca). This genomic sequence was condensed with genomic sequence determined by us into a set of 160 sequence contigs. When the condensed genomic sequence was scanned for open reading frames (ORFs), a contiguous stretch of nearly 5 kb was identified that was spanned by long ORFs. This sequence was linked together by island hopping experiments with two previously identified candidate gene fragments. The current composite BRCA2 cDNA sequence consists of 11,385 bp, but does not include the polyadenylation signal or poly(A) tail. This cDNA sequence is set forth in SEQ ID NO:1 and FIG. 3.

Structure of the BRCA2 gene and BRCA2 polypeptide. Conceptual translation of the cDNA revealed an ORF that began at nucleotide 229 and encoded a predicted protein of 3418 amino acids. The peptide bears no discernible similarity to other proteins apart from sequence composition. There is no signal sequence at the amino terminus, and no obvious membrane-spanning regions. Like BRCA1, the BRCA2 protein is highly charged. Roughly one quarter of the residues are acidic or basic.

The BRCA2 gene structure was determined by comparison of cDNA and genomic sequences. BRCA2 is composed of 27 exons distributed over roughly 70 kb of genomic DNA.

A CpG-rich region at the 5' end of BRCA2 extending upstream suggests the presence of regulatory signals often associated with CpG "islands." Based on Southern blot experiments, BRCA2 appears to be unique, with no close homologs in the human genome.

Expression studies of BRCA2. Hybridization of labeled cDNA to human multiple tissue Northern filters revealed an 11–12 kb transcript that was detectable in testis only. The size of the this transcript suggests that little of the BRCA2 mRNA sequence is missing from our composite cDNA. Because the Northern filters did not include mammary gland RNA, RT-PCR experiments using a BRCA2 cDNA amplicon were performed on five breast and three prostate cancer cell line RNAs. All of the lines produced positive signals. In addition, PCR of a BRCA2 amplicon (1-BrCGO26→5kb) and 5' RACE were used to compare mammary gland and thymus cDNA as templates for amplification. In both cases, the product amplified more efficiently from breast than from thymus.

Germline mutations in BRCA2. Individuals from eighteen putative BRCA2 kindreds were screened for BRCA2 germline mutations by DNA sequence analysis (Wooster et al., 1994). Twelve kindreds have at least one case of male breast cancer, four have two or more cases; and, four include at least one individual affected with ovarian cancer who shares the linked BRCA2 haplotype. Each of the 18 kindreds has a posterior probability of harboring a BRCA2 mutation of at least 69%, and nine kindreds have posterior probabilities greater than 90%. Based on these combined probabilities, 16 of 18 kindreds are expected to segregate BRCA2 mutations. The entire coding sequence and associated splice junctions were screened for mutations in multiple individuals from nine kindreds using either cDNA or genomic DNA (Table 3). Individuals from the remaining nine kindreds were screened for mutations using only genomic DNA. These latter screening experiments encompassed 99% of the coding sequence (all exons excluding exon 15) and all but two of the splice junctions.

TABLE 3

Set of Families Screened for BRCA2 Mutations

| Family | FBC | FBC <50 yrs | Ov | MBC | LOD | Prior Probability | BRCA2 Mutation | Exon | Codon | Effect |
|---|---|---|---|---|---|---|---|---|---|---|
| UT-107[1] | 20 | 18 | 2 | 3 | 5.06 | 1.00 | 277 delAC | 2 | 17 | termination codon at 29 |
| UT-1018[1] | 11 | 9 | 0 | 1 | 2.47 | 1.00 | 982 del4 | 9 | 252 | termination codon at 275 |
| UT-2044[1] | 8 | 6 | 4 | 1 | 2.13 | 1.00 | 4706 del4 | 11 | 1493 | termination codon at 1502 |
| UT-2367[1] | 6 | 5 | 1 | 0 | 2.09 | 0.99 | IR | | | |
| UT-2327[1] | 13 | 6 | 0 | 0 | 1.92 | 0.99 | ND | | | |
| UT-2388[1] | 3 | 3 | 1 | 0 | 0.92 | 0.92 | ND | | | |
| UT-2328[1] | 10 | 4 | 0 | 1 | 0.21 | 0.87 | ND | | | |
| UT-4328[1] | 4 | 3 | 0 | 0 | 0.18 | 0.69 | ND | | | |
| MI-1016[1] | 4 | 2 | 0 | 1 | 0.04 | 0.81 | ND | | | |
| CU-20[2] | 4 | 3 | 2 | 2 | 1.09 | 1.00 | 8525 delC | 18 | 2766 | termination codon at 2776 |
| CU-159[2] | 8 | 4 | 0 | 0 | 0.99 | 0.94 | 9254 del 5 | 23 | 3009 | termination codon at 3015 |
| UT-2043[2] | 2 | 2 | 1 | 1 | 0.86 | 0.97 | 4075 delGT | 11 | 1283 | termination codon at 1285 |
| IC-2204[2] | 3 | 1 | 0 | 4 | 0.51 | 0.98 | 999 del5 | 9 | 257 | termination codon at 273 |
| MS-075[2] | 4 | 1 | 0 | 1 | 0.50 | 0.93 | 6174 delT | 11 | 1982 | termination codon at 2003 |
| UT-1019[2] | 5 | 1 | 0 | 2 | nd | 0.95 | 4132 del3 | 11 | 1302 | deletion of $thr_{1302}$ |
| UT-2027[2] | 4 | 4 | 0 | 1 | 0.39 | 0.79 | ND | | | |
| UT-2263[2] | 3 | 2 | 0 | 1 | nd | 0.9 | ND | | | |
| UT-2171[2] | 5 | 4 | 2 | 0 | nd | nd | ND | | | |

[1]Families screened for complete coding sequence and with informative cDNA sample.
[2]Families screened for all BRCA2 exons except 15 and for which there was no informative cDNA sample available.
IR — inferred regulatory mutuation
ND — non detected
nd — not determined
FBC — Female Breast Cancer
Ov — Ovarian Cancer
MBC — Male Breast Cancer Sequence alterations were identified in 9 of 18 kindreds. All except one involved nucleotide deletions that altered the reading frame, leading to truncation of the predicted BRCA2 protein. The single exception contained a deletion of three nucleotides (kindred 1019). All nine mutations differed from one another. A subset of kindreds was tested for transcript loss. cDNA samples were available for a group of nine kindreds, but three of the nine kindreds in the group contained frameshift mutations. Specific polymorphic sites know to be heterozygous in genomic DNA were examined in cDNA from kindred individuals. The appearance of hemizygosity at these polymorphic sites was interpreted as evidence for a mutation leading to reduction in mRNA levels. In only one of the six cases with no detectable sequence alteration (kindred 2367) could such a regulatory mutation be inferred. In addition, one of the three kindreds with a frameshift mutation (kindred 2044) displayed signs of transcript loss. This implies that some mutations in the BRCA2 coding sequence may destabilize the transcript in addition to disrupting the protein sequence. Such mutations have been observed in BRCA1 (Friedman et al., 1995). Thus, 56% of the kindreds (10 of 18) contained an altered BRCA2 gene.

Role of BRCA2 in Cancer. Most tumor suppressor genes identified to date give rise to protein products that are absent, nonfunctional, or reduced in function. The majority of TP53 mutations are missense; some of these have been shown to produce abnormal p53 molecules that interfere with the function of the wildtype product (Shaulian et al., 1992; Srivastava et al., 1993). A similar dominant negative mechanism of action has been proposed for some adenomatous polyposis coli (APC) alleles that produce truncated molecules (Su et al., 1993), and for point mutations in the Wilms' tumor gene (WT1) that alter DNA binding of the protein (Little et al., 1993). The nature of the mutations observed in the BRCA2 coding sequence is consistent with production of either dominant negative proteins or nonfunctional proteins.

EXAMPLE 5

Analysis of the BRCA2 Gene

The structure and function of BRCA2 gene are determined according to the following methods.

Biological Studies. Mammalian expression vectors containing BRCA2 cDNA are constructed and transfected into appropriate breast carcinoma cells with lesions in the gene. Wild-type BRCA2 cDNA as well as altered BRCA2 cDNA are utilized. The altered BRCA2 cDNA can be obtained from altered BRCA2 alleles or produced as described below. Phenotypic reversion in cultures (e.g., cell morphology, doubling time, anchorage-independent growth) and in animals (e.g., tumorigenicity) is examined. The studies will employ both wild-type and mutant forms (Section B) of the gene.

Molecular Genetics Studies. In vitro mutagenesis is performed to construct deletion mutants and missense mutants (by single base-pair substitutions in individual codons and cluster charged→alanine scanning mutagenesis). The mutants are used in biological, biochemical and biophysical studies.

Mechanism Studies. The ability of BRCA2 protein to bind to known and unknown DNA sequences is examined. Its ability to transactivate promoters is analyzed by transient reporter expression systems in mammalian cells. Conventional procedures such as particle-capture and yeast two-hybrid system are used to discover and identify any functional partners. The nature and functions of the partners are characterized. These partners in turn are targets for drug discovery.

Structural Studies. Recombinant proteins are produced in E. coli, yeast, insect and/or mammalian cells and are used in crystallographical and NMR studies. Molecular modeling of the proteins is also employed. These studies facilitate structure-driven drug design.

EXAMPLE 6

Two Step Assay to Detect the Presence of BRCA2 in a Sample

Patient sample is processed according to the method disclosed by Antonarakis et al. (1985), separated through a 1% agarose gel and transferred to nylon membrane for Southern blot analysis.

Membranes are UV cross linked at 150 mJ using a GS Gene Linker (Bio-Rad). A BRCA2 probe selected from the sequence shown in FIG. 3 is subcloned into pTZ18U. The phagemids are transformed into E. Coli MV 1190 infected with M13KO7 helper phage (Bio-Rad, Richmond, Calif.). Single stranded DNA is isolated according to standard procedures (see Sambrook et al., 1989).

Blots are prehybridized for 15–30 min at 65° C. in 7% sodium dodecyl sulfate (SDS) in 0.5 M $NaPO_4$. The methods follow those described by Nguyen et al., 1992. The blots are hybridized overnight at 65° C. in 7% SDS, 0.5 M $NaPO_4$ with 25–50 ng/ml single stranded probe DNA. Post-hybridization washes consist of two 30 min washes in 5% SDS, 40 mM $NaPO_4$ at 65° C., followed by two 30 min washes in 1% SDS, 40 mM $NaPO_4$ at 65° C.

Next the blots are rinsed with phosphate buffered saline (pH 6.8) for 5 min at room temperature and incubated with 0.2% casein in PBS for 30–60 min at room temperature and rinsed in PBS for 5 min. The blots are then preincubated for 5–10 minutes in a shaking water bath at 45° C. with hybridization buffer consisting of 6 M urea, 0.3 M NaCl, and 5×Denhardt's solution (see Sambrook, et al., 1989). The buffer is removed and replaced with 50–75 $\mu$l/cm² fresh hybridization buffer plus 2.5 nM of the covalently cross-linked oligonucleotide-alkaline phosphatase conjugate with the nucleotide sequence complementary to the universal primer site (UP-AP, Bio-Rad). The blots are hybridized for 20–30 min at 45° C. and post hybridization washes are incubated at 45° C. as two 10 min washes in 6 M urea, 1×standard saline citrate (SSC), 0.1% SDS and one 10 min wash in 1×SSC, 0.1% Triton®X-100. The blots are rinsed for 10 min at room temperature with 1×SSC.

Blots are incubated for 10 min at room temperature with shaking in the substrate buffer consisting of 0.1 M diethanolamine, 1 mM $MgCl_2$, 0.02% sodium azide, pH 10.0. Individual blots are placed in heat sealable bags with substrate buffer and 0.2 mM AMPPD (3-(2'-spiroadamantane)-4-methoxy-4-(3'-phosphoryloxy)phenyl-1,2-dioxetane, disodium salt, Bio-Rad).

After a 20 min incubation at room temperature with shaking, the excess AMPPD solution is removed. The blot is exposed to X-ray film overnight. Positive bands indicate the presence of BRCA2.

EXAMPLE 7

Generation of Polyclonal Antibody against BRCA2

Segments of BRCA2 coding sequence are expressed as fusion protein in E. coli. The overexpressed protein is purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of BRCA2 coding sequence selected from the sequence shown in FIG. 3 is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. The identification of the protein as the BRCA2 fusion product is verified by protein sequencing at the N-terminus. Next, the purified protein is used as immunogen in rabbits. Rabbits are immunized with 100 $\mu$g of the protein in complete Freund's adjuvant and boosted twice in 3 week intervals, first with 100 $\mu$g of immunogen in incomplete Freund's adjuvant followed by 100 $\mu$g of immunogen in PBS. Antibody containing serum is collected two weeks thereafter.

This procedure is repeated to generate antibodies against the mutant forms of the BRCA2 gene. These antibodies, in conjunction with antibodies to wild type BRCA2, are used to detect the presence and the relative level of the mutant forms in various tissues and biological fluids.

EXAMPLE 8

Generation of Monoclonal Antibodies Specific for BRCA2

Monoclonal antibodies are generated according to the following protocol. Mice are immunized with immunogen comprising intact BRCA2 or BRCA2 peptides (wild type or mutant) conjugated to keyhole limpet hemocyanin using glutaraldehyde or EDC as is well known.

The immunogen is mixed with an adjuvant. Each mouse receives four injections of 10 to 100 $\mu$g of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988.

Cells are plated at a density of 2×10⁵ cells/well in 96 well tissue culture plates. Individual wells are examined for growth and the supernatants of wells with growth are tested for the presence of BRCA2 specific antibodies by ELISA or RIA using wild type or mutant BRCA2 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 9

Sandwich Assay for BRCA2

Monoclonal antibody is attached to a solid surface such as a plate, tube, bead, or particle.

Preferably, the antibody is attached to the well surface of a 96-well ELISA plate. 100 $\mu$l sample (e.g., serum, urine, tissue cytosol) containing the BRCA2 peptide/protein (wild-type or mutant) is added to the solid phase antibody. The sample is incubated for 2 hrs at room temperature. Next the sample fluid is decanted, and the solid phase is washed with buffer to remove unbound material. 100 $\mu$l of a second monoclonal antibody (to a different determinant on the BRCA2 peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of BRCA2 peptide/protein present in the sample, is quantitated. Separate assays are performed using monoclonal antibodies which are specific for the wild-type BRCA2 as well as monoclonal antibodies specific for each of the mutations identified in BRCA2.

EXAMPLE 10

The 6174delT Mutation is Common in Ashkenazi Jewish Women Affected by Breast Cancer The 6174delT mutation (see Table 3) has been found to be present in many cases of Ashkenazi Jewish women who have had breast cancer (Neuhausen et al., 1996). Two groups of probands comprised the ascertainment for this study. The first group was ascertained based on both age-of-onset and a positive family history. The first group consisted of probands affected with breast cancer on or before 41 years of age with or without a family history of breast cancer. Inclusion criteria for the second group were that the proband was affected with breast cancer between the ages of 41 and 51 with one or more first degree relatives affected with breast or ovarian cancer on or before the age of 50; or the proband was affected with breast cancer between the ages of 41 and 51 with two or more second degree relatives affected with breast or ovarian cancer, 1 on or before age 50; or the proband was affected between the ages of 41 and 51 with both primary breast and primary ovarian cancer. Probands were ascertained through medical oncology and genetic counseling clinics, with an effort to offer study participation to all eligible patients. Family history was obtained by a self-report questionnaire. Histologic confirmation of diagnosis was obtained for probands in all cases. Religious background was confirmed on all probands by self report or interview.

Mutation Detection

The BRCA2 6174delT mutation was detected by amplifying genomic DNA from each patient according to standard polymerase chain reaction (PCR) procedures (Saiki et al., 1985; Mullis et al., 1986; Weber and May, 1989). The primers used for the PCR are:

BC11-RP: GGGAAGCTTCATAAGTCAGTC (SEQ ID NO:115)

(forward primer) and

BC11-LP: TTTGTAATGAAGCATCTGATACC (SEQ ID NO:116)

(reverse primer).

The reactions were performed in a total volume of 10.0 µl containing 20 µg DNA with annealing at 55° C. This produces a PCR product 97 bp long in wild-type samples and 96 bp long when the 6174delT mutation is present. The radiolabeled PCR products were electrophoresed on standard 6% polyacrylamide denaturing sequencing gels at 65 W for 2 hours. The gels were then dried and autoradiographed. All the cases exhibiting the 1 bp deletion were sequenced to confirm the 6174delT mutation. For sequencing, half of the samples were amplified with one set of PCR primers and the coding strand was sequenced and the other half of the samples were amplified with a second set of PCR primers and the noncoding strand was sequenced. For one set the PCR primers were:

TD-SFB: AATGATGAATGTAGCACGC (SEQ ID NO:117)

(forward primer) and

CGORF-RH: GTCTGAATGTTCGTTACT (SEQ ID NO:118)

(reverse primer).

This results in an amplified product of 342 bp in wild-type and 341 bp for samples containing the 6174delT mutation. For this set of samples the amplified DNA was sequenced using the CGORF-RH primer for the sequencing primer. The other half of the samples were amplified using the BC11-RP forward primer and the CGORF-RH reverse primer resulting in a fragment of 183 bp in wild-type samples and 182 bp in samples containing the 6174delT mutation. This was sequenced using BC11-RP as the sequencing primer.

Results

Six out of eighty women of Ashkenazi Jewish ancestry with breast cancer before the age of 42 had the 6174delT mutation. This compares to zero cases of the mutation being present in a control group of non-Jewish women who had breast cancer before the age of 42. These cases were ascertained without regard to family history. Table 4 shows the results of the study. Four of the six cases with the 6174delT mutation had a family history of breast or ovarian cancer in a first or second degree relative. In each of two kindreds where multiple samples were available for analysis, the 6174delT mutation co-segregated with two or more cases of breast or ovarian cancer. A second cohort of 27 Ashkenazim with breast cancer at age 42–50 and a history of at least one additional relative affected with breast or ovarian cancer provided an additional estimate of the frequency of the 6174delT mutation. In this group of 27 women, two were heterozygous for the BRCA2 6174delT mutation. One of these individuals had first degree relatives with both ovarian and breast cancer. From the data presented, and assuming a penetrance similar to BRCA1 mutations (Offit et al., 1996; Langston et al., 1996), the frequency of the 6174delT mutation in Ashkenazim can be estimated to be approximately 3 per thousand. However, if the penetrance of this mutation is lower than BRCA1, then the frequency of this mutation will be higher. A more precise estimate of the carrier frequency of the 6174delT mutation in individuals of Ashkenazi Jewish ancestry will emerge from large-scale population studies.

TABLE 4

| Group | Number of subjects tested, n = | Number with 6174delT, n = | % |
|---|---|---|---|
| Group 1a | | | |
| Diagnosis before age 42, Non-Jewish[a] | 93 | 0 | (0) |
| Group 1b | | | |
| Diagnosis before age 42, Jewish[a] | 80 | 6 | (8) |
| Before age 37 | 40 | 4 | (10) |
| age 37–41 | 40 | 2 | (5) |

TABLE 4-continued

| Group | Number of subjects tested, n = | Number with 6174delT, n = | % |
|---|---|---|---|
| Group 2 | | | |
| Diagnosis ages 42–50 and family history positive[b] | 27 | 2 | (27) |

Key:
[a]Ascertained regardless of family history
[b]Family history for this group was defined as one first degree or two second degree relatives diagnosed with breast or ovarian cancer, one before age 50.

EXAMPLE 11

BRCA2 Shows a Low Somatic Mutation Rate in Breast Carcinoma and Other Cancers Including Ovarian and Pancreatic Cancers BRCA2 is a tumor suppressor gene. A homozygous deletion of this gene may lead to breast cancer as well as other cancers. A homozygous deletion in a pancreatic xenograft was instrumental in the effort to isolate BRCA2 by positional cloning. Cancer may also result if there is a loss of one BRCA2 allele and a mutation in the remaining allele (loss of heterozygosity or LOH).

Mutations in both alleles may also lead to development of cancer. For studies here, an analysis of 150 cell lines derived from different cancers revealed no cases in which there was a homozygous loss of the BRCA2 gene. Because homozygous loss is apparently rare, investigations were made to study smaller lesions such as point mutations in BRCA2. Since compound mutant heterozygotes and mutant homozygotes are rare, tumor suppressor gene inactivation nearly always involves LOH. The remaining allele, if inactive, typically contains disruptive mutations. To identify these it is useful to preselect tumors or cell lines that exhibit LOH at the locus of interest.

Identification of tumors and cell lines that exhibit LOH

A group of 104 primary breast tumor samples and a set of 269 cell lines was tested for LOH in the BRCA2 region. For primary tumors, amplifications of three short tandem repeat markers (STRs) were compared quantitatively using fluorescence. Approximately 10 ng of genomic DNA was amplified by PCR with the following three sets of fluorescently tagged STRs:

(1) mM4247.4A.2F1 ACCATCAAACACATCATCC (SEQ ID NO: 119)
mM4247.4A.2R2 AGAAAGTAACTTGGAGGGAG (SEQ ID NO: 120)
(2) STR257-FC CTCCTGAAACTGTTCCCTTGG (SEQ ID NO: 121)
STR257-RD TAATGGTGCTGGGATATTTGG (SEQ ID NO: 122)
(3) mMB561A-3.1FA2 GAATGTCGAAGAGCTTGTC (SEQ ID NO: 123)
mMB561A-3.1RB AAACATACGCTTAGCCAGAC (SEQ ID NO: 124)

The PCR products were resolved using an ABI 377 sequencer and quantified with Genescan software (ABI). For tumors, clear peak height differences between alleles amplified from normal and tumor samples were scored as having LOH. For cell lines, if one STR was heterozygous, the sample was scored as non-LOH. In only one case was a cell line or tumor miscalled based on later analysis of single base polymorphisms. The heterozygosity indices for the markers are: STR4247 =0.89; STR257=0.72; STR561A=0.88 (S. Neuhausen, personal communication; B. Swedlund, unpublished data). Based on their combined heterozygosity indices, the chance that the markers are all homozygous in a particular individual (assuming linkage equilibrium) is only one in 250. Due to the presence of normal cells in the primary tumor sample, LOH seldom eliminates the signal entirely from the allele lost in the tumor. Rather, the relative intensities of the two alleles are altered. This can be seen clearly by comparing the allelic peak heights from normal tissue with peak heights from the tumor (FIGS. 5A–5D). Based on this analysis, 30 tumors (29%) were classified as having LOH at the BRCA2 locus (Table 5), a figure that is similar to previous estimates (Collins et al., 1995; Cleton-Jansen et al., 1995).

LOH was assessed in the set of cell lines in a different fashion. Since homozygosity of all three STRs was improbable, and since normal cells were not present, apparent homozygosity at all STRs was interpreted as LOH in the BRCA2 region. Using this criterion, 85/269 of the cell lines exhibited LOH (see Table 5). The frequencies varied according to the particular tumor cell type under consideration. For example, 4/6 ovarian cell lines and 31/62 lung cancer lines displayed LOH compared with 17/81 melanoma lines and 2/11 breast cancer lines.

Sequence Analysis of LOH Primary Breast Tumors and Cell Lines

The 30 primary breast cancers identified above which showed LOH in the BRCA2 region were screened by DNA sequence analysis for sequence variants. Greater than 95% of the coding sequence and splice junctions was examined. DNA sequencing was carried out either on the ABI 377 (Applied Biosystems Division, Perkin-Elmer) or manually. For the radioactive mutation screen, the amplified products were purified by Qiagen beads (Qiagen, Inc.). DNA sequence was generated using the Cyclist sequencing kit (Stratagene) and resolved on 6% polyacrylamide gels. In parallel, non-radioactive sequencing using fluorescent labeling dyes was performed using the TaqFS sequencing kit followed by electrophoresis on ABI 377 sequencers. Samples were gridded into 96-well trays to facilitate PCR and sequencing. Dropouts of particular PCR and sequencing reactions were repeated until>95% coverage was obtained for every sample. Sequence information was analyzed with the Sequencher software (Gene Codes Corporation). All detected mutations were confirmed by sequencing a newly amplified PCR product to exclude the possibility that the sequence alteration was due to a PCR artifact.

TABLE 5

| Type | # LOH/# Screened | Percentage LOH | # Sequenced |
|---|---|---|---|
| Astrocytoma | 6/19 | 32% | 6 |
| Bladder | 6/17 | 35% | 4 |
| Breast | 2/11 | 18% | 2 |
| Colon | 2/8 | 25% | 2 |
| Glioma | 11/36 | 31% | 5 |
| Lung | 31/62 | 50% | 20 |
| Lymphoma | 0/4 | 0% | 0 |
| Melanoma | 17/81 | 21% | 9 |
| Neuroblastoma | 1/10 | 10% | 1 |
| Ovarian | 4/6 | 67% | 4 |
| Pancreatic | 1/3 | 33% | 1 |
| Prostate | 0/2 | 0% | 0 |
| Renal | 4/10 | 40% | 4 |
| Total | 85/269 | 33% (avg. = 28%) | 58 |
| Primary Breast | 30/104 | 29% | 42 |

LOH analysis of cell lines and primary breast tumors. Percentage LOH was calculated two ways: as total and as a mean of percentages (avg.).

Of the 30 samples, two specimens contained frameshift mutations, one a nonsense mutation, and two contained missense changes (although one of these tumors also contained a frameshift). The nonsense mutation would delete 156 codons at the C-terminus suggesting that the C-terminal end of BRCA2 is important for tumor suppressor activity. All sequence variants were also present in the corresponding normal DNA from these cancer patients. To exclude the unlikely possibility that preselection for LOH introduced a systematic bias against detecting mutations (e.g., dominant behavior of mutations, compound heterozygotes), 12 samples shown to be heterozygous at BRCA2 were also screened. Three of these revealed missense changes that were also found in the normal samples. Thus, in a set of 42 breast carcinoma samples, 30 of which displayed LOH at the BRCA2 locus, no somatic mutations were identified. The frameshift and nonsense changes are likely to be predisposing mutations that influenced development of breast cancer in these patients. The missense variants are rare; they were each observed only once during analysis of 115 chromosomes. From these data it is not possible to distinguish between rare neutral polymorphisms and predisposing mutations.

Of the 85 cell lines which displayed LOH (see Table 5), 58 were also screened for sequence changes. Greater than 95% of the coding sequence of each sample was screened. Only a single frameshift mutation was identified by this DNA sequence analysis. This mutation (6174delT) was present in a pancreatic cancer line and it is identical to one found in the BT111 primary tumor sample and to a previously detected germline frameshift (Tavtigian et al., 1996). This suggests that this particular frameshift may be a relatively common germline BRCA2 mutation. In addition, a number of missense sequence variants were detected (Tables 6A and 6B).

Detection of a probable germline BRCA2 mutation in a pancreatic tumor cell line suggests that BRCA2 mutations may predispose to pancreatic cancer, a possibility that has not been explored thoroughly. This mutation also adds weight to the involvement of BRCA2 in sporadic pancreatic cancer, implied previously by the homozygous deletion observed in a pancreatic xenograft (Schutte et al., 1995). Because only three pancreatic cell lines were examined in our study, further investigation of BRCA2 mutations in pancreatic cancers is warranted.

TABLE 6A

| Sample | Type | LOH | Change | Effect | Germline |
|---|---|---|---|---|---|
| 4H5 | Renal | yes | G451C | Ala→Pro | |
| 4G1 | Ovarian | yes | A1093C | Asn→His | |
| 2F8 | Lung | yes | G1291C | Val→Leu | |
| BT110 | Primary breast | yes | 1493delA | Frameshift | yes |
| 4F8 | Ovarian | yes | C2117T | Thr→Ile | |
| BT163 | Primary breast | no | A2411C | Asp→Ala | yes |
| 1D6 | Bladder | no | G4813A | Gly→Arg | |
| BT333 | Primary breast | no | T5868G | Asn→Lys | yes |
| 2A2 | Glioma | yes | C5972T | Thr→Met | |
| 2I4 | Lung | yes | C5972T | Thr→Met | |
| BT111 | Primary breast | yes | 6174delT | Frameshift | yes |
| 4G3 | Pancreatic | yes | 6174delT | Frameshift | |
| 1B7 | Astrocytoma | yes | C6328T | Arg→Cys | |
| BT118 | Primary breast | no | G7049T | Gly→Val | yes |
| BT115 | Primary breast | yes | G7491C | Gln→His | yes |
| 3D5 | Melanoma | yes | A9537G | Ile→Met | |

TABLE 6A-continued

| Sample | Type | LOH | Change | Effect | Germline |
|---|---|---|---|---|---|
| BT85 | Primary breast | yes | A10204T | Lys→Stop | yes |
| 1E4 | Breast | yes | C10298G | Thr→Arg | |
| BT110 | Primary breast | yes | A10462G | Ile→Val | yes |

Germline mutations identified in BRCA2. Listed are the mutation positions based on the Genbank entry of BRCA2 (Schutte et al., 1995).

TABLE 6B

| Position | Change | Effect | Frequency |
|---|---|---|---|
| 5'UTR(203) | G/A | — | 0.32 (0.26) |
| PM(1342) | C/A | His→Asn | 0.32 (0.37) |
| PM(2457) | T/C | silent | 0.04 (0.05) |
| PM(3199) | A/G | Asn→Asp | 0.04 (0.08) |
| PM(3624) | A/G | silent | 0.35 |
| PM(3668) | A/G | Asn→Ser | 0 (0.15) |
| PM(4035) | T/C | silent | 0.24 (0.10) |
| PM(7470) | A/G | silent | 0.26 (0.15) |
| 1593 | A→G | silent | <0.01 |
| 4296 | G→A | silent | <0.01 |
| 5691 | A→G | silent | <0.01 |
| 6051 | A→G | silent | <0.01 |
| 6828 | T→C | silent | <0.01 |
| 6921 | T→C | silent | <0.01 |

Common polymorphisms and silent substitutions detected in BRCA2 by DNA sequencing. Since some rare silent variants may affect gene function (e.g., splicing (Richard and Beckmann, 1995)), these are not preceded by "PM". The frequencies of polymorphisms shown involve the second of the nucleotide pair. Frequencies reported in a previous study are shown in parentheses (Tavtigian et al., 1996). Numbering is as in Table 6A.

Industrial Utility

As previously described above, the present invention provides materials and methods for use in testing BRCA2 alleles of an individual and an interpretation of the normal or predisposing nature of the alleles. Individuals at higher than normal risk might modify their lifestyles appropriately. In the case of BRCA2, the most significant non-genetic risk factor is the protective effect of an early, full term pregnancy. Therefore, women at risk could consider early childbearing or a therapy designed to simulate the hormonal effects of an early full-term pregnancy. Women at high risk would also strive for early detection and would be more highly motivated to learn and practice breast self examination. Such women would also be highly motivated to have regular mammograms, perhaps starting at an earlier age than the general population. Ovarian screening could also be undertaken at greater frequency. Diagnostic methods based on sequence analysis of the BRCA2 locus could also be applied to tumor detection and classification. Sequence analysis could be used to diagnose precursor lesions. With the evolution of the method and the accumulation of information about BRCA2 and other causative loci, it could become possible to separate cancers into benign and malignant.

Women with breast cancers may follow different surgical procedures if they are predisposed, and therefore likely to have additional cancers, than if they are not predisposed. Other therapies may be developed, using either peptides or small molecules (rational drug design). Peptides could be the missing gene product itself or a portion of the missing gene product. Alternatively, the therapeutic agent could be another molecule that mimics the deleterious gene's function, either a peptide or a nonpeptidic molecule that seeks to counteract the deleterious effect of the inherited locus. The therapy could also be gene based, through introduction of a normal BRCA2 allele into individuals to make a protein which will counteract the effect of the deleterious allele. These gene therapies may take many forms and may be directed either toward preventing the tumor from forming, curing a cancer once it has occurred, or stopping a cancer from metastasizing.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

American Cancer Society, Cancer Facts & Figures—1992. (American Cancer Society, Atlanta, Ga).
Anand, R. (1992). *Techniques for the Analysis of Complex Genomes,* (Academic Press).
Anderson, et al. (1980). *Proc. Natl. Acad Sci. USA* 77:5399–5403.
Anderson, D. E. (1972). *J. Natl. Cancer Inst.* 48:1029–1034.
Anderson, J. A., et al. (1 992). *J. Otolaryngology* 21:321.
Antonarakis, S. E., et al. (1985). *New Eng. J. Med.* 313:842–848.
Ausubel, F. M., et al. (1992). *Current Protocols in Molecular Biology,* (J. Wiley and Sons, N.Y.)
Beaucage & Carruthers (1981). *Tetra. Letts.* 22:1859–1862.
Berkner (1992). *Curr. Top. Microbiol. Immunol.* 158:39–61.
Berkner, et al. (1988). *BioTechniques* 6:616–629.
Bishop, D. T., el al. (1988). *Genet. Epidemiol.* 5:151–169.
Bishop, D. T. and Gardner, E. J. (1980). In: *Banbury Report 4: Cancer Incidence in Defined Populations* (J. Cairns, J. L. Lyon, M. Skolnick, eds.), Cold Spring Harbor Laboratory, Cold Spring Harbor, N.Y., 309–408.
Botstein, et al. (1980). *Am. J. Hum. Genet.* 32:314–331.
Brandyopadhyay and Temin (1984). *Mol. Cell. Biol.* 4:749–754.
Breakfield and Geller (1987). *Mol. Neurobiol.* 1:337–371.
Brinster, et al. (1981). *Cell* 27:223–231.
Buchschacher and Panganiban (1992). *J. Virol.* 66:2731–2739.
Buckler, et al. (1991). *Proc. Natl. Acad Sci. USA* 88:4005–4009.
Cannon-Albright, L., et al. (1994). *Cancer Research* 54:2378–2385.
Capecchi, M. R. (1989). *Science* 244:1288.
Cariello (1988). *Human Genetics* 42:726.
Church, D. M., et al., (1993). *Hum. Molec. Genet.* 2:1915.
Claus, E., et al. (1991). *Am. J. Hum. Genet.* 48:232–242.
Cleton-Jansen, A. M., et al. (1995). *Br. J. Cancer* 72:1241–1244.
Collins, N., et al. (1995). *Oncogene* 10:1673–1675.
Conner, B. J., et al. (1983). *Proc. Natl. Acad. Sci. USA* 80:278–282.
Constantini and Lacy (1981). *Nature* 294:92–94.
Cotten, et al. (1990). *Proc. Natl. Acad. Sci. USA* 87:4033–4037.
Cotton, et al. (1988). *Proc. Natl. Acad Sci. USA* 85:4397.
Culver, et al. (1992). *Science* 256:1550–1552.
Curiel, et al. (1991a). *Proc. Natl. Acad. Sci. USA* 88:8850–8854.
Curiel, et al. (1991 b). *Hum. Gene Ther.* 3:147–154.
Deutscher, M. (1990). *Meth. Enzymology* 182 (Academic Press, San Diego, Calif.).
Donehower, L. A., et al. (1992). *Nature* 356:215.
*Enhancers and Eukaryotic Gene Expression,* Cold Spring Harbor Press, Cold Spring Harbor, N.Y. (1983).
Easton et al. (1993). *Am. J. Hum. Gen.* 52:678–701.
Erickson, J. et al., (1990). *Science* 249:527–533.
Felgner, et al. (1987). *Proc. Natl. Acad Sci. USA* 84:7413–7417.
Fiers, et al. (1978). *Nature* 273:113.
Fink, et al. (1992). *Hum. Gene Ther.* 3:11–19.
Finkelstein, J., et al. (1990). *Genomics* 7:167–172.
Freese, et al. (1990). *Biochem. Pharmaco.* 40:2189–2199.
Friedman, T. (1991). In *Therapy for Genetic Diseases,* T. Friedman, ed., Oxford University Press, pp. 105–121.
Friedman, L. S., et al. (1995). *Am. J. Hum. Genet.* 57:1284–1297.
Futreal (1993). Ph.D. Thesis, University of North Carolina, Chapel Hill.
Futreal et al. (1994). *Science* 266:120–122.
Glover, D. (1985). *DNA Cloning,* I and II (Oxford Press).
Go, R. C. P., et al. (1983). *J. Natl. Cancer Inst.* 71:455–461.
Goding (1986). *Monoclonal Antibodies: Principles and Practice,* 2d ed. (Academic Press, N.Y.).
Godowski, et al. (1988). *Science* 241:812–816.
Gordon, et al. (1980). *Proc. Natl. Acad Sci. USA* 77:7380–7384.
Gorziglia and Kapikian (1992). *J. Virol.* 66:4407–4412.
Graham and van der Eb (1973). *Virology* 52:456–467.
Grompe, M., (1993). *Nature Genetics* 5:111–117.
Grompe, M., et al., (1989). *Proc. Natl. Acad. Sci. USA* 86:5855–5892.
Guthrie, G. & Fink, G. R. (1991). *Guide to Yeast Genetics and Molecular Biology (Academic Press).*
Hall, J. M., et al. (1990). *Science* 250:1684–1689.
Harlow & Lane (1988). *Antibodies: A Laboratory Manual* (Cold Spring Harbor Laboratory, Cold Spring Harbor, N.Y.
Hasty, P., K., et al. (1991). *Nature* 350:243.
Helseth, et al. (1990). *J. Virol.* 64:2416–2420.
Hodgson, J. (1991). *Bio/Technology* 9:19–21.
Huse, et al. (1989). *Science* 246:1275–1281.
Innis et al. (1990). *PCR Protocols. A Guide to Methods and Applications* (Academic Press, San Diego, Calif.).
Jablonski, E., et al. (1986). *Nuc. Acids Res.* 14:6115–6128.
Jakoby, W. B. and Pastan, I. H. (eds.) (1979). *Cell Culture. Methods in Enzymology,* volume 58 (Academic Press, Inc., Harcourt Brace Jovanovich (N.Y.)).
Jeffreys, et al. (1985). *Nature* 314:67–73.
Johnson, et al. (1 992). *J. Virol.* 66:2952–2965.
Kamb, A. et al. (1994a). *Science* 264:436–440.
Kamb, A. et al. (1994b). *Nature Genetics* 8:22.
Kandpal, et al. (1990). *Nucl. Acids Res.* 18:1789–1795.
Kaneda, et al. (1989). *J. Biol. Chem.* 264:12126–12129.
Kanehisa (1984). *Nucl. Acids Res.* 12:203–213.
Kinszler, K. W., et al. (1991). *Science* 251:1366–1370.
Knudson, A. G. (1993). *Nature Genet.* 5:103.
Kohler, G. and Milstein, C. (1975). *Nature* 256:495–497.
Kraemer, F. B. et al. (1993). *J. Lipid Res.* 34:663–672.
Kubo, T., et al. (1988). *FEBS Letts.* 241:119.
Landegren, et al. (1988). *Science* 242:229.
Langston, A. A., et al. (1996). *N. Engl. J. Med.* 334:137–142.
Lim, et al. (1992). *Circulation* 83:2007–2011.
Lindsay, S., et al. (1987). *Nature* 327:336–368.
Litt, et al. (1989). *Am. J. Hum. Genet.* 44:397–401.
Little, M. H., et al. (1993). *Hum. Mol. Genet.* 2:259.
Lovett, et al. (1991). *Proc. Natl. Acad. Sci. USA* 88:9628–9632.
Madzak, et al. (1992). *J. Gen. Virol.* 73:1533–1536.

Malkin, D., et al. (1990). *Science* 250:1233–1238.
Maniatis. T. et al. (1982). *Molecular Cloning. A Laboratory Manual* (Cold Spring Harbor Laboratory, Cold Spring Harbor, N.Y.).
Mann and Baltimore (1985). *J. Virol.* 54:401–407.
Margaritte, et al. (1992). *Am. J. Hum. Genet.* 50:1231–1234.
Margolskee (1992). *Curr. Top. Microbiol. Immunol.* 158:67–90.
Martin, R., et al. (1990). *Bio Techniques* 9:762–768.
Matteucci, M. D. and Caruthers, M. H. (1981). *J. Am. Chem. Soc.* 103:3185.
Matthews & Kricka (1988). *Anal. Biochem.* 169:1.
Merrifield (1963). *J. Am. Chem. Soc.* 85:2149–2156.
Mettlin, C., et al. (1990). *American Journal of Epidemiology* 131:973–983.
Metzger, et al. (1988). *Nature* 334:31–36.
Miller (1992). *Curr. Top. Microbiol. Immunol.* 158:1–24.
Miller, et al. (1985). *Mol. Cell. Biol.* 5:431–437.
Miller, et al. (1988). *J. Virol.* 62:4337–4345.
Mittlin (1989). *Clinical Chem.* 35:1819.
Modrich, P. (1991). *Ann. Rev. Genet.* 25:229–253.
Mombaerts, P., et al. (1992). *Cell* 68:869.
Moss (1992). *Curr. Top. Microbiol. Immunol.* 158:25–38.
Mullis, K., et al. (1986). *Cold Spring Harbor Symp. Quant. Biol.* 51:263–273.
Muzyczka (1992). *Curr. Top. Microbiol. Immunol.* 158:97–123.
Nabel (1992). *Hum. Gene Ther.* 3:399–410.
Nabel, et al. (1990). *Science* 249:1285–1288.
Nakamura, et al. (1987). *Science* 235:1616–1622.
Narod, S. A., et al. (1991). *The Lancet* 338:82–83.
Neuhausen, S., et al. (1996). *Nature Genetics* 13:(in press, May 1996 issue).
Newman, B., et al. (1988). *Proc. Natl. Acad Sci. USA* 85:3044–3048.
Newton, C. R., Graham, A., Heptinstall, L. E., Powell, S. J., Summers, C., Kalsheker, N., Smith, J. C., and Markham, A. F. (1989). *Nucl. Acids Res.* 17:2503–2516.
Nguyen, Q., et al. (1992). *BioTechniques* 13:116–123.
Novack, et al. (1986). *Proc. Natl. Acad Sci. USA* 83:586.
Offit, K., et al. (1996). *Lancet* (In press).
Ohi, et al. (1990). *Gene* 89:279–282.
Orita, et al. (1989). *Proc. Natl. Acad Sci. USA* 86:2776–2770.
Ott, J. (1985). *Analysis of Human Genetic Linkage*, Johns Hopkins University Press, Baltimore, Md., pp. 1–216.
Page, et al. (1990). *J. Virol.* 64:5370–5276.
Parimoo, S., et al. (1991). *Proc. Natl. Acad Sci. USA* 88:9623–9627.
Pellicer, et al. (1980). *Science* 209:1414–1422.
Petropoulos, et al. (1992). *J. Virol.* 66:3391–3397.
Philpott, K. L., et al. (1992). *Science* 256:1448.
Pierce, et al. (1992). *Proc. Natl Acad Sci. USA* 89:2056–2060.
Quantin, et al. (1992). *Proc. Natl Acad. Sci. USA* 89:2581–2584.
Rano & Kidd (1989). *Nucl. Acids Res.* 17:8392.
Richard, L. and Beckmann, J. S. (1995). *Nature Genetics* 10:259.
Rigby, P. W. J., et al. (1977). *J. Mol. Biol.* 113:237–251.
Rommens, J. M. et al. (1994). In *Identification of Transcribed Sequences*, (U. Hochgeschwender & K. Gardiner, Eds.), Plenum Press, New York, 65–79.
Rosenfeld, et al. (1992). *Cell* 68:143–155.
Saiki, R. K., et al. (1985). *Science* 230:1350–1354.
Sambrook, J., et al. (1989). *Molecular Cloning: A Laboratory Manual*, 2nd Ed. (Cold Spring Harbor Laboratory, Cold Spring Harbor, N.Y.).
Scharf (1986). *Science* 233:1076.
Schutte, M., et al. (1995). *Proc. Natl. Acad Sci.* 92:5950–5954.
Scopes, R. (1982). *Protein Purification. Principles and Practice*, (Springer-Verlag, N.Y.).
Shaulian, E., et al. (1992). *Mol. Cell Biol.* 12:5581–92.
Sheffield, V. C., et al. (1989). *Proc. Natl. Acad. Sci. USA* 86:232–236.
Sheffield, V. C., et al. (1991). *Am. J. Hum. Genet.* 49:699–706.
Shenk, et al. (1975). *Proc. Natl. Acad Sci. USA* 72:989.
Shimada, et al. (1991). *J. Clin. Invest.* 88:1043–1047.
Shinkai, Y., et al. (1992). *Cell* 68:855.
Shizuya, H., et al. (1992). *Proc. Natl. Acad Sci. USA* 89:8794–8797.
Skolnick, M. H. and Wallace, B. R. (1988). *Genomics* 2:273–279.
Skolnick, M. H., et al. (1990). *Science* 250:1715–1720.
Smith, S. A., et al. (1992). *Nature Genetics* 2:128–131.
Snouwaert, J. N., et al. (1992). *Science* 257:1083.
Sorge, et al. (1984). *Mol. Cell. Biol.* 4:1730–1737.
Srivastava, S., et al. (1993). *Cancer Res.* 53:4452–5.
Sternberg (1990). *Proc. Natl. Acad Sci. USA* 87:103–107.
Sternberg, et al. (1990). *The New Biologist* 2:151–162.
Stewart, et al. (1992). *Hum. Gene Ther.* 3:267–275.
Stone, S., et al. (1995). *Cancer Research* 55:2988–2994.
Stratford-Perricaudet, et al. (1990). *Hum. Gene Ther.* 1:241–256.
Swift, M., et al. (1991). *N. Engl. J. Med.* 325:1831–1836.
Swift, M., et al. (1976). *Cancer Res.* 36:209–215.
Su, L. K., et al. (1993). *Cancer Res.* 53:2728–31.
Tavtigian, S. V., et al. (1996). *Nature Genetics* 12:1–6.
Thomas, A. and Skolnick, M. H. (1994). *IMA Journal of Mathematics Applied in Medicine and Biology* (in press).
Tonolio, D., et al. (1990). Cold Spring Harbor Conference.
Valancius, V. & Smithies, O. (1991). *Mol. Cell Biol.* 11:1402.
Wagner, et al. (1990). *Proc. Natl. Acad. Sci. USA* 87:3410–3414.
Wagner, et al. (1991). *Proc. Natl. Acad. Sci. USA* 88:4255–4259.
Wang and Huang (1989). *Biochemistry* 28:9508–9514.
Wartell, R. M., et al. (1990). *Nucl. Acids Res.* 18:2699–2705.
Weber, J. L. (1990). *Genomics* 7:524–530.
Weber and May (1989). *Am. J. Hum. Genet.* 44:388–396.
Weber, J. L., et al. (1990). *Nucleic Acid Res.* 18:4640.
Wells, J. A. (1991). *Methods in Enzymol.* 202:390–411.
Wetmur & Davidson (1968). *J. Mol. Biol.* 31:349–370.
White, M. B., et al., (1992). *Genomics* 12:301–306.
White and Lalouel (1988). *Ann. Rev. Genet.* 22:259–279.
Wilkinson, et al. (1992). *Nucleic Acids Res.* 20:2233–2239.
Williams and Anderson (1984). *Genet. Epidemiol.* 1:7–20.
Wolff, et al. (1990). *Science* 247:1465–1468.
Wolff, et al. (1991). *BioTechniques* 11:474–485.
Wooster, R., et al. (1994). *Science* 265:2088.
Wu, et al. (1989a). *Genomics* 4:560–569.
Wu, et al. (1989b). *J. Biol. Chem.* 264:16985–16987.
Wu, et al. (1991). *J. Biol. Chem.* 266:14338–14342.
Zenke, et al. (1990). *Proc. Natl. Acad Sci. USA* 87:3655–3659.
List of Patents and Patent Applications:
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437

| | |
|---|---|
| U.S. Pat. No. 4,366,241 | U.S. Pat. No. 5,252,479 |
| U.S. Pat. No. 4,376,110 | EPO Publication No. 225,807 |
| U.S. Pat. No. 4,486,530 | European Patent Application Publication No. 0332435 |
| U.S. Pat. No. 4,683,195 | Geysen, H., PCT published application WO 84/03564, published Sep. 13, 1984 |
| U.S. Pat. No. 4,683,202 | |
| U.S. Pat. No. 4,816,567 | Hitzeman el al., EP 73,675A |
| U.S. Pat. No. 4,868,105 | PCT published application WO 93/07282 |

What is claimed is:

1. A method for identifying a mutant BRCA2 nucleotide sequence in a suspected mutant BRCA2 allele which comprises comparing the nucleotide sequence of the suspected mutant BRCA2 allele with the wild-type BRCA2 nucleotide sequence, wherein a difference between the suspected mutant and the wild-type sequences identifies a mutant BRCA2 nucleotide sequence.

2. A method for diagnosing a predisposition for breast cancer in a human subject which comprises comparing the germline sequence of the BRCA2 gene or the sequence of its mRNA in a tissue sample from said subject with the germline sequence of the wild-type BRCA2 gene or the sequence of its mRNA, wherein an alteration in the germline sequence of the BRCA2 gene or the sequence of its mRNA of the subject indicates a predisposition to said cancer.

3. The method of claim 2 wherein an alteration is detected in a regulatory region of the BRCA2 gene.

4. The method of claim 2 wherein the detection in the alteration in the germline sequence is determined by an assay selected from the group consisting of (a) observing shifts in electrophoretic mobility of single-stranded DNA on non-denaturing polyacrylamide gels, (b) hybridizing a BRCA2 gene probe to genomic DNA isolated from said tissue sample, (c) hybridizing an allele-specific probe to genomic DNA of the tissue sample, (d) amplifying all or part of the BRCA2 gene from said tissue sample to produce an amplified sequence and sequencing the amplified sequence, (e) amplifying all or part of the BRCA2 gene from said tissue sample using primers for a specific BRCA2 mutant allele, (f) molecularly cloning all or part of the BRCA2 gene from said tissue sample to produce a cloned sequence and sequencing the cloned sequence, (g) identifying a mismatch between (1) a BRCA2 gene or a BRCA2 mRNA isolated from said tissue sample, and (2) a nucleic acid probe complementary to the human wild-type BRCA2 gene sequence, when molecules (1) and (2) are hybridized to each other to form a duplex, (h) amplification of BRCA2 gene sequences in said tissue sample and hybridization of the amplified sequences to nucleic acid probes which comprise wild-type BRCA2 gene sequences, (i) amplification of BRCA2 gene sequences in said tissue sample and hybridization of the amplified sequences to nucleic acid probes which comprise mutant BRCA2 gene sequences, (j) screening for a deletion mutation in said tissue sample, (k) screening for a point mutation in said tissue sample, (l) screening for an insertion mutation in said tissue sample, (m) in situ hybridization of the BRCA2 gene of said tissue sample with nucleic acid probes which comprise the BRCA2 gene.

5. A method for detecting a mutation in a neoplastic lesion at the BRCA2 gene in a human subject which comprises comparing the sequence of the BRCA2 gene or the sequence of its mRNA in a tissue sample from a lesion of said subject with the sequence of the wild-type BRCA2 gene or the sequence of its mRNA, wherein an alteration in the sequence of the BRCA2 gene or the sequence of its mRNA of the subject indicates a mutation at the BRCA2 gene of the neoplastic lesion.

6. The method of claim 5 wherein an alteration is detected in the a regulatory regions of the BRCA2 gene.

7. The method of claim 5 wherein the detection in the alteration in the BRCA2 sequence is determined by an assay selected from the group consisting of (a) observing shifts in electrophoretic mobility of single-stranded DNA on non-denaturing polyacrylamide gels, (b) hybridizing a BRCA2 gene probe to DNA isolated from said tissue sample, (c) hybridizing an allele-specific probe to DNA of the tissue sample, (d) amplifying all or part of the BRCA2 gene from said tissue sample to produce an amplified sequence and sequencing the amplified sequence, (e) amplifying all or part of the BRCA2 gene from said tissue sample using primers for a specific BRCA2 mutant allele, (f) molecularly cloning all or part of the BRCA2 gene from said tissue sample to produce a cloned sequence and sequencing the cloned sequence, (g) identifying a mismatch between (1) a BRCA2 gene or a BRCA2 mRNA isolated from said tissue sample, and (2) a nucleic acid probe complementary to the human wild-type BRCA2 gene sequence, when molecules (1) and (2) are hybridized to each other to form a duplex, (h) amplification of BRCA2 gene sequences in said tissue sample and hybridization of the amplified sequences to nucleic acid probes which comprise wild-type BRCA2 gene sequences, (i) amplification of BRCA2 gene sequences in said tissue sample and hybridization of the amplified sequences to nucleic acid probes which comprise mutant BRCA2 gene sequences., (0) screening for a deletion mutation in said tissue sample, (k) screening for a point mutation in said tissue sample, (1) screening for an insertion mutation in said tissue sample, (m) in situ hybridization of the BRCA2 gene of said tissue sample with nucleic acid probes which comprise the BRCA2 gene.

8. A method for confirming the lack of a BRCA2 mutation in a neoplastic lesion from a human subject which comprises comparing the sequence of the BRCA2 gene or the sequence of its mRNA in a tissue sample from a lesion of said subject with the sequence of the wild-type BRCA2 gene or the sequence of its RNA, wherein the presence of the wild-type sequence in the tissue sample indicates the lack of a mutation at the BRCA2 gene.

* * * * *

UNITED STATES PATENT AND TRADEMARK OFFICE
CERTIFICATE OF CORRECTION

PATENT NO. : 6,033,857
APPLICATION NO. : 09/044946
DATED : March 7, 2000
INVENTOR(S) : Tavtigian et al.

Page 1 of 1

It is certified that error appears in the above-identified patent and that said Letters Patent is hereby corrected as shown below:

Col. 172, Claim 7, line 6, please change "(0)" to --(j)--.

Col. 172, Claim 8, line 17, please change "RNA" to --mRNA--.

Signed and Sealed this

Twenty-fourth Day of November, 2009

David J. Kappos
*Director of the United States Patent and Trademark Office*